United States Patent
Balázs et al.

(10) Patent No.: US 6,562,810 B1
(45) Date of Patent: May 13, 2003

(54) 8-SUBSTITUTED-9H-1,3-DIOXOLO/4,5-H//2,3/ BENZODIAZEPINE DERIVATIVES, AS AMPA/KAINATE RECEPTOR INHIBITORS

(75) Inventors: László Balázs, Budapest (HU); József Barkóczy, Budapest (HU); Imre Domán, Budapest (HU); András Egyed, Budapest (HU); István Gacsályi, Budapest (HU); Gábor Gigler, Budapest (HU); Zoltán Greff, Budapest (HU); István Gyertyán, Budapest (HU); Péter Kótay Nagy, Vác (HU); Attila Kovács, Dorog (HU); György Lávay, Budakeszi (HU); Zoltán Rátkai, Budapest (HU); Péter Seres, Budapest (HU); Gyula Simig, Budapest (HU); Annamária Simó, Budapest (HU); Tamás Szabados, Budapest (HU); Géza Szabó, Budapest (HU); Károly Tihanyi, Budapest (HU); Miklós Végh, Budapest (HU); Géza Schneider, Budapest (HU); Judit Cselenyák, Budapest (HU)

(73) Assignee: Egis Gyogyszergyar RT., Budapest (HU)

( * ) Notice: Subject to any disclaimer, the term of this patent is extended or adjusted under 35 U.S.C. 154(b) by 0 days.

(21) Appl. No.: 09/485,391

(22) PCT Filed: Aug. 7, 1998

(86) PCT No.: PCT/HU98/00075

§ 371 (c)(1),
(2), (4) Date: May 19, 2000

(87) PCT Pub. No.: WO99/07707

PCT Pub. Date: Feb. 18, 1999

(30) Foreign Application Priority Data

Aug. 12, 1997 (HU) ............................................. 9701380
Aug. 12, 1997 (HU) ............................................. 9701381

(51) Int. Cl.⁷ ........................ A61K 31/55; A61D 25/08; C07D 243/00

(52) U.S. Cl. ........................................ 514/220; 540/557
(58) Field of Search ........................... 514/220; 540/557

(56) References Cited

FOREIGN PATENT DOCUMENTS

| | | |
|---|---|---|
| DE | A 3727226 | 2/1988 |
| DE | A 4428835 | 2/1996 |
| EP | A 0492485 | 7/1992 |
| EP | A 0699677 | 3/1996 |
| EP | A 0699678 | 3/1996 |
| FR | A 2566774 | 1/1986 |
| GB | A 2162184 | 1/1986 |
| WO | WO 92 11262 | 7/1992 |
| WO | WO 95 01357 | 1/1995 |
| WO | WO 97/28163 | * 8/1997 |

OTHER PUBLICATIONS

Anderson et al., J. Am. Chem. Soc., vol. 117, 1995, pp. 12358–12459.

Ling et al., Journal of the Chemical Society Perkin Transactions 1, No. 11, Jun. 7, 1995, pp. 1423–1428.

* cited by examiner

Primary Examiner—Brenda Coleman
(74) Attorney, Agent, or Firm—Birch, Stewart, Kolasch & Birch, LLP

(57) ABSTRACT

The disclosure relates to a novel 8-substituted-9H-1,3-dioxolo-[4,5-h][2,3]benzodiazepine compound of formula I and pharmaceutically acceptable quaternary ammonium salts thereof, a process for preparing the same, a pharmaceutical composition containing a 8-substituted-9H-1,3-dioxolo-[4,5-h][2,3]benzodiazepine compound, and a method of treatment using the pharmaceutical composition. A complete description of the compound of formula I is found in the specification. The compounds of the general formula I possess unique competitive AMPA/kainite antagonist properties making them useful in the treatment of diseases where inhibition of the AMPA/kainite receptors may a favorable effect.

14 Claims, No Drawings

8-SUBSTITUTED-9H-1,3-DIOXOLO/4,5-H//2,3/ BENZODIAZEPINE DERIVATIVES, AS AMPA/KAINATE RECEPTOR INHIBITORS

This application is the national phase under 35 U.S.C. §371 of PCT International Application No. PCT/HU98/00075 which has an International filing date of Aug. 7, 1998, which designated the United States of America.

The invention refers to novel 8-substituted-9H-1,3-dioxolo/4,5-h//2,3/-benzodiazepine derivatives, a pharmaceutical composition containing the same, and a process for the preparation of the active ingredient.

More specifically, the invention refers to novel 8-substituted-9H-1,3-dioxolo-/4,5-h//2,3/benzodiazepine derivatives of the formula I

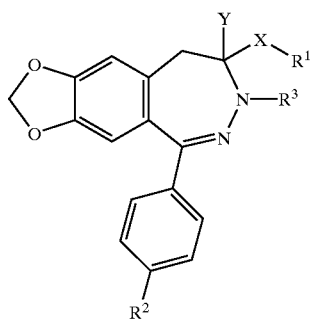

wherein
X represents a carbonyl group or a methylene group, and
$R^1$ stands for a hydrogen atom, a hydroxy group, a $C_{1-4}$ alkoxy group, a $C_{1-4}$ alkanoyloxy group, a ($C_{1-4}$ alkyl) sulfonyloxy group or a group of the formula —$NR^4R^5$, wherein
$R^4$ and $R^5$ mean, independently, a hydrogen atom, a $C_{1-4}$ alkoxy group, a $C_{1-4}$ alkanoyl group or a $C_{1-6}$ alkyl group which latter is optionally substituted by a saturated or unsaturated heterocyclic group having 5 or 6 members and comprising one or two nitrogen atom(s) or a nitrogen atom and an oxygen atom as the heteroatom, or by an N-/phenyl-($C_{1-4}$ alkyl)/-N-($C_{1-4}$ alkyl)amino group, wherein the phenyl group is optionally substituted by 1 to 3 substituent(s), wherein the substituent consists of a $C_{1-4}$ alkoxy group, or
$R^4$ and $R^5$ form with the adjacent nitrogen atom and optionally with a further nitrogen atom or an oxygen atom a saturated or unsaturated heterocyclic group having 5 to 10 members, or
X forms together with $R^1$ a cyano group, a tetrazolyl group, a group of the formula —CHNOH, or a group of the formula —$COR^6$, wherein
$R^6$ means a hydroxy group, a $C_{1-4}$ alkoxy group, a phenoxy group, a naphthyloxy group, or an amino group which latter is optionally substituted by a $C_{1-4}$ alkyl group,
$R^2$ stands for a nitro group, an amino group or a ($C_{1-4}$ alkanoyl)amino group,
$R^3$ represents a hydrogen atom, a $C_{1-4}$ alkyl group, or a group of the formula —$COR^7$, wherein
$R^7$ represents a hydrogen atom, a $C_{1-6}$ alkyl group, a $C_{1-6}$ alkyl group substituted by 1 to 3 halo atom(s), a $C_{1-4}$ alkoxy group, a phenoxy group, a pyridyl group, a phenyl group or a naphthyl group which two latter groups are optionally substituted by 1 to 3 substituent(s), or a group of the formula —$(CH_2)_n$—$NR^8R^9$, wherein
$R^8$ and $R^9$ represent, independently, a hydrogen atom, a $C_{1-4}$ alkyl group optionally substituted by a phenyl group or a saturated heterocyclic group having 5 or 6 members and containing a nitrogen group or a nitrogen and an oxygen group, and said phenyl group is optionally substituted by 1 to 3 substituent(s), wherein the substituent consists of a $C_{1-4}$ alkoxy group, or
$R^8$ and $R^9$ form, together with the adjacent nitrogen atom and optionally a further nitrogen or oxygen atom, a saturated or unsaturated hetero-cyclic group having 5 or 6 members and being optionally substituted by a phenyl group that is optionally substituted by 1 to 3 substituents, wherein the substituent consists of a halo atom or a $C_{1-4}$ alkoxy group,
n has a value of 0, 1 or 2,
Y is a hydrogen atom, or a methyl group, or
Y forms together with $R^3$ a valence bond between the carbon atom in position 8 and the nitrogen atom in position 7,
with the proviso that
1) if Y stands for a hydrogen atom or forms together with $R^3$ a valence bond and X represents a methylene group, then $R^1$ is other than a hydrogen atom, and
2) if Y stands for a hydrogen atom or a methyl group and $R^3$ represents a $C_{1-4}$ alkyl group or a group of the formula —$COR^7$, then X is other than a methylene group, and pharmaceutically suitable acid addition salts or quaternary ammonium derivatives thereof.

Several 2,3-benzodiazepine derivatives having biological activity are known.

Tofisopam i.e. 1-(3,4-dimethoxyphenyl)-5-ethyl-7,8-dimethoxy-4-methyl-5H-2,3-benzodiazepine having anxiolytic effect is known from HU-P No. 155 572 and GB-P No. 1 202 579, respectively. The known compound does not comprise the ring system 1,3-dioxolo-/4,5-h//2,3/benzodiazepine.

From HU-P No. 186 760, 7,8-dihydro-8-methyl-9H-1,3-dioxolo/4,5-h//2,3/benzodiazepine derivatives having effect on the central nervous system are known, among others. The known compounds are prepared by reducing the corresponding 8-methyl-9H-1,3-dioxolo-/4,5-h//2,3/benzodiazepine derivative.

Various substituted 8-methyl-9H-1,3-dioxolo/4,5-h//2,3/benzodiazepine derivatives are known from HU-P No. 191 698 and the corresponding GB-P No. 2 162 184. The known compounds have antiaggressive and anxiolytic activities.

A novel process for the preparation of partly new 8-methyl-9H-1,3-dioxolo/4,5-h/-/2,3/benzodiazepine derivatives having antiaggressive activity is known from HU-P No. 191 702. According to the novel process, the suitably substituted 2-acetonyl-4,5-methylenedioxybenzophenone is reacted with an excess of hydrazine hydrate.

Further 7,8-dihydro-8-methyl-9H-1,3-dioxolo/4,5-h//2,3/ benzodiazepine derivatives having antidepressant and antiparkinsonian activities are known from HU-P No. 206 719.

A physical form of (R)-7-acetyl-5-(4-aminophenyl)-8,9-dihydro-8-methyl-7H-1,3-dioxolo/4,5-h//2,3/benzodiazepine useful as an AMPA antagonist is described in EP No. 699 678.

7-Acyl-5-(4-aminophenyl)-8,9-dihydro-8-methyl-9H-1, 3-dioxolo/4,5-h//2,3/benzodiazepine derivatives having anticonvulsive and muscle-relaxant activity are known from EP No. 492 485.

Enantiomers of 7,8-dihydro-8-methyl-5-(4-nitrophenyl)-9H-1,3-dioxolo/4,5-h//2,3/-benzodiazepine are described in WO 95/01357. The known enantiomers are useful as intermediates in the synthesis of therapeutically active compounds.

In EP No. 699 677 a stereoselective process for producing known dihydro-2,3-benzodiazepine derivatives is described.

5-(4-Substituted phenyl)-8-methyl-9H-1,3-dioxolo/4,5-h//2,3/benzodiazepine derivatives are described in FR 2 566 774. The compounds have antiaggressive activity.

In J. Am. Chem. Soc., 117, 12358–9 (1995) an enantioselective synthesis for the preparation of 7-acetyl-5-(4-aminophenyl)-8-methyl-8,9-dihydro-7H-1,3-dioxolo/4,5-h/-/2,3/benzodiazepine is described.

7-Acyl-5-(4-aminophenyl)-8-alkyl-7H-1,3-dioxolo/4,5-h//2,3/benzodiazepines are described in DE-P No. 44 28 835. The known compounds inhibit the AMPA receptors.

An enantioselective synthesis for the preparation of 7-acyl-5-(4-aminophenyl)-8,9-dihydro-8-methyl-7H-1,3-dioxolo/4,5-h//2,3/-benzodiazepine derivatives is known from J. Chem. Sac. Perkin Trans I, 1995, 1423–1427.

Some of the 2,3-benzodiazepine derivatives elicit their effect through the non-competitive inhibition of the AMPA/kainate receptors /Donevan, S. D. et al., J. Pharmacol. Exp. Ther., 271, 25–29 (1994)/.

From the literature it is known that AMPA/kainate receptors play an important role in the acute and chronic diseases of the central nervous system. Through the inhibition of these receptors, muscle relaxant, neuro-protective and spasm inhibiting effects can be achieved /Vizi, E. S. et al., CNS Drug Reviews, 2, 91–126 (1996); Lees, G. L., CNS Drugs, 5, 51–74 (1996)/.

The aim of the invention is to prepare novel 2,3-benzodiazepine derivatives that are more effective than the known 2,3-benzodiazepine derivatives.

It was found that the above aim is achieved by the novel 8-substituted-9H-1,3-dioxolo/4,5-h//2,3/benzodiazepine derivatives which have—due to their non-competitive AMPA/kainate effect—considerable muscle relaxant, neuroprotective and anticonvulsive activities.

Thus, the novel compounds can be employed for the treatment of any diseases (such as epilepsy, diseases resulting in muscle spasm, various neurodegenerative diseases, stroke) in which the inhibition of the AMPA/kainate receptors is favourable.

In the description and Claims, in the definition of the substituents, under a $C_{1-4}$ alkoxy group primarily a methoxy, ethoxy, n-propoxy, isopropoxy or n-butoxy group, preferably a methoxy group is meant.

A $C_{1-4}$ alkyl group is a methyl, ethyl, n-propyl, isopropyl, n-butyl, sec.-butyl, tert.-butyl or isobutyl group. Preferably, a $C_{1-4}$ alkyl group is a methyl or an ethyl group.

A $C_{1-6}$ alkyl group can be, in addition to alkyl groups listed above, for example a n-pentyl, 2-methylbutyl, n-hexyl, 2,2-dimethylbutyl or 2,3-dimethylbutyl group etc.

A $C_{1-4}$ alkanoyl group is, primarily, a formyl, acetyl or n-propionyl group. Preferably, a $C_{1-4}$ alkanoyl group is an acetyl group.

Similarly, a $C_{1-4}$ alkanoyloxy group is, primarily, a formyloxy, acetyloxy or n-propionyloxy group.

Under a saturated or unsaturated heterocyclic group having 5 or 6 members and comprising one or two nitrogen atom(s) or a nitrogen atom and an oxygen atom as the heteroatom, for example a pyrrolidinyl, piperidinyl, piperazinyl, imidazolyl or morpholino group is meant. Suitably, the other nitrogen atom of the piperazinyl group is substituted.

When the substituents $R^4$ and $R^5$ form with the adjacent nitrogen atom a saturated or unsaturated heterocyclic group having 5 to 10 members, said heterocyclic group contains one or two nitrogen atom(s) or a nitrogen atom and an oxygen atom as the heteroatom, and it consists of one ring or two condensed rings. The heterocyclic ring(s) contain(s) no double bond or one or more double bond(s). The above heterocyclic group is for example a pyrrolidinyl, imidazolyl, piperidinyl, pyridyl, morpholino, piperazinyl or 1,5-diazabicyclo/4.3.0/non-5-enyl group. Suitably, one of the nitrogen atoms of the piperazinyl group is substituted.

Under a pharmaceutically suitable acid addition salt an acid addition salt formed with a pharmaceutically suitable inorganic acid such as hydrochloric acid, hydrobromic acid, sulfuric acid, phosphoric acid etc. or with a pharmaceutically suitable organic acid such as formic acid, acetic acid, fumaric acid, maleic acid, lactic acid, malic acid, tartaric acid, succinic acid, citric acid, methanesulfonic acid etc. is meant.

A quaternary ammonium derivative is a derivative wherein one of the nitrogen atoms of a compound of the formula I is present in a quaternerized form.

The invention includes any isomers of the compounds of the formula I and the mixtures thereof.

Under the isomers of the compounds of the formula I—due to the presence of at least one chiral centre both enantiomers, and—because of isomerisms that exist in case of certain substitutions—the isomers E and Z, diastereomers, tautomeric forms, and the mixtures thereof such as the racemate are meant.

A preferred subgroup of the compounds of the formula I consists of the 8-substituted-9H-1,3-dioxolo/4,5-h//2,3/benzodiazepine derivatives and pharmaceutically suitable acid addition salts and quaternary ammonium derivatives thereof, wherein in the formula I X represents a carbonyl group or a methylene group, and $R^1$ stands for a hydrogen atom, a hydroxy group, a methoxy group, an acetoxy group, a methylsulfonyloxy group or a group of the formula —$NR^4R^5$, wherein $R^4$ and $R^5$ mean, independently, a hydrogen atom, a methoxy group, an acetyl group or a $C_{1-4}$ alkyl group which latter is optionally substituted by a morpholino or a dimethoxyphenylethyl-N-(methyl) amino group, or $R^4$ and $R^5$ form with the adjacent nitrogen atom and optionally with a further nitrogen atom or an oxygen atom a saturated or unsaturated heterocyclic group having 5 to 9 members, or X forms together with $R^1$ a cyano group, a tetrazolyl group or a group of the formula —CHNOH, $R^2$ stands for a nitro group or an amino group, $R^3$ represents a hydrogen atom or an acetyl group, Y is a hydrogen atom, or Y forms together with $R^3$ a valence bond between the carbon atom in position 8 and the nitrogen atom in position 7.

with the proviso that 1) if Y stands for a hydrogen atom or forms together with $R^3$ a valence bond and X represents a methylene group, then $R^1$ is other than a hydrogen atom, and 2) if Y stands for a hydrogen atom or a methyl group and $R^3$ represents a $C_{1-4}$ alkyl group pr a group of the formula —$COR^7$, then X is other than a methylene group.

Within the above subgroup, especially preferred compounds of the invention consist of the following 8-substituted-9H-1,3-dioxolo-/4,5-h//2,3/benzodiazepine derivatives and pharmaceutically suitable acid addition salts and quaternary ammonium derivatives thereof: 5-(4-aminophenyl)-9H-1,3-dioxolo/4,5-h//2,3/-benzodiazepine-8-carboxylic amide, 5-(4-aminophenyl)-8-cyano-9H-1,3-dioxolo-/4,5-h//2,3/benzodiazepine, 5-(4-aminophenyl)-8-(5-tetrazolyl)-9H-1,3-dioxolo/4,5-h//2,3/benzodiazepine.

A further preferred subgroup of the compounds of the invention consists of the 8-substituted-9H-1,3-dioxolo/4,5-h//2,3/-benzodiazepine derivatives of the formula I, wherein
  $R^3$ represents a hydrogen atom or a group of the formula —$COR^7$, wherein
    $R^7$ stands for a hydrogen atom, a $C_{1-4}$ alkyl group, a $C_{1-4}$ alkyl group substituted by 1 to 3 halo atom(s), or a group of the formula —$(CH_2)_n$—$NR^8R^9$, wherein
      $R^8$ and $R^9$ mean, independently, a hydrogen atom, a $C_{1-4}$ alkyl group optionally substituted by a phenyl group or a morpholino group, and the phenyl group is optionally substituted by one or two methoxy group(s), or
      $R^8$ and $R^9$ form, together with the adjacent nitrogen atom and optionally a further nitrogen or oxygen atom a saturated or unsaturated hetero-cyclic group having 5 or 6 members. and being optionally substituted by a phenyl group that is optionally substituted by a halo atom or a methoxy group,
      n has a value of 0, 1 or 2,
  X forms together with $R^1$ a cyano group or a group of the formula —$COR^6$, wherein
    $R^6$ represents a hydroxy group or an amino group,
  Y stands for a methyl group,
  $R^2$ is a nitro group, an amino group, or a ($C_{1-4}$ alkanoyl) amino group,
and pharmaceutically suitable acid addition salts thereof.

Within the above subgroup, suitable compounds of the invention consist of the 8-substituted-9H-1,3-dioxolo/4,5-h//2,3/-benzodiazepine derivatives of the formula I, wherein
  $R^3$ represents a hydrogen atom or a group of the formula —$COR^7$, wherein
    $R^7$ stands for a hydrogen atom, a $C_{1-4}$ alkyl group, a $C_{1-2}$ alkyl group substituted by a chloro atom, a trifluoromethyl group, a trichloromethyl group or a group of the formula —$(CH_2)_n$—$NR^8R^9$, wherein
      $R^8$ and $R^9$ represent, independently, a hydrogen atom, a $C_{1-2}$ alkyl group optionally substituted by a phenyl group or a morpholino group, and the phenyl group is optionally substituted by two methoxy groups, or
      $R^8$ and $R^9$ form, together with the adjacent nitrogen atom and optionally a further nitrogen or oxygen atom a pyridinyl, pyrrolidinyl, morpholino or piperazinyl group, wherein the piperazinyl group is substituted by a fluorophenyl or a methoxyphenyl group,
      n has a value of 0, 1 or 2,
  X forms together with R a cyano group,
  $R^2$ means an amino group or a ($C_{1-4}$ alkanoyl)-amino group,
  Y stands for a methyl group,
and pharmaceutically suitable acid addition salts thereof.

Especielly preferred compounds of the invention consist of the 8-substituted-9H-1,3-dioxolo/4,5-h//2,3/ benzodiazepine derivatives of the formula I, wherein
  $R^2$ represents an acetylamino or a propionyl-amino group,
  $R^1$, $R^3$, X and Y are as defined in claim 5,
and pharmaceutically suitable acid addition salts thereof.

The 8-substituted-9H-1,3-dioxolo-/4,5-h//2,3/benzodiazepine derivatives of the invention are prepared by the following methods:

a) for the preparation of 8-formyl-5-(4-nitrophenyl)-9H-1,3-dioxolo/4,5-h//2,3/-benzodiazepine of the formula II

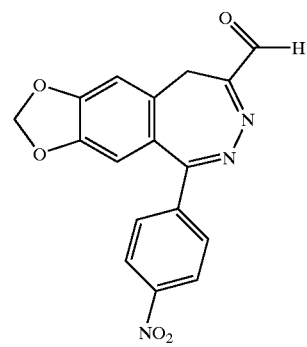

being within the scope of the compounds of the formula I, 8-methyl-5-(4-nitrophenyl)-9H-1,3-dioxolo/4,5-h//2,3/benzodiazepine is reacted with an oxidizing agent; or b) for the preparation of 5-(4-nitrophenyl)-9H-1,3-dioxolo/4,5-h//2,3/benzodiazepine-8-carboxylic acid of the formula III

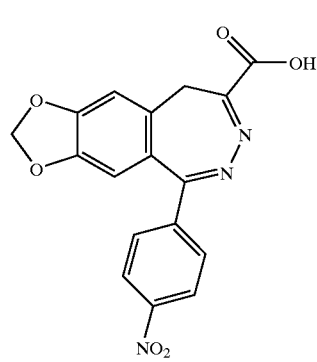

being within the scope of the compounds of the formula I, 8-formyl-5-(4-nitrophenyl)-9H-1,3-dioxolo/4,5-h//2,3/benzodiazepine of the formula II is reacted with an oxidizing agent; or c) for the preparation of compounds of the formula I, wherein $R^1$ is an imidazolyl group, $R^2$ represents a nitro group, X stands for a carbonyl group, and Y forms together with $R^3$ a valence bond, 5-(4-nitrophenyl)-9H-1,3-dioxolo/4,5-h//2,3/benzodiazepine-8-carboxylic acid of the formula III is reacted with 1,1'-carbonyldiimidazole; or d) for the preparation of compounds of the formula I, wherein $R^1$ is a group of the formula —$NR^4R^5$, $R^2$ represents a nitro group, X stands for a carbonyl group, Y forms together with $R^3$ a valence bond, $R^4$ and $R^5$ are as defined in connection with the formula I, 5-(4-nitrophenyl)-9H-1,3-dioxolo/4,5-h//2,3/-benzodiazepine-8-carboxylic acid of the formula III or a reactive derivative thereof of the formula IV

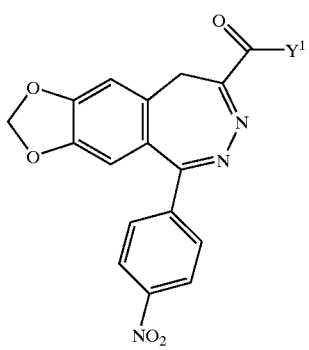

IV wherein $Y^1$ is a leaving group, is reacted with an amine of the formula V

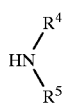

V wherein $R^4$ and $R^5$ are as stated above; or e) for the preparation of compounds of the formula I, wherein $R^1$ is a $C_{1-4}$ alkoxy group, $R^2$ represents a nitro group, X stands for a carbonyl group, Y forms together with $R^3$ a valence bond, 5-(4-nitrophenyl)-9H-1,3-dioxolo/4,5-h//2,3/benzodiazepine-8-carboxylic acid of the formula III is esterified with a $C_{1-4}$ alkanol; or f) for the preparation of compounds of the formula I, wherein $R^1$ is a ($C_{1-4}$ alkyl)sulfonyloxy group, $R^2$ represents a nitro group, X stands for a methylene group, Y forms together with $R^3$ a valence bond, 8-formyl-5-(4-nitrophenyl)-9H-1,3-dioxolo/4,5-h//2,3/benzodiazepine of the formula II is reacted with a reducing agent, and the 8-(hydroxymethyl)-5-(4-nitrophenyl)-9H-1,3-dioxolo/4,5-h//2,3/-benzodiazepine obtained is reacted with a ($C_{1-4}$ alkyl) sulfonyl halide; or g) for the preparation of compounds of the formula I, wherein $R^1$ represents a $C_{1-4}$ alkoxy group, a $C_{1-4}$ alkanoyloxy group or a group of the formula —$NR^4R^5$, $R^2$ stands for a nitro group, Y forms together with $R^3$ a valence bond, $R^4$ and $R^5$ are as stated in connection with formula I, 8-formyl-5-(4-nitrophenyl)-9H-1,3-dioxolo/4,5-h//2,3/benzodiazepine of the formula II is reacted with a reducing agent, and the 8-(hydroxymethyl)-5-(4-nitrophenyl)-9H-1,3-dioxolo/4,5-h//2,3/-benzodiazepine obtained or a reactive alkylating derivative thereof of the formula VI

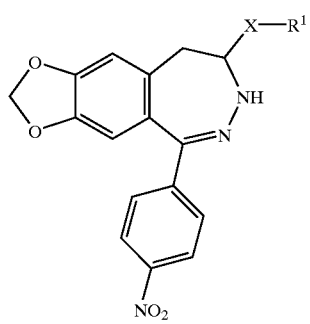

VI wherein Q stands for a leaving group, is reacted with a $C_{1-4}$ alkanol, a $C_{1-4}$ alkanecarboxylic acid or a reactive acylating derivative thereof or an amine of the formula V, wherein $R^4$ and $R^5$ are as stated above; or h) for the preparation of a compound of the formula I, wherein X forms together with $R^1$ a group of the formula —CHNOH, $R^2$ represents a nitro group, Y forms together with $R^3$ a valence bond, 8-formyl-5-(4-nitrophenyl)-9H-1,3-dioxolo/4,5-h//2,3/benzodiazepine of the formula II is reacted with hydroxylamine; or i) for the preparation of a compound of the formula I, wherein X forms together with $R^1$ a cyano group, $R^2$ represents a nitro group, Y forms together with $R^3$ a valence bond, 8-(hydroxyiminomethyl)-5-(4-nitrophenyl)-9H-1,3-dioxolo/4,5-h//2,3/benzodiazepine is reacted with a dehydrating agent; or j) for the preparation of a compound of the formula I, wherein X forms together with $R^1$ a tetrazolyl group, $R^2$ represents a nitro group, Y forms together with $R^3$ a valence bond, 8-cyano-5-(4-nitrophenyl)-9H-1,3-dioxolo/4,5-h//2,3/benzodiazepine is reacted with an alkaline metal azide; or k) for the preparation of 7,8-dihydro compounds of the formula VI being a narrower group of the compounds of the formula I, wherein X represents a carbonyl group or a methylene group, and $R^1$ is as defined in connection with formula I, a compound of the formula VII

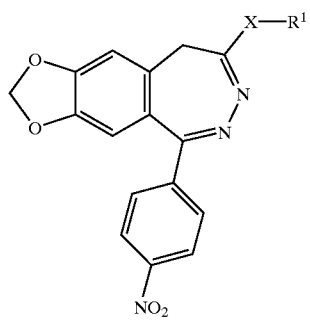

VII wherein X and R are as stated above, is reacted with a reducing agent; or l) for the preparation of 7,8-dihydro-7-acyl derivatives of the formula VIII

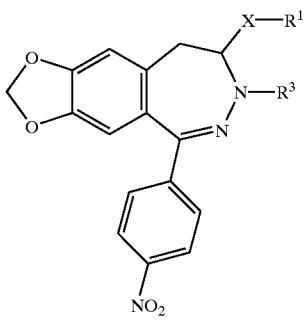

VIII being a narrower group of the compounds of the formula I, wherein X represents a carbonyl group or a methylene group, $R^1$ is as stated in connection with formula I, $R^3$ stands for a $C_{1-4}$ alkanoyl group, a 7,8-dihydro derivative of the formula VI, wherein X and $R^1$ are as defined above, is reacted with a $C_{1-4}$ alkanecarboxylic acid or a reactive acylating derivative thereof; or m) for the preparation of compounds of the formula I, wherein $R^1$ is a group of the formula —$NR^4R^5$, $R^2$ represents a nitro group, X stands for a carbonyl group or a methylene group, one of $R^4$ and $R^5$ represents a $C_{1-4}$ alkanoyl group, while the other is as defined in connection with formula I, Y means a hydrogen atom and in this case $R^3$ stands for a $C_{1-4}$ alkanoyl group, or Y forms together with $R^3$ a valence bond, a compound of the formula I, wherein $R^1$ is a group of the formula —$NR^4R^5$, wherein one of $R^4$ and $R^5$ means a hydrogen atom, while the other is as defined above, X, $R^2$, Y and $R^3$ are as stated above, is reacted with a $C_{1-4}$ alkanecarboxylic acid or a reactive acylating derivative thereof;

n) for the preparation of compounds of the formula I, wherein Y represents a methyl group, —X—$R^1$ stands for a cyano group, $R^3$ is a hydrogen atom, and $R^2$ means a nitro group, the compound of the formula IX

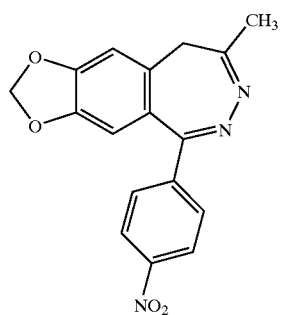

IX is reacted with hydrogen cyanide; or o) for the preparation of compounds of the formula I, wherein Y represents a methyl group, $R^3$ stands for a hydrogen atom, $R^2$ means a nitro group and —X—$R^1$ represents a group of the formula —$COR^6$, wherein $R^6$ is as defined in connection with the formula I, the compound of the formula X

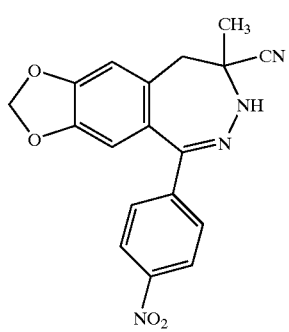

X is hydrolyzed with a mineral acid, and the carboxylic acid obtained is optionally converted to an ester or a carboxylic amide; or p) for the preparation of compounds of the formula I, wherein Y represents a methyl group, —X—$R^1$ stands for a cyano group or a group of the formula —$COR^6$, $R^2$ means a nitro group, $R^3$ is a $C_{1-4}$ alkyl group, and $R^6$ is as defined in connection with the formula I, a compound of the formula I, wherein Y, —X—$R^1$ and $R^2$ are as stated above, $R^3$ represents a hydrogen atom, is reacted with a ($C_{1-4}$ alkyl)halide; or r) for the preparation of compounds of the formula I, wherein Y represents a methyl group, —X—$R^1$ stands for a cyano group or a group of the formula —$COR^6$, $R^2$ means a nitro group, $R^3$ is a group of the formula —$COR^7$, $R^7$ represents a group of the formula —$(CH_2)_n$——$NR^8R^9$, $R^6$, $R^8$, $R^9$ and n are as defined in connection with the formula I, a compound of the formula XI

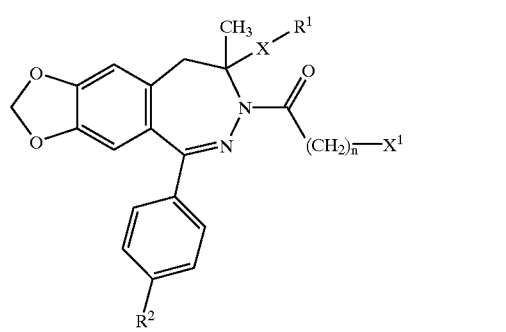

XI wherein —X—$R^1$, $R^2$ and n are as stated above, $X^1$ is a leaving group, preferably a chloro atom, is reacted with an amine of the formula $HNR^8 R^9$;

and, if desired, an obtained compound of the formula I, wherein $R^2$ represents a nitro group, $R^1$, $R^3$, X and Y are as defined in connection with formula I, is transformed into a compound of the formula I, wherein $R^2$ represents an amino group, by reduction;

and, if desired, an obtained compound of the formula I, wherein $R^2$ represents an amino group, $R^1$, $R^3$, X and Y are as stated in connection with formula I, is reacted with a $C_{1-4}$ alkanecarboxylic acid or a reactive acylating derivative thereof;

and, if desired, an obtained base of the formula I is converted to a pharmaceutically suitable acid addition salt or liberated from the acid addition salt;

and, if desired, an obtained compound of the formula I or pharmaceutically suitable acid addition salt thereof is converted to a quaternary ammonium derivative.

In process a) of the invention, the reaction is performed in a manner known in itself in the preparation of aldehydes /Houben-Weyl: Methoden der Organischen Chemie, Aldehyde, Band E3, Georg Thieme Verlag, Stuttgart, 1983/.

A preferred oxidizing agent is selenium(IV) oxide.

In process b) of the invention, the reaction is conducted in a manner known in itself in the preparation from carboxylic acids from aldehydes /Houben-Weyl: Methoden der Organischen Chemie, Carbonsaure-Derivate, Band E5, Georg Thieme Verlag, Stuttgart, 1985; Saul Patai: The chemistry of acid derivatives, John Wiley and Sons, New York/.

In processes c), d) and e) of the invention, the reactions are carried out in a manner known in itself in the transformations of carboxylic acids /Houben-Weyl: Methoden der Organischen Chemie, Carbonsaure und Carbonsaure-Derivate, Band E5, Georg Thieme Verlag, Stuttgart, 1985/.

In processes f) and g) of the invention, the reactions are performed in a manner known in itself in the transformation of oxo compounds to alcohols /Houben-Weyl: Methoden der Organischen Chemie, Alkohole, Band VI, Georg Thieme Verlag, Stuttgart, 1979/. The hydroxy compound formed is reacted also in a manner known in itself with an alkylsulfonyl halide, preferably methylsulfonyl chloride in case of process f); in case of process g), the alkylsulfonyl ester of the hydroxy compound is reacted with an amine or the hydroxy compound is acylated for example with the corresponding alkanecarboxylic anhydride.

In processes h), i) and j) of the invention, the reactions arre carried out in a manner known in itself in the transformations of oxo compounds /Houben-Weyl: Methoden der Organischen Chemie, Carbonsaure und Carbonsaure-Derivate, Band E5, Georg Thieme Verlag, Stuttgart, 1985; Houben Weyl: Methoden der Organischen Chemie, Heterane, Band III, part 4, Georg Thieme Verlag, Stuttgart, 1994/.

In process k) of the invention, the reduction is performed in a manner known in itself /Houben-Weyl: Methoden der organischen Chemie, Band IV, Reduction, Georg Thieme Verlag, Stuttgart, 1989/.

In processes f), g) and k) of the invention, the reducing agent is preferably sodium tetrahydroborate.

It is to be noted that in case of reducing a compound of the formula I, wherein X represents a carbonyl group, Y forms together with $R^3$ a valence bond, $R^2$ stands for a nitro group, using an equimolar amount of sodium tetrahydroborate, only the carbonyl group is reduced. In the presence of a large excess of sodium tetrahydroborate, in addition to the reduction of the carbonyl group, the double bond between the ring nitrogen in position 7 and the ring carbon atom in position 8 becomes saturated, too.

In processes l) and m) of the invention, the acylation reactions are carried out, in general, using a reactive acylating derivative of the $C_{1-4}$ alkanecarboxylic acid such as acid halide, acid anhydride or an active ester, at a temperature from −20 to +150° C. preferably in the presence of an acid binding agent and/or pyridine, in the presence or absence of an organic solvent /Houben-Weyl: Methoden der Organischen Chemie, Carbonsaure und Carbonsaure-Derivate, Band E5, Georg Thieme Verlag, Stuttgart, 1985; S. Patai: The chemistry of amides, Interscience Publishers, 1970/.

In process n) of the invention, the reaction of the compound of the formula IX and hydrogen cyanide is carried out in a manner known from the literature /Houben-Weyl: Methoden der organischen Chemie, Band VIII, Georg Thieme Verlag, Stuttgart/.

The 8-methyl-9H-1,3-dioxolo/4,5-h//2,3/-benzodiazepine derivative of the formula IX can be prepared by a method that is analogous with the process described in HU-P No. 191 702.

In process o) of the invention, the cyano group of the compound of the formula X can be hydrolized in a manner known in itself, preferably in the presence of a mineral acid /S. Patai: The chemistry of the cyano group/.

In process p) of the invention, the nitrogen atom in position 8 of the compound of the formula I can be acylated in a manner known in itself, in general, with an acid chloride, an acid anhydride or a chlorocarbonate ester, optionally in the presence of an acid binding agent, in the presence or absence of a solvent, at a temperature from −20 to +150° C.

For the preparation of carbamoyl derivatives, the acylated derivative obtained by using an active chlorocarbonate ester is reacted with an amino compound, or a compound of the formula I, wherein R represents a hydrogen atom, is reacted directly with the corresponding isocyanate.

In process r) of the invention, compounds of the formula I, wherein the carbon atom in position 8 is substituted by a group of the formula —CO—$(CH_2)_n$—$NR^4R^5$, can be suitably prepared by reacting the corresponding compound of the formula XI, wherein $R^1$, $R^2$ and n are as stated in connection with formula I, X stands for a leaving group, preferably a chloro atom, with an amine of the formula $HNR^4R^5$, wherein $R^4$ and $R^5$ are as defined in connection with formula I. The compound of the formula XIcan be prepared by acylating a compound of the formula I, wherein R means a hydrogen atom. The reactions given above are performed in a manner known from the art /Houben-Weyl: Methoden der Organischen Chemie, Band XI, G. Thieme Verlag, Stuttgart, 1957; S. Patai: The chemistry of amino group, Interscience Publishers, 1968/.

The nitro group of the compounds of the formula I can be converted to an amino group by reduction in a manner known in itself. The reduction can be performed for example with tin(II) chloride or in the presence of a catalyst using a hydrogen source. For example, the catalyst is Raney nickel, palladium or platinum oxide, the hydrogen source consists of, for example, gaseous hydrogen, hydrazine, hydrazine hydrate, formic acid, trialkylammonium formate or an alkali metal formate.

In case of compounds of the formula I, wherein $R^2$ represents an amino group, the latter group can be acylated with a $C_{1-4}$ alkanecarboxylic acid in a manner known in itself. The acylation reaction can be performed by the method described in connection with processes l) and m).

If desired, a base of the formula I is reacted with an inorganic or organic acid to transform it into a pharmaceutically suitable acid addition salt, or the base of the formula I is liberated from the acid addition salt using a stronger base.

The pharmacological effect of the novel compounds of the formula I was studied by in vitro and in vivo methods. 8-Methyl-5-(4-aminophenyl)-9H-1,3-dioxolo/4,5-h/-/2,3/ benzodiazepine (compound "A") known from HUP No. 191 698 and GB-P No. 2 162 184 was used as the reference substance.

In vitro Determination of AMPA Antagonist Effect

QNTI (inhibition of quisqualate neurotoxicity (test)

The method is based on the phenomenon that the neurotixic effect of quisqualate /i.e. (S)-alpha-amino-3,5-dioxo-1,2,4-oxadiazolidine-2-propanoic acid, an AMPA/kainate agonist/ on the primer telencephalic cell culture of the rat could be inhibited by AMPA/kainate antagonists. The test was performed as described in the literature /Kovács, A. D., Egyed, A.: Protection against non-NMDA receptor-mediated excitotoxicity by GYKI 52466 in mature telencephalic cultures of the rat, Neurobiology, 4, 59–72 (1996)/. The $IC_{50}$ values obtained are shown in Table I.

PSI (inhibition of population spike) test

The field potentials (population spike) evoked by electric stimulation of the Shaffer collateral comissural pathway were measured in the CAl neurones of rat hippocampus. The population spike can be inhibited by AMPA/kainate antagonists. The non-cumulative $IC_{50}$ values are shown in Table I. /Tarnawa, I., Molnár, P., Gaál, L., Andrási, F.: Inhibition of hippocampal field potentials by GYKI 52466 in vitro and in vivo, Acta Physiol. Hung., 79(2), 163–9 (1992)/.

SD (spreading depression) test

The method is based on the phenomenon of spreading depression evoked by kainate in isolated retinal preparation of the chicken. The formation of spreading depression is inhibited (delayed) by AMPA/kainate antagonists. /Sheardown M. J.: The triggering of spreading depression in the chicken retina: a pharmacological study, Brain Res., 607(1–2), 189–194 (1993)/. The obtained $IC_{50}$ values are shown in Table I.

TABLE I

IC$_{50}$ values of the compounds examined in various in vitro AMPA antagonist tests

| Compound (No. of Example) | QNTI[a] IC$_{50}$ | PSI[b] in micromole | SD[c] |
|---|---|---|---|
| 48 | no data | | 6.1 |
| 73 | 7.4 | 6.3 | 6.7 |
| 89 | 5.4 | 3.0 | 3.7 |
| "A" | 12.0 | 9.1 | 9.5 |

[a]Inhibition of quisqualate neurotoxicity in primer cortical culture.
[b]Inhibition of population spike.
[c]Spreading depression test.

As shown in Table I, the inhibitory effects of the novel compounds are significantly higher than that of reference compound "A".

In vivo Assays

Acute toxicity

The study was done in NMRI mice of both sexes, weighing 20 to 25 g, with 6 animals in each dose-group. The test compounds were applied at 20 mg/kg volume, and the maximal per os and ip. doses were 500 mg/kg and 300 mg/kg, respectively. The cumulative lethality was recorded on day 7. The animals were kept under standard laboratory conditions. The LD$_{50}$ values obtained are shown in Table II.

TABLE II

Acute toxicity in mg/kg

| Compound (No. of Example | Appr- LD$_{50}$ ip. | Appr. LD$_{50}$ p.o. |
|---|---|---|
| 73 | about 300 | higher than 500 |
| 89 | about 300 | higher than 500 |
| "A" | 392 | 500 |

Muscle relaxant effect

The assay was done according to Hoppe in male NMRI mice weighing 20 to 25 g, with 10 animals in each group /Hoppe, J. O., J. Pharmacol. Exp. Ther., 100, 333 (1950)/. Following the ip. treatment of animals, the number of mice showing muscle weakness were recorded at every 10 minutes in the first hour and at half hour intervals afterwards. The animals falling off the 60° inclined screen within 30 seconds were considered positive. ED$_{50}$ values of the given compounds were determined at each time. The duration of effect was defined as the time of last reading when the effect was at least 30%. The results obtained are summarized in Table III.

TABLE III

Muscle relaxant effect

| Compound (No. of Example) | ED$_{50}$[x] ip. in mg/kg | duration in hr |
|---|---|---|
| 73 | 22.6 | higher than 4 |
| 89 | 31.3 | 1 |
| "A" | 24.5 | 1 |

[x]determined at the time of maximal effect.

Although the toxicity and muscle relaxant activity of the novel compounds are similar to that of reference compound "A", the duration of the muscle relaxant effect for Example 73 is substantially longer as shown in Table III.

Maximal electroshock test (MES)

Male NMRI mice weighing 20 to 30 g were used for the method of Swinyard et al. /Swinyard, E. A., Brown, W. C. and Goodman, L.S.: Comparative assays of antiepileptic drugs in mice and rats, J. Pharmacol., 106, 319 (1952)//. The animals—10 in each group—were treated ip. either with various doses of the test substance or with vehicle. After 30 minutes, a 50 Hz, 40 mA electroshock was applied for 0.4 s through corneal electrodes. The number of animals that developed tonic extensor convulsion of the hind-limbs was registered, percent inhibition was calculated, and ED$_{50}$ values were determined by the method of Litchfield and Wilcoxon /Litchfield, J. T., Wilcoxon, F. A.: A simplified method of evaluating dose-effect experiments, J. Pharmacol. Exp. Ther., 96, 99 (1949)/ and summarized in Table IV.

Audiogenic seizure (AS) test

The experiments were carried out by the slightly modified method of De Sarro et al. /De Sarro, G. B., Croucher, M. J. and Meldrum, B. S.: Anticonvulsant action of DS 103–282, Neuropharm., 23, 525 (1984)/. Groups of 8 male DBA/2j strain mice weighing 7 to 14 g were treated ip. with the test substance in 10 ml/kg volume. 15 minutes later, the animals were placed into a covered glass container (30 cm in diameter) and exposed to a 14 kHz 120 dB tone for 60 s at the most. Seizure response was assessed using the following scale: 0=normal behaviour, 1=wild running, 2=clonus, 3=tonic flexor seizure, 4=tonic extensor seizure. The maximum response during the 60 s exposure was recorded for each animal. Lethality was also noted. The ED$_{50}$ values were determined by the method of Litchfield and Wilcoxon concerning the inhibition of clonic seizures and tonic extensor convulsions. The results are summarized in Table IV.

TABLE IV

Anticonvulsant effect following ip. treatment

| Compound (No. of Example) | MES[x] ED$_{50}$ n mg/kg | AS[xx] convulsion tonic | clonic |
|---|---|---|---|
| 32 | 2.5 | no data | |
| 73 (HCl) | <8.0 | 3.7 | 4.6 |
| 89 | 2.3 | 1.2 | 5.4 |
| "A" | 6.9 | 3.6 | 4.3 |

[x]Inhibition of maximal electroshock.
[xx]Inhibition of sound induced seizure.
The compound according to Example 89 was significantly more effective at the inhibition of maximal electroshock and sound induced tonic convulsions than the reference compound "A" as shown in Table IV.

Global Ischemia Induced by Magnesium Chloride

The experiments were carried out as described by Berga et al. /Berga, P., Beckett, P. R., Roberts, D. J., Llenas, J., Massingham, R.: Synergistic interactions between piracetam and dihydroergocristine in some animal models of cerebral hypoxia and ischemia, Arzneim.-Forsch., 36, 1314–1320 (1986)/. Groups of 10 male NMRI mice weighing 20 to 25 g were treated ip. with the test substance in 10 mg/kg volume. After 30 minutes, saturated aqueous magnesium chloride solution was applied iv. (5 ml/kg) resulting in an immediate cardiac arrest. The elapsed time between the iv. injection and the last gasping was measured (gasping time). The means of the treated groups were expressed as percent of control. Statistical analysis was done by ANOVA followed by DUNCAN test. The dose resulting in 50% descrease in gasping time (ID$_{50}$) was calculated by linear regression. The results are shown in Table V.

TABLE V

Increase in gasping time in the magnesium chloride induced global ischemia test in mice

| Compound (No. of Example) | Dose in mg/kg ip. | Effect in % | $ID_{50}$ in mg/kg ip. |
|---|---|---|---|
| 47 | 30 | 89 | 15 |
| 73 (HCl) | 30 | 66 | 19 |
| 89 | 30 | 117 | 7 |
| "A" | 30 | 55 | 30 |

From Table V it is apparant that the $ID_{50}$ values of the novel compounds of the formula I are significantly lower than that of the reference compound. It is clearly shown that the same extent of neuroprotection can be achieved by significantly lower doses of the novel compounds than that of the reference compound.

Thus, the novel 8-substituted-9H-1,3-dioxolo/4,5-h//2,3/ benzodiazepine derivatives of the formula I can be used as active ingredients of pharmaceutical compositions.

On the basis of the above test results, the novel compounds of the invention—due to their competitive AMPA/kainate antagonist property—have considerable muscle relaxant, neuroprotective and anticonvulsive effects. Consequently, the novel compounds can be used for the treatment of any disease such as epilepsy, diseases resulting in muscle spasm, neurodegenerative diseases, states after stroke, migraine and vomiting, wherein the inhibition of the AMPA/kainate receptors may have a favourable effect.

Moreover, the acute toxicity of the compounds of the formula I is essentially lower than that of the most efficient known AMPA/kainate antagonist 2,3-benzodiazepines. This property renders a significant therapeutical advantage, in contrast to the known compounds, in the treatment of clinical pictures listed above.

The pharmaceutical compositions of the invention contain a therapeutically active amount of the compound of the formula I or a pharmaceutically suitable acid addition salt or quaternary ammonium derivative thereof and one or more conventional carrier(s).

The pharmaceutical compositions of the invention are suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethyleneglycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propyleneglycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical compositions of the invention contain, in general, 0.1 to 95.0 per cent by mass of a compound of the formula I or a pharmaceutically suitable acid addition salt or quaternary ammonium derivative thereof. A typical dose for adult patients amounts to 0.1 to 20 mg of the compound of the formula I or a pharmaceutically acceptable acid addition salt or quaternary ammonium derivative thereof, daily. The above dose can be administered in one or more portions. The actual dosage depends on many factors and is determined by the doctor.

The pharmaceutical compositions of the invention are prepared by admixing a compound of the formula I or a pharmaceutically acceptable acid addition salt or quaternary ammonium derivative thereof to one or more carrier(s), and converting the mixture obtained to a pharmaceutical composition in a manner known per se. Useful methods are known from the literature, e.g. Remington's Pharmaceutical Sciences.

A preferred subgroup of the pharmaceutical compositions of the invention contains a 8-substituted-9H-1,3-dioxolo/4,5-h//2,3/-benzodiazepine derivative or a pharmaceutically suitable acid addition salt or quaternary ammonium derivative thereof, wherein X represents a carbonyl group or a methylene group, and $R^1$ stands for a hydrogen atom, a hydroxy group, a methoxy group, an acetoxy group, a methylsulfonyloxy group or a group of the formula —$NR^4R^5$, wherein
$R^4$ and $R^5$ mean, independently, a hydrogen atom, a methoxy group, an acetyl group or a $C_{1-4}$ alkyl group which latter is optionally substituted by a morpholino or an N-(dimethoxyphenylethyl)-N-(methyl)amino group, or
$R^4$ and $R^5$ form with the adjacent nitrogen atom and optionally with a further nitrogen atom or an oxygen atom a saturated or unsaturated heterocyclic group having 5 to 9 members, or X forms together with $R^1$ a cyano group, a tetrazolyl group or a group of the formula —CHNOH, $R^2$ stands for a nitro group or an amino group, $R^3$ represents a hydrogen atom or an acetyl group, Y is a hydrogen atom, or Y forms together with $R^3$ a valence bond between the carbon atom in position 8 and the nitrogen atom in position 7, as the active ingredient.

Within the above preferred subgroup of the invention, the suitable pharmaceutical compositions contain one of the following compounds:

5-(4-aminophenyl)-9H-1,3-dioxolo/4,5-h//2,3/-benzodiazepine-8-carboxylic amide,
5-(4-aminophenyl)-8-cyano-9H-1,3-dioxolo-/4,5-h//2,3/benzodiazepine,
5-(4-aminophenyl)-8-(5-tetrazolyl)-9H-1,3-dioxolo/4,5-h//2,3/benzodiazepine, or a pharmaceutically suitable acid addition salt or a quaternary ammonium derivative thereof as the active ingredient.

A further preferred subgroup of the pharmaceutical compositions of the invention contains a compound of the formula I, wherein
$R^3$ represents a hydrogen atom or a group of the formula —$COR^7$, wherein
$R^7$ stands for a hydrogen atom, a $C_{1-4}$ alkyl group, a $C_{1-4}$ alkyl group substituted by 1 to 3 halo atom(s), or a group of the formula —$(CH_2)_n$—$NR^8R^9$, wherein $R^8$ and $R^9$ mean, independently, a hydrogen atom, a $C_{1-4}$ alkyl group optionally substituted by a phenyl group or a morpholino group, and the phenyl group is optionally substituted by one or two methoxy group(s), or $R^8$ and $R^9$ form, together with the adjacent nitrogen atom and optionally a further nitrogen or oxygen atom a saturated or unsaturated hetero-cyclic group having 5 or 6 members and being optionally substituted by a phenyl group that is optionally substituted by a halo atom or a methoxy group, n has a value of 0, 1 or 2, X forms together with $R^1$ a cyano group or a group of the formula —$COR^6$, wherein $R^6$ represents a hydroxy group or an amino group, Y stands for a methyl group, $R^2$ is a nitro group, an amino group, or a ($C_{1-4}$ alkanoyl) amino group, or a pharmaceutically suitable acid addition salt thereof as the active ingredient.

Within the latter subgroup, especially preferred pharmaceutical compositions of the invention contain a compound of the formula I, wherein $R^3$ represents a hydrogen atom or a group of the formula —$COR^7$, wherein $R^7$ stands for a hydrogen atom, a $C_{1-4}$ alkyl group, a $C_{1-2}$ alkyl group substituted by a chloro atom, a trifluoromethyl group, a trichloromethyl group or a group of the formula —$(CH_2)_n$—$NR^8R^9$, wherein $R^8$ and $R^9$ represent, independently, a hydrogen atom, a $C_{1-2}$ alkyl group optionally substituted by a phenyl group or a morpholino group, and the phenyl group is optionally substituted by two methoxy groups, or $R^8$ and $R^9$ form, together with the adjacent nitrogen atom and optionally a further nitrogen or oxygen atom a pyridinyl, pyrrolidinyl, morpholino or piperazinyl group, wherein the piperazinyl group is substituted by a fluorophenyl or a methoxyphenyl group, n has a value of 0, 1 or 2, X forms together with $R^1$ a cyano group, $R^2$ means an amino group or a ($C_{1-4}$ alkanoyl)amino group, Y stands for a methyl group, or a pharmaceutically suitable acid addition salt thereof as the active ingredient.

Furthermore, the invention refers to a method of pharmaceutical treatment which comprises administering a therapeutically effective non-toxic amount of a 8-substituted-9H-1,3-dioxolo/4,5-h//2,3/benzodiazepine derivative of the formula I or a pharmaceutically suitable acid addition salt or quaternary ammonium derivative thereof to a patient suffering from especially epilepsy or a neurodegenerative disease or being in a state after stroke.

The invention includes also a process for the preparation of a pharmaceutical composition suitable for the treatment of especially epilepsy or a neurodegenerative disease or a state after stroke in which a 8-substituted-9H-1,3-dioxolo/ 4,5-h/-/2,3/benzodiazepine derivative of the formula I or a pharmaceutically suitable acid addition salt or a quaternary ammonium derivative thereof is converted to a pharmaceutical composition using one or more carrier(s) commonly employed in the manufacture of drugs.

The invention is further elucidated, in detail, by means of the following Examples.

EXAMPLE 1

8-Formyl-5-(4-nitrophenyl)-9H-1,3-dioxolo-/4,5-h// 2,3/benzodiazepine

A mixture of 3.23 g (10.0 mmoles) of 8-methyl-5-(4-nitrophenyl)-9H-1,3-dioxolo-/4,5-h//2,3/benzodiazepine, 1.66 g (10.5 mmoles) of selenium(IV) oxide and 100 cm$^3$ of dioxane is stirred over an oil-bath of 80° C. for 3 hours. The hot solution obtained is filtered through a coal bed, that is washed with 50 cm$^3$ of hot dioxane, and the solution is evaporated under reduced pressure. The crude product obtained is recrystallized from 100 cm$^3$ of acetonitrile. Thus, 2.50 g (74%) of the title compound are obtained. M.p.: 244–248° C.

$^1$H NMR /(CD$_3$)$_2$SO/: δ9.48 (1H, s), 8.33 (2H, d, J=8.8 Hz), 7.90 (2H, d, J=8.8 Hz), 7.04 (1H, s), 6.83 (1H, s), 6.15 (1H, S), 6.09 (1H, s), 4.03 (1H, d, J=13.1 Hz), 2.78 (1H, d, J=13.1 Hz).

EXAMPLE 2

5-(4-Nitrophenyl)-9H-1,3-dioxolo/4,5-h//2,3/-benzodiazepine-8-carboxylic acid

A solution of 1.60 g (40.0 mmoles) of sodium hydroxide in 25 cm$^3$ of water is added to a stirred solution of 3.40 g (20.0 mmoles) of silver(I) nitrate in 25 cm$^3$ of water. The reaction mixture is stirred for further 10 minutes, then diluted with 50 cm$^3$ of tetrahydrofuran. To the solution obtained, 3.37 g (10.0 mmoles) of the aldehyde obtained in Example 1 are added under ice-water cooling. The reaction mixture is stirred at room temperature for 5 hours, then filtered through a coal bed that is washed with cold water. The pH of the solution obtained is adjusted to a value of 2 with 6 n hydrochloric acid solution. After cooling, the precipitate is filtered and washed with 10 cm$^3$ of cold water. The crude product obtained is recrystallized from 30 cm$^3$ of dimethyl formamide.

Thus, 2.30 g (65%) of the title compound are obtained. M.p.: 198–203° C.

1H NMR /(CD$_3$)$_2$SO/: δ8.33 (2H, d, J=8.8 Hz), 7.89 (2H, d, J=8.8 Hz), 7.07 (1H, s), 6.85 (1H, S), 6.18 (1H, s), 6.12 (1H, s), 4.10 (1H, d, J=12.8 Hz), 2.80 (1H, d, 12.8 Hz).

EXAMPLE 3

5-(4-Nitrophenyl)-9H-1,3-dioxolo/4,5-h//2,3/-benzodiazepine-8-carboxylic acid-imidazolide 3.53 g (10.0 mmoles) of the carboxylic acid described in Example 2 are suspended im 75 cm$^3$ of anhydrous dimethylformamide at room temperature, and to the suspension 1.95 g (12.0 mmoles) of 1,1'-carbonyldiimidazole are added in one portion. The reaction mixture is stirred at room temperature for 5 hours, then, after ice-water cooling, the product precipitated is filtered, and washed with 50 cm$^3$ of diethyl ether.

Thus, 3.15 g (78%) of the title compound are obtained. M.p.: 216–220° C.

$^1$H NMR /(CD$_3$)$_2$SO/: δ8.33 (2H, d, J=8.8 Hz), 7.88 (2H, d, J=8.8 Hz), 7.86 (1H, s), 7.11 (2H, s), 7.04 (1H, S), 6.82 (1H, s), 6.16 (1H, s), 6.10 (1H, s), 6.10 (1H, s), 4.10 (1H, d, J=12.6 Hz), 2.60 (1H, d, J=12.6 Hz).

EXAMPLE 4

5-(4-Nitrophenyl)-9H-1,3-dioxolo/4,5-h//2,3/-benzodiazepine-8-carboxylic amide 4.03 g (10.0 mmoles) of the imidazolide derivative described in Example 3 are suspended in 75 cm$^3$ of dimethylformamide, to the suspension obtained 25 cm$^3$ of 25% aqueous ammonia solution are added at room temperature, and the sealed reaction mixture is stirred for 6 hours. The solvent is evaporated at a pressure of 55 Pa, the residue is suspended in 100 cm$^3$ of water, stirred for an hour, then filtered, and washed with 50 cm$^3$ of water. The crude product is dried, then boiled in 100 cm$^3$ of acetonitrile for an hour, cooled, filtered, and washed with 50 cm$^3$ of diethyl ether.

Thus, 2.96 g (84%) of the title compound are obtained. M.p.: 287–290° C.

$^1$H NMR /(CD$_3$)$_2$SO+CDCl$_3$/: δ8.33 (2H, d, J=8.9 Hz), 7.92 (2H, d, J=8.9 Hz), 7.70 (1H, broad s), 7.50 (1H, broad s), 6.98 (1H, s), 6.75 (1H, s), 6.16 (1H, s), 6.11 (1H, S), 4.30 (1H, d, J=12.3 Hz), 2.67 (1H, d, J=12.3 Hz).

EXAMPLE 5

5-(4-Nitrophenyl)-9H-1,3-dioxolo/4,5-h//2,3/-benzodiazepine-8-carboxylic acid-(N-methylamide)

4.03 g (10.0 mmoles) of the imidazolide derivative described in Example 3 are suspended in 100 cm$^3$ of dichloromethane, to the suspension 20 cm$^3$ of 33% methylamine in ethanol are added at room temperature, the reaction mixture is sealed and stirred for 8 hours, then, after ice-water cooling, the product separated is filtered, and washed with 50 cm$^3$ of diethyl ether.

Thus, 3.15 g (86%) of the title compound are obtained. M.p.: 284–287° C.

$^1$H NMR /(CD$_3$)$_2$SO/: δ8.36 (2H, d, J=8.9 Hz), 8.26 (1H, m), 7.93 (2H, d, J=8.9 Hz), 7.03 (1H, s), 6.82 (1H, s), 6.19 (1H, s), 6.13 (1H, s), 4.30 (1H, d, J=12.5 Hz), 2.77 (3H, d, J=4.8 Hz), 2.76 (1H, d, J=12.5 Hz).

EXAMPLE 6

5-(4-Nitrophenyl)-9H-1,3-dioxolo/4,5-h//2,3/-benzodiazepine-8-carboxylic acid-(N-ethylamide)

To 100 cm$^3$ of anhydrous dimethylformamide, 1.63 g (20.0 mmoles) of ethylamine hydrochloride and 2.76 g (20.0 mmoles) of potassium carbonate are added at room temperature, and, after 10 minutes' stirring, 4.03 g (10.0 mmoles) of the imidazolide derivative described in Example 3 are added. The reaction mixture is stirred for 6 hours, then the solvent is evaporated at a pressure of 55 Pa. The residue is suspended in 100 cm$^3$ of water, stirred for half an hour, filtered, washed with 50 cm$^3$ of water, and dried. The crude product is boiled in 75 cm$^3$ of acetone, cooled, filtered, and washed with 50 cm$^3$ of diethyl ether.

Thus, 2.74 g (72%) of the title compound are obtained. M.p.: 272–274° C.

$^1$H NMR /(CD$_3$)$_2$SO/: δ8.49 (1H, t, J=5.8 Hz), 8.33 (2H, d, J=8.8 Hz), 7.86 (2H, d, J=8.8 Hz), 7.01 (1H, s), 6.80 (1H, s), 6.15 (1H, s), 6.0) (1H, s), 4.22 (1H, d, J=12.8 Hz), 3.17 (2H, m), 2.69 (1H, d, J=12.8 Hz), 1.04 (3H, t, J=7.2 Hz).

EXAMPLE 7

5-(4-Nitrophenyl)-9H-1,3-dioxolo/4,5-h//2,3/-benzodiazepine-8-carboxylic acid-(N-butylamide)

4.03 g (10.0 mmoles) of the imidazolide derivative described in Example 3 are suspended in 100 cm$^3$ of dichloromethane. To the suspension, 1.47 g (1.99 cm$^3$, 20.0 mmoles) of butylamine are added at room temperature. The reaction mixture is stirred at room temperature for 12 hours, then washed twice with 30 cm$^3$ of water each time, and once with 30 cm$^3$ of saturated brine, dried over anhydrous magnesium sulfate, and evaporated. The residue is crystallized from 75 cm$^3$ of acetonitrile, and the crystals are washed with 15 cm$^3$ of diethyl ether.

Thus, 2.82 g (69%) of the title compound are obtained. M.p.: 241–245° C.

$^1$H NMR /(CD$_3$)$_2$SO): δ8.36 (1H, t, J=5.8 Hz), 8.33 (2H, d, J=9.0 Hz), 7.86 (2H, d, J=9.0 Hz), 7.02 (1H, S), 6.81 (1H, S), 6.15 (1H, s), 6.10 (1H, s), 4.22 (1H, d, J=12.4 Hz), 3.10 (2H, m), 2.70 (1H, d, J=12.4 Hz), 1.30 (4H, m), 1.04 (3H, t, J=7.3 Hz).

EXAMPLE 8

5-(4-Nitrophenyl)-9H-1,3-dioxolo/4,5-h//2,3/-benzodiazepine-8-carboxylic acid-(N,N-dimethylamide)

4.03 g (10.0 mmoles) of the imidazolide derivative described in Example 3 are suspended in 100 cm$^3$ of dichloromethane. To the suspension, 20 cm$^3$ of 33% aqueous dimethylamine solution are added at room temperature. The reaction mixture is stirred at room temperature for 5 hours, then washed twice with 30 cm$^3$ of water each time, once with 30 cm$^3$ of saturated brine, dried over anhydrous magnesium sulfate, and evaporated. The residue is crystallized from 85 cm$^3$ of acetonitrile, and the crystals are washed with 30 cm$^3$ of diethyl ether.

Thus, 2.85 g (75%) of the title compound are obtained. M.p.: 259–264° C.

$^1$H NMR (CDCl$_3$): δ8.29 (2H, d, J=9.0 Hz), 7.89 (2H, d, J=9.0 Hz), 6.96 (1H, s), 6.64 (1H, s), 6.08 (1H, s), 6.00 (1H, s), 3.96 (1H, d, J=12.5 Hz), 3.24 (3H, s), 3.05 (3H, s), 2.89 (1H, d, J=12.5 Hz).

EXAMPLE 9

5-(4-Nitrophenyl)-9H-1,3-dioxolo/4,5-h//2,3/-benzodiazepine-8-carboxylic acid-/N-(4-morpholinoethyl)amide/

4.03 g (10.0 mmoles) of the imidazolide derivative described in Example 3 are suspended in 75 cm$^3$ of anhydrous dimethylformamide. To the suspension, 2.86 g (2.86 cm$^3$, 22.0 mmoles) of 4-morpholinoethylamine are added at room temperature. The reaction mixture is stirred at room temperature for 10 hours, then, cooled with ice-water, the product precipitated is filtered, and washed with 50 cm$^3$ of diethyl ether.

Thus, 3.96 g (85%) of the title compound are obtained. M.p.: 248–252° C.

Analysis: for C$_{23}$H$_{23}$N$_5$O$_6$ (465.47)
calculated: C, 59.35%; H, 4.98%; N, 15.05%;
found: C, 59.78%; H, 5.05%; N, 14.92%.

$^1$H NMR /(CD$_3$)$_2$SO/: δ8.29 (2H, d, J=9.0 Hz), 8.02 (1H, t, J=5.7 Hz), 7.87 (2H, d, J=9.0 Hz), 6.96 (1H, s), 6.75 (1H, s), 6.12 (1H, s), 6.06 (1H, s), 4.23 (1H, d, J=12.6 Hz), 3.55 (4H, m), 3.30 (2H, m), 2.70 (1H, d, J=12.6 Hz), 2.43 (2H, t, J=6.7 Hz), 2.38 (4H, m).

EXAMPLE 10

5-(4-Nitrophenyl)-9H-1,3-dioxolo/4,5-h//2,3/-benzodiazepine-8-carboxylic acid-N-/N'-(3,4-dimethoxyphenylethyl)-(N'-methyl)aminopropyl/amide 4.03 g (10.0 mmoles) of the imidazolide derivative described in Example 3 are suspended in 100 cm$^3$ of dichloromethane. To the suspension, 2.76 g (11.0 mmoles) of N-(3,4-dimethoxyphenylethyl)-(N-methyl)aminopropylamine are added at room temperature. The reaction mixture is stirred at room temperature for 24 hours, then washed twice using 30 cm$^3$ of water each time, and once with 30 cm$^3$ of saturated brine, dried over anhydrous magnesium sulfate, and evaporated. The residue is crystallized from 50 cm$^3$ of ethanol, the crystals are washed with 10 cm$^3$ of diethyl ether.

Thus, 3.58 g (61%) of the title compound are obtained.

M.p.: 140–145.5° C.

Analysis: for $C_{31}H_{33}N_5O_7$ (587.64)

calculated: C, 63.36%; H, 5.66%; N, 11.92%;

found: C, 62.85%; H, 5.68%; N, 12.17%.

$^1$H NMR /(CD$_3$)$_2$SO/: δ8.58 (1H, t, J=5.7 Hz), 8.32 (2H, d, J=8.8 Hz), 7.86 (2H, d, J=8.8 Hz), 7.00 (1H, s), 6.70 (1H, s), 6.15 (1H, s), 6.07 (1H, s), 4.23 (1H, d, J=12.6 Hz), 3.71 (3H, s), 3.69 (3H, s), 3.17 (2H, m), 2.69 (1H, d, J=12.6 Hz), 2.55 (4H, m), 2.34 (2H, m), 2.17 (3H, s), 2.34 (2H, m).

EXAMPLE 11

5-(4-Nitrophenyl)-9H-1,3-dioxolo/4,5-h//2,3/-benzodiazepine-8-carboxylic acid-morpholide 4.03 g (10.0 mmoles) of the imidazolide derivative described in Example 3 are suspended in 100 cm$^3$ of dichloromethane. To the suspension, 1.74 g (1.74 cm$^3$, 20 mmoles) of morpholine are added at room temperature. The reaction mixture is stirred at room temperature for 10 hours, then washed twice with 30 cm$^3$ of water each time, and once with 30 cm$^3$ of saturated brine, dried over anhydrous magnesium sulfate, and evaporated. The residue is crystallized from 80 cm$^3$ of ethanol, and the crystals are washed with 30 cm$^3$ of diethyl ether.

Thus, 2.96 g (70%) of the title compound are obtained.

M.p.: 239–244° C.

$^1$H NMR /(CD$_3$)$_2$SO/: δ8.31 (2H, d, J=8.0 Hz), 7.87 (2H, d, J=8.0 Hz), 7.12 (1H, s), 6.81 (1H, s), 6.15 (1H, s), 6.11 (1H, s), 3.82 (1H, d, J=12.8 Hz), 3.50 (8H, m), 2.97 (1H, d, J=12.8 Hz).

EXAMPLE 12

5-(4-Nitrophenyl)-9H-1,3-dioxolo/4,5-h//2,3/-benzodiazepine-8-carboxylic acid-(N-methoxyamide)

1.67 g (20.0 mmoles) of methoxyamine hydrochloride and 2.76 g (20.0 mmoles) of potassium carbonate are added to 100 cm$^3$ of anhydrous dimethylformamide at room temperature, and the mixture is stirred for 10 minutes. 4.03 g (10.0 mmoles) of the imidazolide derivative described in Example 3 are added to the above mixture, and the reaction mixture obtained is stirred for 6 hours. Then, the solvent is distilled off at a pressure of 55 Pa. The residue is suspended in 100 cm$^3$ of water, stirred for half an hour, filtered, washed with 50 cm$^3$ of water, and dried. The crude product is recrystallized from 85 cm$^3$ of acetonitrile, and washed with 20 cm$^3$ of diethyl ether.

Thus, 2.30 g (60%) of the title compound are obtained.

M.p.: 247–252° C.

$^1$H NMR /(CD$_3$)$_2$SO/: δ11.89 (1H, s), 8.33 (2H, d, J=8.4 Hz), 7.87 (2H, d, J=8.4 Hz), 7.06 (1H, s), 6.82 (1H, s), 6.17 (1H, s), 6.12 (1H, s), 4.16 (1H, d, J=12.6 Hz), 3.63 (3H, s), 2.77 (1H, d, J=12.6 Hz).

EXAMPLE 13

(±)-7,8-Dihydro-5-(4-nitrophenyl)-9H-1,3-dioxolo/4,5-h//2,3/benzodiazepine-8-carboxylic amide 1.76 g (5.0 mmoles) of the carboxylic amide derivative described in Example 4 are suspended in a mixture of 75 cm$^3$ of ethanol and 75 cm$^3$ of dichloromethane, and to the suspension cooled with ice-water, 0.19 g (5.0 mmoles) of sodium tetrahydroborate are added in one portion, and 0.55 g (5.0 mmoles) of calcium chloride in 25 cm$^3$ of ethanol are added, drop by drop. The reaction mixture is stirred at room temperature for 24 hours, then evaporated under reduced pressure. The residue is boiled in 100 cm$^3$ of water for half an hour, and filtered while hot. The crude product obtained is boiled in 50 cm$^3$ of acetonitrile for half an hour, cooled wuth ice-water, filtered, and washed with 20 cm$^3$ of diethyl ether.

Thus, 1.40 g (79%) of the title compound are obtained.

M.p.: 269–272° C.

$^1$H NMR/(CD$_3$)$_2$SO/: δ8.19 (2H, d, J=9.0 Hz), 7.80 (1H, d, J=5.3 Hz), 7.64 (2H, d, J=9.0 Hz), 7.20 (1H, s), 7.16 (1H, s), 6.82 (1H, s), 6.48 (1H, s), 6.03 (1H, s), 6.02 (1H, s), 4.30 (1H, m), 3.00 (2H, m).

EXAMPLE 14

(±)-7,8-Dihydro-5-(4-nitrophenyl)-9H-1,3-dioxolo/4,5-h//2,3/benzodiazepine-8-carboxylic acid-(N-methylamide)

1.83 g (5.0 moles) of the carboxylic amide derivative described in Example 5 are suspended in a mixture of 75 cm$^3$ of ethanol and 75 cm$^3$ of dichloromethane, and to the suspension cooled with ice-water, 0.19 g (5.0 mmoles) of sodium tetrahydroborate are added in one portion, and 0.55 g (5.0 mmoles) of calcium chloride in 25 cm$^3$ of ethanol are added, drop by drop. The reaction mixture is stirred at room temperature for 24 hours, then evaporated under reduced pressure. The residue is boiled in 100 cm$^3$ of water for half an hour, and filtered while hot. The crude product obtained is crystallized from 75 cm$^3$ of ethanol, and the crystals are washed with 15 cm$^3$ of diethyl ether.

Thus, 1.25 g (68%) of the title compound are obtained.

M.p.: 201–202° C.

$^1$H NMR (CDCl$_3$): δ8.20 (2H, d, J=9.0 Hz), 7.69 (2H, d, J=9.0 Hz), 6.76 (1H, s), 6.62 (1H, m), 6.45 (1H, s), 6.12 (1H, d, J=6.7 Hz), 6.00 (2H, s), 4.66 (1H, m), 3.17 (1H, dd, J=14.0 and 4.7 Hz), 3.05 (1H, dd, J=14.0 and 3.9 Hz), 2.68 (3H, d, J=5.0 Hz).

EXAMPLE 15

(±)-7,8-Dihydro-5-(4-nitrophenyl)-9H-1,3-dioxolo/4,5-h//2,3/benzodiazepine-8-carboxylic acid-/N-(4-morpholinoethyl)amide/

3.64 g (7.8 mmoles) of the carboxylic amide derivative described in Example 9 are suspended in a mixture of 75 cm$^3$ of ethanol and 125 cm$^3$ of dichloromethane, and to the suspension cooled with ice-water, 0.30 g (7.8 mmoles) of sodium tetrahydroborate are added in one portion, and 0.87 g (7.8 mmoles) of calcium chloride in 50 cm$^3$ of ethanol are added, drop by drop. The reaction mixture is stirred at room temperature for 24 hours, then evaporated under reduced pressure. The residue is boiled in 100 cm$^3$ of water for half an hour, and filtered while hot. The crude product obtained is crystallized from 150 cm$^3$ of acetonitrile, and the crystals are washed with 30 cm$^3$ of diethyl ether.

Thus, 2.56 g (70%) of the title compound are obtained.

M.p.: 192–195° C.

$^1$H NMR/(CD$_3$)$_2$SO/: δ8.19 (2H, d, J=9.0 Hz), 7.94 (1H, d, J=6.0 Hz), 7.65 (2H, d, J=9.0 Hz), 7.46 (1H, t, J=5.8 Hz), 6.74 (1H, s), 6.45 (1H, s), 6.00 (2H, s), 4.41 (1H, m), 3.50

(4H, m), 3.10 (2H, m), 2.94 (2H, m), 2.22 (4H, m), 2.07 (1H, m), 1.94 (1H, m).

EXAMPLE 16

(±)-7-Acetyl-7,8-dihydro-5-(4-nitrophenyl)-9H-1,3-dioxolo/4,5-h//2,3/benzodiazepine-8-carboxylic amide 3.5.4 g (10.0 mmoles) of the dihydrocarboxylic amide derivative described in Example 13 are suspended in 50 cm$^3$ of acetic anhydride, and the suspension is stirred at room temperature for 48 hours. The reaction mixture is cooled with ice-water, the product precipitated is filtered, recrystallized from 100 cm$^3$ of acetonitrile, and washed with 20 cm$^3$ of diethyl ether.

Thus, 3.13 g (79%) of the title compound are obtained.

M.p.: 164–165° C.

$^1$H NMR/(CD$_3$)$_2$SO/: δ8.35 (2H, d, J=9.0 Hz), 7.82 (2H, d, J=9.0 Hz), 7.35 (1H, s), 7.05 (1H, s), 6.92 (1H, s), 6.54 (1H, s), 6.12 (1H, s), 6.10 (1H, s), 5.53 (1H, dd, J=7.7 and 2.7 Hz), 3.31 (1H, dd, J=14.5 and 7.7 Hz), 3.16 (1H, dd, J=14.5 and 2.7 Hz), 2.39 (3H, s).

EXAMPLE 17

(±)-7-Acetyl-7,8-dihydro-5-(4-nitrophenyl)-9H-1,3-dioxolo/4,5-h//2,3/benzodiazepine-8-carboxylic acid-(N-methylamide)

3.68 g (10.0 mmoles) of the dihydrocarboxylic amide derivative described in Example 14 are suspended in 25 cm$^3$ of acetic anhydride, and stirred at room temperature for 48 hours. The reaction mixture is poured onto a mixture of 200 cm$^3$ of water and 100 cm$^3$ of dichloromethane, the mixture obtained is stirred for one hour, then the pH is adjusted to a value of 8 by adding sodium carbonate in portions. The phases are separated, the aqueous phase is extracted twice using 100 cm$^3$ of dichloromethane each time, the combined organic phases are washed with 50 cm$^3$ of saturated brine, dried over anhydrous magnesium sulfate, and evaporated. The crude product obtained is recrystallized from 150 cm$^3$ of ethanol, the crystals are washed with 25 cm$^3$ of diethyl ether.

Thus, 3.08 g (75%) of the title compound are obtained.

M.p.: 148–151° C.

$^1$H NMR (CDCl$_3$): δ8.27 (2H, d, J=8.9 Hz), 7.79 (2H, d, J=8.9 Hz), 6.83 (1H, s), 6.45 (1H, s), 6.07 (1H, m), 6.03 (2H, s), 5.64 (1H, dd, J=9.2 and 3.9 Hz), 3.31 (1H, dd, J=14.4 and 9.2 Hz), 3.16 (1H, dd, J=14.5 and 3.9 Hz), 2.68 (3H, d, J=4.8 Hz), 2.35 (3H, s).

EXAMPLE 18

(±)-7-Acetyl-7,8-dihydro-5-(4-nitrophenyl)-9H-1,3-dioxolo/4,5-h//2,3/benzodiazepine-8-carboxylic acid-/(N-morpholinoethyl)amide/

2.60 g (5.6 mmoles) of the dihydrocarboxylic amide derivative described in Example 15 are suspended in 15 cm$^3$ of acetic anhydride, and stirred at room temperature for 48 hours. The reaction mixture is poured onto a mixture of 150 cm$^3$ of water and 75 cm$^3$ of dichloromethane, the mixture obtained is stirred for an hour, then the pH is adjusted to a value of 8 by adding sodium carbonate in several portions. The phases are separated, the aqueous phase is extracted twice using 75 cm$^3$ of dichloromethane each time, the combined organic phases are washed with 25 cm$^3$ of saturated brine, dried over anhydrous magnesium sulfate, and evaporated. The crude product obtained is recrystallized from 100 cm$^3$ of acetonitrile, the crystals are washed with 20 cm$^3$ of diethyl ether.

Thus, 1.73 g (68%) of the title compound are obtained.

M.p.: 212–217° C.

$^1$H NMR/(CDCl$_3$+(CD$_3$)$_2$SO/: δ8.19 (2H, d, J=8.8 Hz), 7.74 (2H, d, J=8.8 Hz), 7.06 (1H, m), 6.76 (1H, s), 6.39 (1H, s), 5.97 (1H, s), 5.95 (1H, s), 5.45 (1H, dd, J=7.9 and 3.1 Hz), 3.55 (4H, m), 3.23 (1H, dd, J=14.6 and 7.9 Hz), 3.06 (3H, m), 2.33 (3H, s), 2.28 (4H, m), 2.17 (1H, m), 2.12 (1H, m).

EXAMPLE 19

8-Hydroxyiminomethyl-5-(4-nitrophenyl)-9H-1,3-dioxolo/4,5-h//2,3/benzodiazepine 3.37 g (10.0 mmoles) of the aldehyde obtained in Example 1, 0.83 g (12.0 mmoles) of hydroxylamine hydrochloride and 1.09 g (13.0 mmoles) of anhydrous sodium acetate are boiled in 100 cm$^3$ of ethanol for 10 hours. The reaction mixture is evaporated under reduced pressure, the residue is suspended in 150 cm$^3$ of water, stirred at room temperature for half an hour, filtered, and washed with 25 cm$^3$ of water. The crude product obtained is dried, then boiled in 30 cm$^3$ of acetone, cooled with ice-water, filtered, and washed with 30 cm$^3$ of diethyl ether.

Thus, 2.85 g (81%) of the title compound are obtained.

M.p.: 262–265° C.

EXAMPLE 20

8-Cyano-5-(4-nitrophenyl)-9H-1,3-dioxolo/4,5-h//2, 3/benzodiazepine 2.00 g (5.7 mmoles) of the oxime obtained in Example 19 are suspended in 100 cm$^3$ of dichloromethane. To the suspension obtained, 1.37 g (1.90 cm$^3$, 13.6 mmoles) of triethylamine, then, 0.78 g (0.53 cm$^3$, 6.8 mmoles) of methanesulfonyl chloride in 10 cm$^3$ of dichloromethane are added, drop by drop, under cooling with ice-water. The reaction mixture is stirred at room temperature for 4 hours, then washed twice with 30 cm$^3$ of water each time, once with 30 cm$^3$ of saturated brine, dried over anhydrous magnesium sulfate, and evaporated under reduced pressure. The crude product obtained is recrystallized from 75 cm$^3$ of acetonitrile, the crystals are washed with 20 cm$^3$ of diethyl ether.

Thus, 1.27 g (67%) of the title compound are obtained.

M.p.: 230–234° C.

$^1$H NMR/CDCl$_3$+(CD$_3$)$_2$SO/: δ8.30 (2H, d, J=8.6 Hz), 7.89 (2H, d, J=8.6 Hz), 6.92 (1H, s), 6.72 (1H, s), 6.15 (1H, s), 6.13 (1H, s), 3.67 (1H, d, J=13.8 Hz), 3.17 (1H, d, J=13.8 Hz).

EXAMPLE 21

8-(5-Tetrazolyl)-5-(4-nitrophenyl)-9H-1,3-dioxolo/4, 5-h//2,3/benzodiazepine 4.06 g (12.2 mmoles) of the nitrile obtained in Example 20, 0.65 g (12.2 mmoles) of ammonium chloride and 7.90 g (121.5 mmoles) of sodium azide are stirred in 100 cm$^3$ of anhydrous dimethylformamide over an oilbath of 80° C. for 6 hours. The solvent is evaporated at a pressure of 50 Pa, the residue is taken up in 75 cm$^3$ of water, and the pH of the solution is adjusted to a value of 3 with 6 n hydrochloric acid. The product precipitated is cooled with ice-water, filtered, and washed with 15 cm$^3$ of cold water. The crude product obtained is boiled in 100 cm$^3$ of acetone for half an hour, cooled with ice-water, filtered, and washed with 20 cm$^3$ of diethyl ether.

Thus, 3.25 g (71%) of the title compound are obtained.

M.p.: 228–232° C.

$^1$H NMR/(CD$_3$)$_2$SO/: δ8.32 (2H, d, J=8.8 Hz), 7.92 (2H, d, J=8.8 Hz), 7.04 (1H, s), 6.79 (1H, s), 6.11 (1H, s), 6.02 (1H, s), 4.52 (1H, d, J=12.4 Hz), 3.06 (1H, d, J=12.4 Hz).

EXAMPLE 22

8-Methanesulfonyloxymethyl-5-(4-nitrophenyl)-9H-1,3-dioxolo/4,5-h//2,3/benzodiazepine 3.37 g (10.0 mmoles) of the aldehyde obtained in Example 1 are dissolved in a mixture of 100 cm$^3$ of dichloromethane and 10 cm$^3$ of methanol. To the solution obtained, 0.10 g (2.5 mmoles) of sodium tetrahydroborate are added in one portion under cooling with ice-water. The reaction mixture is stirred for half an hour, filtered, washed twice with 30 cm$^3$ of water each time, once with 30 cm$^3$ of saturated brine, dried over anhydrous magnesium sulfate, and evaporated under reduced pressure. The residue is taken up in 75 cm$^3$ of anhydrous dichloromethane, and to the solution obtained, 1.11 g (11.0 mmoles) of triethylamine, then 1.26 g (0.85 cm$^3$, 11.0 mmoles) of methanesulfonyl chloride in 5 cm$^3$ of anhydrous dichloromethane are added, drop by drop, under cooling with ice-water. The reaction mixture is stirred at 0° C. for 1.5 hours, the product precipitated is filtered, washed with 25 cm$^3$ of diethyl ether.

Thus, 2.67 g (64%) of the title compound are obtained.

M.p.: 190–192° C.

$^1$H NMR/(CD$_3$)$_2$SO/: δ8.28 (2H, d, J=8.8 Hz), 7.86 (2H, d, J=8.8 Hz), 7.07 (1H, s), 6.76 (1H, s), 6.13 (1H, s), 6.10 (1H, s), 4.98 (1H, d, J=13.8 Hz), 4.93 (1H, d, J=13.8 Hz), 3.63 (1H, d, J=13.1 Hz), 3.23 (3H, s), 2.88 (1H, d, J=13.1 Hz).

EXAMPLE 23

8-(4-Morpholinomethyl)-5-(4-nitrophenyl)-9H-1,3-dioxolo/4,5-h//2,3/benzodiazepine 2.08 g (5.0 mmoles) of the mesylate obtained in Example 22 are suspended in 75 cm$^3$ of dichloromethane, to the suspension obtained, 2.18 g (2.18 cm$^3$, 25.0 mmoles) of morpholine are added, and the reaction mixture is stirred at room temperature for a day. The clear solution obtained is washed twice with 30 cm$^3$ of water each time, once with 30 cm$^3$ of saturated brine, dried over anhydrous magnesium sulfate, and evaporated under reduced pressure. The crude product obtained is stirred in 35 cm$^3$ of acetone for half an hour, cooled with ice-water, filtered, and washed with 20 cm$^3$ of diethyl ether.

Thus, 1.61 g (79%) of the title compound are obtained.

M.p.:235–237° C.

$^1$H NMR (CDCl$_3$): δ8.27 (2H, d, J=9.0 Hz), 7.87 (2H, d, J=9.0 Hz), 6.85 (1H, s), 6.65 (1H, s), 6.07 (1H, s), 6.02 (1H, s), 3.72 (1H, d, J=12.1 Hz), 3.67 (4H, m), 3.23 (2H, m), 2.86 (1H, d, J=12.1 Hz), 2.45 (2H, m), 2.32 (2H, m).

EXAMPLE 24

8-Methylaminomethyl-5-(4-nitrophenyl)-9H-1,3-dioxolo/4,5-h//2,3/benzodiazepine 2.08 g (5.0 mmoles) of the mesylate obtained in Example 22 are suspended in 75 cm$^3$ of dichloromethane. 25 cm$^3$ of 25% aqueous ammonia solution are added, and the reaction mixture is stirred at room temperature for a day. The phases of the reaction mixture are separated, the organic phase is washed twice with 30 cm$^3$ of water each time, then with 30 cm$^3$ of saturated brine, dried over anhydrous magnesium sulfate, and evaporated under reduced pressure. The crude product obtained is stirred in 20 cm$^3$ of acetone for half an hour, cooled with ice-water, filtered, and washed with 15 cm$^3$ of diethyl ether.

Thus, 1.32 g (75%) of the title compound are obtained.

M.p.: 214–215° C.

$^1$H NMR (CDCl$_3$): δ8.27 (2H, d, J=9.0 Hz), 7.87 (2H, d, J=9.0 Hz), 6.79 (1H, s), 6.66 (1H, s), 6.09 (1H, d, J=1.3 Hz), 6.03 (1H, d, J=1.3 Hz), 3.61 (1H, d, J=15.9 Hz), 3.48 (1H, d, J=12.5 Hz), 3.47 (1H, d, J=15.9 Hz), 2.87 (1H, d, J=12.5 Hz), 2.39 (3H, s), 1.25 (1H, broad s).

EXAMPLE 25

8-Dimethylaminomethyl-5-(4-nitrophenyl)-9H-1,3-dioxolo/4,5-h//2,3/benzodiazepine 2.08 g (5.0 mmoles) of the mesylate obtained in Example 22 are suspended in 75 cm$^3$ of dichloromethane, 25 cm$^3$ of 40% aqueous dimethylamine solution are added, and the reaction mixture is stirred at room temperature for a day. The phases are separated, the organic phase is washed twice with 30 cm$^3$ of water each time, then with 30 cm$^3$ of saturated brine, dried over anhydrous magnesium sulfate, and evaporated under reduced pressure. The crude product obtained is stirred in 25 cm$^3$ of acetone for half an hour, then cooled with ice-water, filtered, and washed with 15 cm$^3$ of diethyl ether.

Thus, 1.17 g (64%) of the title compound are obtained.

M.p.: 182–185° C.

$^1$H NMR (CDCl$_3$): δ8.26 (2H, d, J=9.0 Hz), 7.88 (2H, d, J=9.0 Hz), 6.84 (1H, s), 6.66 (1H, s), 6.08 (1H, d, J=1.3 Hz), 6.04 (1H, d, J=1.3 Hz), 3.74 (1H, d, J=12.3 Hz), 3.21 (1H, d, J=13.5 Hz), 3.07 (1H, d, J=13.5 Hz), 2.80 (1H, d, J=12.3 Hz), 2.25 (6H, s).

EXAMPLE 26

8-(N-Acetyl-N-methylaminomethyl)-5-(4-nitrophenyl)-9H-1,3-dioxolo/4,5-h//2,3/benzodiazepine 3.52 g (10.0 mmoles) of the benzodiazepine derivative obtained in Example 24 are stirred in 25 cm$^3$ of acetic anhydride at room temperature for 24 hours. The reaction mixture is poured onto a mixture of 150 cm$^3$ of water and 75 cm$^3$ of dichloromethane, the mixture obtained is stirred for an hour, and the pH is adjusted to a value of 8 by adding several portions of sodium carbonate. The phases are separated, the aqueous phase is extracted twice using 75 cm$^3$ of dichloromethane each time, the combined organic phases are washed with 25 cm$^3$ of saturated brine, dried over anhydrous magnesium aulfate, and evaporated. The crude product obtained is recrystallized from 75 cm$^3$ of acetonitrile, the crystals are washed with 20 cm$^3$ of diethyl ether.

Thus, 3.11 g (79%) of the title compound are obtained.

M.p.: 224–228° C.

$^1$H NMR (CDCl$_3$): δ8.26 (2H, d, J=8.9 Hz), 7.86 (2H, d, J=8.9 Hz), 6.80 (1H, s), 6.66 (1H, s), 6.07 (1H, d, J=1.2 Hz), 6.04 (1H, d, J=1.2 Hz), 4.42 (1H, d, J=14.4 Hz), 4.23 (1H, d, J=14.4 Hz), 3.52 (1H, d, J=12.5 Hz), 2.86 (3H, s), 2.79 (1H, d, J=12.5 Hz), 2.18 (3H, s).

EXAMPLE 27

Methyl 5-(4-nitrophenyl)-9H-1,3-dioxolo/4,5-h//2,3/ benzodiazepine-8-carboxylate 3.53 g (10.0 mmoles) of the carboxylic acid described in Example 2 are suspended in 150 cm³ of methanol, 0.2 cm³ of concentrated sulfuric acid are added, and the reaction mixture is boiled for 10 hours. After cooling, the pH is adjusted to a value of 8 by means of triethylamine, the mixture is cooled with ice-water, and the product is filtered. The crude product obtained is recrystallized from 100 cm³ of acetonitrile, the crystals are washed with 25 cm³ of diethyl ether.

Thus, 3.2 g (85%) of the title compound are obtained.

M.p.: 237–240° C.

$^1$H NMR (CDCl$_3$): δ8.29 (2H, d, J=9.0 Hz), 7.90 (2H, d, J=9.0 Hz), 6.90 (1H, s), 6.68 (1H, s), 6.09 (1H, d, J=1.3 Hz), 4.19 (1H, d, J=12.8 Hz), 3.90 (3H, s), 2.83 (1H, d, J=12.8 Hz).

EXAMPLE 28

(±)-7-Acetyl-8-(acetyl-N-methylaminomethyl)-7,8-dihydro-5-(4-nitrophenyl)-9H-1,3-dioxolo/4,5-h//2,3/benzodiazepine 1.76 g (5.0 mmoles) of amino derivative described in Example 24 are dissolved in a mixture of 100 cm³ of ethanol and 100 cm³ of ethyl acetate, to the solution obtained, 7.3 cm³ of concentrated hydrochloric acid and then 2.20 g (58.2 mmoles) of sodium tetrahydroborate are added in small portions at room temperature. The reaction mixture is stirred for half an hour, then evaporated, the residue is taken up in a mixture of 100 cm³ of dichloromethane and 100 cm³ of water. The pH of the solution is adjusted to a value of 8 by adding 10 n sodium hydroxide solution. The layers are separated, the aqueous phase is extracted twice using 50 cm³ of dichloromethane each time, the combined organic phases are washed with 30 cm³ of saturated brine, dried over anhydrous magnesium sulfate, and evaporated. The residue obtained is stirred in 15 cm³ of acetic anhydride for 10 hours, then diluted with a mixture of 100 cm³ of water and 100 cm³ of dichloromethane. The mixture is stirred for an hour, and the pH of the aqueous phase is adjusted to a value of 8 by adding sodium carbonate. The phases are separated, the aqueous phase is extracted twice using 50 cm³ of dichloromethane each time, the combined organic phases are washed with 30 cm³ of saturated brine, dried over anhydrous magnesium sulfate, and evaporated under reduced pressure. The crude product obtained is recrystallized from 50 cm³ of diethyl ether.

Thus, 1.49 g (68%) of the title compound are obtained.

M.p.: 115–117° C.

$^1$H NMR/(CD$_3$)$_2$SO, 140° C./: δ8.38 (2H, d, J=8.4 Hz), 7.94 (2H, d, J=8.4 Hz), 7.12 (1H, s), 6.67 (1H, s), 6.17 (2H, s), 5.61 (1H, m), 3.39 (2H, m), 3.03 (3H, s), 3.01 (2H, m), 2.23 (3H, s), 2.04 (3H, s).

EXAMPLE 29

8-Acetoxymethyl-5-(4-nitrophenyl)-9H-1,3-dioxolo/4,5-h//2,3/benzodiazepine 3.37 g (10.0 mmoles) of the aldehyde obtained in Example 1 are dissolved in a mixture of 100 cm³ of dichloromethane and 10 cm³ of methanol, and, to the solution obtained, 0.10 g (2.5 mmoles) of sodium tetrahydroborate are added in one portion under cooling with ice-water. The reaction mixture is stirred for half an hour, filtered, washed twice with 30 cm³ of water each time, then with 30 cm³ of saturated brine, dried over anhydrous magnesium sulfate, and evaporated under reduced pressure. The residue is stirred in 25 cm³ of acetic anhydride for 10 hours, then diluted with a mixture of 100 cm³ of water and 100 cm³ of dichloromethane, the mixture obtained is stirred for an hour, and the pH of the aqueous phase is adjusted to a value of 8 by adding sodium carbonate. The phases are separated, the aqueous phase is extracted twice using 50 cm³ of dichloromethane each time, the combined organic phases are washed with 30 cm³ of saturated brine, dried over anhydrous magnesium sulfate, and evaporated under reduced pressure. The crude product obtained is recrystallized from 50 cm³ of acetonitrile.

Thus, 2.74 g (72%) of the title compound are obtained.

M.p.: 189–193° C.

$^1$H NMR/CDCl$_3$+(CD$_3$)$_2$SO/: δ8.18 (2H, d, J=9.0 Hz), 7.82 (2H, d, J=9.0 Hz), 6.81 (1H, s), 6.60 (1H, s), 6.02 (1H, s), 5.98 (1H, s), 4.81 (1H, d, J=13.9 Hz), 4.69 (1H, d, J=13.9 Hz), 3.47 (1H, d, J=12.9 Hz), 2.81 (1H, d, J=12.9 Hz), 2.07 (3H, s).

EXAMPLE 30

(±)-7-Acetyl-8-acetoxymethyl-7,8-dihydro-5-(4-nitrophenyl)-9H-1,3-dioxolo/4,5-h//2,3/benzodiazepine 3.37 g (10.0 mmoles) of the aldehyde obtained in Example 1 are dissolved in a mixture of 100 cm³ of dichloromethane and 10 cm³ of methanol, and, to the solution obtained, 0.38 g (10.0 mmoles) of sodium tetrahydroborate are added in one portion under cooling with ice-water. The reaction mixture is stirred for half an hour, filtered, washed twice with 30 cm³ of water each time, then with 30 cm³ of saturated brine, dried over anhydrous magnesium sulfate, and evaporated under reduced pressure. The residue is stirred in 25 cm³ of acetic anhydride for 24 hours, then diluted with a mixture of 100 cm³ of water and 100 cm³ of dichloromethane. The mixture obtained is stirred for an hour, then the pH of the aqueous phase is adjusted to a value of 8 by adding sodium carbonate. The phases are separated, the aqueous phase is extracted twice using 50 cm³ of dichloromethane each time, the combined organic phases are washed with 30 cm³ of saturated brine, dried over anhydrous magnesium sulfate, and evaporated under reduced pressure. The crude product obtained is boiled in 50 cm³ of diethyl ether for an hour, then cooled with ice-water, and filtered.

Thus, 3.19 g (75%) of the title compound are obtained.

M.p.: 114–115° C.

$^1$H-NMR (CDCl$_3$): δ8.28 (2H, d, J=9.0 Hz), 7.72 (2H, d, J=9.0 Hz), 6.75 (1H, s), 6.48 (1H, s), 6.03 (2H, s), 5.60 (1H, m), 3.88 (2H, m), 3.05 (2H, m), 2.34 (3H, s), 2.03 (3H, s).

EXAMPLE 31

8-(1,5-Diazabicyclo/4.3.0/non-5-enium-5-ylmethyl)-5-(4-nitrophenyl)-9H-1,3-dioxolo/4,5-h//2,3/benzodiazepine methanesulfonate 2.08 g (5.0 mmoles) of the mesylate obtained in Example 22 and 0.68 g (0.66 cm³, 5.5 mmoles) 1,5-diazabicyclo/4.3.0/non-5-ene are boiled in 50 cm³ of anhydrous tetrahydrofuran for 4 hours, then cooled with ice-water, the product precipitated is filtered, and washed with 25 cm³ of diethyl ether.

Thus, 2.33 g (86%) of the title compound are obtained.

M.p.: 205–207° C.

$^1$H NMR (CDCl$_3$): δ8.27 (2H, d, J=8.6 Hz), 7.85 (2H, d, J=8.6 Hz), 7.01 (1. s), 6.66 (1H, s), 6.11 (1H, s), 6.09 (1H, s), 4.84 (1H, d, J=19.2 Hz), 4.53 (1H, d, J=19.2 Hz), 3.81 (2H, m), 3.57 (1H, d, J=13.0 Hz), 3.53 (2H, m), 3.35 (2H, m), 3.12 (2H, m), 2.94 (1H, d, J=13.0 Hz), 2.85 (2H, m), 2.75 (3H, s), 2.18 (4H, m).

EXAMPLES 32 TO 56

A general method for the reduction of the nitro group of the compounds described in Example 1 to 31 by catalytic hydrogenation.

5.0 mmoles of nitro compound are dissolved in a mixture of 100 cm$^3$ of dichloromethane and 100 cm$^3$ of methanol, and the solution is hydrogenized in the presence of 0.10 g of 10% palladium/carbon catalyst at room temperature and 5.065×10$^5$ Pa pressure. After the hydrogenation, the catalyst is filtered, the solvent is evaporated under reduced pressure, and the crude product is recrystallized.

EXAMPLE 32

5-(4-Aminophenyl)-9H-1,3-dioxolo/4,5-h//2,3/ benzodiazepine-8-carboxylic amide

Solvent for crystallization: dimethylformamide and ethanol.

M.p.: 276–280° C.

Yield: 68%.

Analysis: for C$_{17}$H$_{14}$N$_4$O$_3$ (322.33)

calculated: C, 63.35%; H, 4.38%; N, 17.38%.

found: C, 63.93%; H, 4.31%; N, 17.24%.

$^1$H NMR/(CD$_3$)$_2$SO/: δ7.80 (1H, s), 7.50 (1H, s), 7.38 (2H, d, J=8.6 Hz), 6.97 (1H, s), 6.80 (1H, s), 6.66 (2H, d, J=8.6 Hz), 6.17 (1H, s), 6.11 (1H, s), 5.73 (2H, s), 4.18 (1H, d, J=12.3 Hz), 2.65 (1H, d, J=12.3 Hz).

EXAMPLE 33

5-(4-Aminophenyl)-9H-1,3-dioxolo/4,5-h//2,3/ benzodiazepine-8-carboxylic acid-(N-methylamide)

Solvent for crystallization: ethanol.

M.p.: 149–152° C.

Yield: 72%.

Analysis: for C$_{18}$H$_{16}$N$_4$O$_3$ (3363.35)

calculated: C, 64.28%; H, 4.79%; N, 16.66%.

found: C, 64.88%; H, 4.85%; N, 16.33%.

$^1$H NMR/(CD$_3$)$_2$SO/: δ7.95 (1H, m), 7.39 (2H, d, J=8.7 Hz), 6.82 (1H, s), 6.73 (1H, s), 6.66 (2H, d, J=8.7 Hz), 6.04 (1H, d, J=1.0 Hz), 5.98 (1H, d, J=1.0 Hz), 5.05 (2H, s), 4.22 (1H, d, J=12.4 Hz), 2.78 (3H, d, J=5.0 Hz), 2.67 (1H, d, J=12.4 Hz).

EXAMPLE 34

5-(4-Aminophenyl)-9H-1,3-dioxolo/4,5-h//2,3/ benzodiazepine-8-carboxylic acid-(N-ethylamide)

Solvent for crystallization: ethanol.

M.p.: 137–140° C.

Yield: 76%.

Analysis: for C$_{19}$H$_{18}$N$_4$O$_3$ (350.38)

calculated: C, 65.13%; H, 5.18%; N, 15.99%.

found: C, 64.92%; H, 5.18%; N, 15.44%.

$^1$H NMR/(CD$_3$)$_2$SO/: δ8.40 (1H, t, J=5.9 Hz), 7.32 (2H, d; J=8.6 Hz), 6.92 (1H, s), 6.75 (1H, s), 6.62 (2H, d, J=8.6 Hz), 6.12 (1H, d, J=1.0 Hz), 6.07 (1H, d, J=0.7 Hz), 5.65 (2H, broad s), 4.14 (1H, d, J=12.5 Hz), 3.16 (2H, m), 2.63 (1H, d, J=12.5 Hz), 1.03 (3H, t, J=7.1 Hz).

EXAMPLE 35

5-(4-Aminophenyl)-9H-1,3-dioxolo/4,5-h//2,3/ benzodiazepine-8-carboxylic acid-(N-butylamide)

Solvent for crystallization: acetonitrile.

M.p.: 215–216° C.

Yield: 70%.

Analysis: for C$_{21}$H$_{22}$N$_4$O$_3$ (378.43)

calculated: C, 66.65%; H, 5.86%; N, 14.80%.

found: C, 66.44%; H, 5.97%; N, 14.45%.

$^1$H NMR/(CD$_3$)$_2$SO/: δ8.37 (1H, t, J=6.0 Hz), 7.33 (2H, d, J=8.4 Hz), 6.91 (1H, s), 6.75 (1H, s), 6.61 (2H, d, J=8.4 Hz), 6.12 (1H, s), 6.07 (1H, s), 5.67 (2H, broad s), 4.13 (1H, d, J=12.4 Hz), 3.09 (2H, m), 2.63 (1H, d, J=12.4 Hz), 1.40 (2H, m), 1.25 (2H, m), 1.03 (3H, t, J=7.1 Hz).

EXAMPLE 36

5-(4-Aminophenyl)-9H-1,3-dioxolo/4,5-h//2,3/ benzodiazepine-8-carboxylic acid-(N,N-dimethylamide)

Solvent for crystallization: ethanol.

M.p.: 257–262° C.

Yield: 69%.

Analysis for C$_{19}$H$_{18}$N$_4$O$_3$ (350.38)

calculated: C, 65.13%; H, 5.18%; N, 15.99%.

found: C, 65.54%; H, 5.22%; N, 15.53%.

$^1$H NMR/(CD$_3$)$_2$SO/: δ7.31 (2H, d, J=8.4 Hz), 7.01 (1H, s), 6.76 (1H, s), 6.60 (2H, d, J=8.4 Hz), 6.12 (1H, s), 6.09 (1H, s), 5.63 (2H, broad s), 3.68 (1H, d, J=12.8 Hz), 2.90 (3H, s), 2.88 (3H, s), 2.87 (1H, d, J=12.8 Hz).

EXAMPLE 37

5-(4-Aminophenyl)-9H-1,3-dioxolo/4,5-h//2,3/ benzodiazepine-8-carboxylic acid-/N-(4-morpholinoethyl)amide/

Solvent for crystallization: ethanol.

M.p.: 254–255° C.

Yield: 70%.

Analysis: for C$_{21}$H$_{20}$N$_4$O$_3$ (392.42)

calculated: C, 63.44%; H, 5.79%; N, 16.08%.

found: C, 63.85%; H, 5.76%; N, 15.91%.

$^1$H NMR (CDCl$_3$): δ7.52 (2H, d, J=8.7 Hz), 6.87 (1H, s), 6.70 (1H, s), 6.69 (2H, d, J=8.7 Hz), 6.02 (1H, d, J=1.2 Hz), 5.95 (1H, s), 4.58 (1H, d, J=12.4 Hz), 4.02 (2H, broad s), 3.69 (4H, m), 3.48 (1H, m), 3.36 (1H, m), 2.75 (1H, d, J=12.4 Hz), 2.48 (2H, m), 2.42 (4H, m).

EXAMPLE 38

5-(4-Aminophenyl)-9H-1,3-dioxolo/4,5-h//2,3/ benzodiazepine-8-carboxylic acid-[N-/(N'-(3,4-dimethoxyphenylethyl)-(N'-methyl)aminopropyl/ amide]

Solvent for crystallization: toluene.

M.p.: 123–126° C.

Yield: 63%.

Analysis: for C₃₁H₃₅N₅O₅ (557.66)
calculated: C, 66.77%; H, 6.33%; N, 12.56%.
found: C, 65.61%; H, 6.31%; N, 12.25%.

¹H NMR (CDCl₃): δ7.67 (1H, t, J=8.6 Hz), 7.58 (2H, d, J=8.6 Hz), 6.98 (2H, d, J=8.6 Hz), 6.85 (1H, s), 6.75 (3H, m), 6.70 (1H, s), 5.99 (1H, d, J=0.8 Hz), 5.91 (1H, d, J=1.0 Hz), 4.28 (1H, d, J=12.6 Hz), 3.83 (6H, s), 3.35 (2H, m), 2.65 (1H, d, J=12.6 Hz), 2.60 (6H, m), 2.29 (3H, s), 1.74 (2H, t, 6.6 Hz).

EXAMPLE 39

5-(4-Aminophenyl)-9H-1,3-dioxolo/4,5-h//2,3/benzodiazepine-8-carboxylic acid-morpholide Solvent for crystallization: ethanol.
M.p.: 254–255° C.
Yield: 83%.
Analysis: for C₂₁H₂₀N₄O₄ (392.42)
calculated: C, 64.28%; H, 5.14%; N, 14.28%.
found: C, 63.48%; H, 5.18%; N, 14.08%.

¹H NMR (CDCl₃): δ7.50 (2H, d, J=8.7 Hz), 6.90 (1H, s), 6.76 (1H, s), 7.50 (2H, d, J=8.7 Hz), 6.02 (1H, d, J=1.2 Hz), 5.95 (1H, d, J=1.2 Hz), 3.95 (2H, m), 3.85 (1H, d, J=12.4 Hz), 3.66 (8H, m), 2.95 (1H, d, J=12.4 Hz).

EXAMPLE 40

5-(4-Aminophenyl)-9H-1,3-dioxolo/4,5-h//2,3/benzodiazepine-8-carboxylic acid-(N-methoxyamide)

Solvent for crystallization: acetonitrile.
M.p.: 159–162° C.
Yield: 74%.
Analysis: for C₁₈H₁₆N₄O₄ (352.35)
calculated: C, 61.36%; H, 4.58%; N, 15.90%.
found: C, 59.26%; H, 4.51%; N, 15.50%.

¹H NMR/(CD₃)₂SO/: δ11.76 (1H, s), 7.32 (2H, d, J=8.6 Hz), 6.95 (1H, s), 6.76 (1H, s), 6.61 (1H, d, J=8.6 Hz), 6.13 (1H, s), 6.08 (1H, s), 5.68 (2H, broad s), 4.05 (1H, d, J=12.6 Hz), 3.60 (3H, s), 2.69 (1H, d, J=12.6 Hz).

EXAMPLE 41

(±)-5-(4-Aminophenyl)-7,8-dihydro-9H-1,3-dioxolo/4,5-h//2,3/benzodiazepine-8-carboxylic amide Solvent for crystallization: acetonitrile.
M.p.: 256–258° C.
Yield: 69%.
Analysis: for C₁₇H₁₆N₄O₃ (324.34)
calculated: C, 62.95%; H, 4.97%; N, 17.27%.
found: C, 62.74%; H, 4.87%; N, 17.38%.

¹H NMR/(CD₃)₂SO/: δ7.20 (1H, broad s), 7.15 (2H, d, J=8.6 Hz), 7.00 (1H, broad s), 6.81 (1H, s), 6.51 (2H, d, J=8.6 Hz), 6.50 (1H, broad s), 6.48 (1H, s), 6.04 (1H, s), 6.03 (1H, s), 5.37 (2H, broad s), 4.15 (1H, q, J=10.5 and 5.9 Hz), 2.78 (2H, m).

EXAMPLE 42

(±)-5-(4-Aminophenyl)-7,8-dihydro-9H-1,3-dioxolo/4,5-h//2,3/benzodiazepine-8-carboxylic acid-(N-methylamide)

Solvent for crystallization: acetonitrile.
M.p.: 231–234° C.
Yield: 71%.
Analysis: for C₁₈H₁₈N₄O₃ (338.37)
calculated: C, 63.89%; H, 5.36%; N, 16.56%.
found: C, 63.90%; H, 5.48%; N, 16.30%.

¹H NMR/(CD₃)₂SO/: δ7.47 (1H, m), 7.17 (2H, d, J=8.4 Hz), 6.77 (1H, s), 6.53 (2H, d, J=8.4 Hz), 6.49 (1H, s), 6.04 (1H, s), 6.02 (1H, s), 5.37 (2H, broad s), 4.22 (1H, m), 2.79 (2H, d, J=5.4 Hz), 2.54 (3H, d, J=4.6 Hz).

EXAMPLE 43

Solvent for crystallization: acetonitrile.
M.p.: 231–234° C.
Yield: 71%.
Analysis: for C₁₈H₁₈N₄O₃ (338.37)
calculated: C, 63.89%; H, 5.36%; N, 16.56%.
found: C, 63.90%; H, 5.48%; N, 16.30%.

¹H NMR/(CD₃)₂SO/: δ7.47 (1H, m), 7.17 (2H, d, J=8.4 Hz), 6.77 (1H, s), 6.53 (2H, d, J=8.4 Hz), 6.49 (1H, s), 6.04 (1H, s), 6.02 (1H, s), 5.37 (2H, broad s), 4.22 (1H, m), 2.79 (2H, d, J=5.4 Hz), 2.54 (3H, d, J=4.6 Hz).

EXAMPLE 43

(±)-5-(4-Aminophenyl)-7,8-dihydro-9H-1,3-dioxolo/4,5-h//2,3/benzodiazepine-8-carboxylic acid-/N-(4-morpholinoethyl)amide/

Solvent for crystallization: ethanol.
M.p.: 184–186° C.
Yield: 50%.
Analysis: for C₂₃H₂₇N₅O₄ (437.50)
calculated: C, 63.14%; H, 6.22%; N, 16.01%.
found: C, 62.44%; H, 6.18%; N, 15.81%.

¹H NMR/CDCl₃+(CD₃)₂SO/: δ7.31 (2H, d, J=8.7 Hz), 7.30 (1H, broad s), 6.70 (1H, s), 6.62 (2H, d, J=8.7 Hz), 6.58 (1H, s), 5.97 (2H, s), 5.83 (1H, broad s), 4.50 (2H, broad s), 4.45 (1H, m), 3.55 (4H, m), 3.32 (1H, m), 3.13 (1H, m), 2.96 (1H, dd, J=13.8 and 6.0 Hz), 2.88 (1H, dd, J=13.8 and 3.87 Hz), 2.25 (6H, m).

EXAMPLE 44

(±)-7-Acetyl-5-(4-Aminophenyl)-7,8-dihydro-9H-1,3-dioxolo/4,5-h//2,3/benzodiazepine-8-carboxylic amide Solvent for crystallization: ethanol.
M.p.: 214–242° C.
Yield: 74%.
Analysis: for C₁₉H₁₈N₄O₄ (366.38)
calculated: C, 62.29%; H, 4.95%; N, 15.29%.
found: C, 61.78%; H, 4.88%; N, 15.38%.

¹H NMR/(CD₃)₂SO/: δ7.34 (2H, d, J=8.6 Hz), 7.11 (2H, broad s), 6.99 (1H, s), 6.61 (1H, s), 6.60 (2H, d, J=8.6 Hz), 6.10 (1H, s), 6.07 (1H, s), 5.76 (2H, broad s), 5.23 (1H, dd, J=12.2 and 4.8 Hz), 3.04 (1H, dd, J=13.6 and 4.8 Hz), 2.75 (1H, t, J=12.6 Hz), 2.00 (3H, s).

EXAMPLE 45

(±)-7-Acetyl-5-(4-aminophenyl)-7,8-dihydro-9H-1,3-dioxolo/4,5-h//2,3/benzodiazepine-8-carboxylic acid-(N-methylamide)

Solvent for crystallization: acetonitrile.
M.p.: 164–167° C.
Yield: 63%.

Analysis: for C$_{20}$H$_{20}$N$_4$O$_4$ (380.41)
calculated: C, 63.15%; H, 5.30%; N, 14.73%.
found: C, 63.04%; H, 5.30%; N, 14.46%.

$^1$H NMR (CDCl$_3$): δ7.53 (2H, d, J=8.6 Hz), 6.81 (1H, 5), 6.69 (2H, d, J=8.6 Hz), 6.61 (1H, m), 6.60 (1H, s), 6.03 (1H, s), 6.02 (1H, s), 5.56 (1H, dd, J=11.8 and 7.0 Hz), 4.16 (2H, broad s), 3.05 (2H, m), 2.79 (3H, d, J=4.8 Hz), 2.05 (3H, s).

EXAMPLE 46

(±)-7-Acetyl-5-(4-aminophenyl)-7,8-dihydro-9H-1,3-dioxolo-/4,5-h//2,3/benzodiazepine-8-carboxylic acid-/N-(4-morpholinoethyl)amide/

Solvent for crystallization: acetonitrile.
M.p.: 200–202° C.
Yield: 75%.
Analysis: for C$_{25}$H$_{29}$N$_5$O$_5$ (479.54)
calculated: 62.62%; H, 6.10%; N, 14.60%.
found: 61.27%; H, 6.22%; N, 14.32%.

$^1$H NMR/(CD$_3$)$_2$SO/: δ7.50 (1H, t, J=5.2 Hz), 7.35 (2H, d, J=8.8 Hz), 7.00 (1H, s), 6.62 (1H, s), 6.61 (2H, d, J=8.8 Hz), 6.09 (1H, s), 6.06 (1H, s), 5.76 (2H, broad s), 5.24 (1H, dd, J=12.0 and 4.8 Hz), 3.56 (4H, m), 3.15 (2H, m), 3.02 (1H, dd, J=8.8 and 6.4 Hz), 2.75 (1H, t, J=12.8 Hz), 2.35 (4H, m), 2.01 (3H, s).

EXAMPLE 47

5-(4-Aminophenyl)-8-cyano-9H-1,3-dioxolo/4,5-h//2,3/benzodiazepine

Solvent for crystallization: acetonitrile.
M.p.: 245–248° C.
Yield: 59%.
Analysis: for C$_{17}$H$_{12}$N$_4$O$_2$ (304.31)
calculated: C, 67.10%; H, 3.97%; N, 18.41%.
found: C, 65.65%; H, 4.07%; N, 18.06%.

$^1$H NMR/(CD$_3$)$_2$SO/: δ7.32 (2H, d, J=8.6 Hz), 7.19 (1H, s), 6.82 (1H, s), 6.60 (2H, d, J=8.6 Hz), 6.17 (1H, s), 6.12 (1H, s), 5.82 (2H, broad s), 3.75 (1H, d, J=13.9 Hz), 3.12 (1H, d, J=13.9 Hz).

EXAMPLE 48

5-(4-Aminophenyl)-8-(5-tetrazolyl)-9H-1,3-dioxolo/4,5-h//2,3/benzodiazepine

Solvent for crystallization: acetonitrile.
M.p.: 244–246° C.
Yield: 67%.
Analysis: for C$_{17}$H$_{13}$N$_7$O$_2$ (347.34)
calculated: C, 58.79%; H, 3.77%; N, 28.23%.
found: C, 58.62%; H, 3.79%; N, 28.28%.

$^1$H NMR (CDCl$_3$): δ9.00 (3H, broad s), 7.39 (2H, d, J=8.6 Hz), 7.05 (1H, s), 6.81 (1H, s), 6.65 (2H, d, J=8.6 Hz), 6.14 (1H, s), 6.05 (1H, s), 4.30 (1H, d, J=13.2 Hz), 3.22 (1H, d, J=13.2 Hz).

EXAMPLE 49

5-(4-Aminophenyl)-8-(4-morpholinomethyl)-9H-1,3-dioxolo/4,5-h//2,3/benzodiazepine Solvent for crystallization: ethanol.
M.p.: 208–212° C.
Yield: 63%.

Analysis: for C$_{21}$H$_{22}$N$_4$O$_3$ (378.43)
calculated: C, 66.65%; H, 5.86%; N, 14.80%.
found: C, 65.06%; H, 5.83%; N, 14.35%.

$^1$H NMR/(CD$_3$)$_2$SO/: δ7.26 (2H, d, J=8.8 Hz), 6.98 (1H, s), 6.69 (1H, s), 6.58 (2H, d, J=8.8 Hz), 6.09 (1H, d, J=0.4 Hz), 6.04 (1H, d, J=0.8 Hz), 5.51 (2H, broad s), 3.55 (1H, d, J=12.0 Hz), 3.52 (4H, m), 3.15 (1H, d, J=12.9 Hz), 3.02 (1H, d, J=12.9 Hz), 2.68 (1H, d, J=12.0 Hz), 2.30 (2H, m), 2.10 (2H, m).

EXAMPLE 50

5-(4-Aminophenyl)-8-dimethylaminomethyl)-9H-1,3-dioxolo/4,5-h//2,3/benzodiazepine Solvent for crystallization: ethanol.
M.p.: 185–189° C.
Yield: 61%.
Analysis: for C$_{19}$H$_{20}$N$_4$O$_2$ (336.40)
calculated: C, 65.13%; H, 5.18%; N, 15.99%.
found: C, 65.54%; H, 5.22%; N, 15.53%.

$^1$H NMR (CDCl$_3$): δ7.48 (2H, d, J=8.4 Hz), 6.78 (1H, s), 6.75 (1H, s), 6.65 (2H, d, J=8.4 Hz), 6.00 (1H, d, J=1.2 Hz), 5.96 (1H, d, J=1.2 Hz), 3.93 (2H, broad s), 3.60 (1H, d, J=12.4 Hz), 3.18 (1H, d, J=13.2 Hz), 3.00 (1H, d, J=13.2 Hz), 2.85 (1H, d, J=12.4 Hz), 2.22 (6H, s).

EXAMPLE 51

8-(N-Acetyl-N-methylaminomethyl)-5-(4-aminophenyl)-9H-1,3-dioxolo/4,5-h//2,3/benzodiazepine Solvent for crystallization: acetonitrile.
M.p.: 129–133° C.
Yield: 69%.
Analysis: for C$_{20}$H$_{20}$N$_4$O$_3$ (364.41)
calculated: C, 65.92%; H, 5.53%; N, 15.37%.
found: C, 65.81%; H, 5.45%; N, 15.04%.

$^1$H NMR/(CD$_3$)$_2$SO/ (the product is a mixture of two conformers):

δ7.27 (2H, d, J=8.4 Hz), 6.99 (1H, s), 6.73 (1H, s), 6.59 (2H, d, J=8.4 Hz), 6.10 (2H, m), 5.54 (2H, broad s), 4.30 (1H, d, J=18 Hz), 4.14 (1H, d, J=18 Hz), 3.30 (1H, d, J=12.4 Hz), 2.75 (1H, d, J=12.4 Hz), 2.65 (3H, s), 1.75 (3H, s).

δ7.27 (2H, d, J=8.4 Hz), 6.83 (1H, s), 6.72 (1H, s), 6.59 (2H, d, J=8.4 Hz), 6.10 (2H, m), 5.54 (2H, broad s), 4.16 (2H, m), 3.30 (1H, d, J=12.4 Hz), 2.66 (1H, d, J=12.4 Hz), 2.71 (3H, s), 2.04 (3H, s).

EXAMPLE 52

Methyl 5-(4-aminophenyl)-9H-1,3-dioxolo/4,5-h//2,3/benzodiazepine-8-carboxylate

Solvent for crystallization: ethanol.
M.p.: 206–209° C.
Yield: 56%.
Analysis: for C$_{19}$H$_{17}$N$_3$O$_4$ (351.37)
calculated: C, 64.09%; H, 4.48%; N, 12.46%.
found: C, 64.32%; H, 4.48%; N, 12.54%.

$^1$H NMR/(CD$_3$)$_2$SO/: δ7.30 (2H, d, J=8.4 Hz), 6.94 (1H, s), 6.75 (1H, s), 6.59 (2H, d, J=8.4 Hz), 6.10 (1H, s), 6.04

(1H, s), 5.67 (2H, broad s), 3.93 (1H, d, J=13.0 Hz), 3.74 (3H, s), 2.74 (1H, d, J=13.0 Hz).

EXAMPLE 53

(±)-7-Acetyl-8-(acetyl-N-methylaminomethyl)-5-(4-aminophenyl)-7,8-dihydro-9H-1,3-dioxolo/4,5-h//2,3/benzodiazepine Solvent for crystallization: acetonitrile.

M.p.: 184–188° C.

Yield: 73%.

Analysis: for $C_{22}H_{24}N_4O_4$ (408.46)

calculated: C, 64.69%; H, 5.92%; N, 13.72%.

found: C, 64.42%; H, 5.99%; N, 13.43%.

$^1$H NMR (CDCl$_3$) (the product is a mixture of two conformers):

δ7.53 (2H, m), 6.78 (1H, s), 6.68 (2H, m), 6.60 (1H, s), 5.98 (2H, m), 5.38 (1H, m), 4.11 (2H, broad s), 3.96 (1H, dd, J=13.2 and 5.6 Hz), 3.72 (1H, dd, J=14.4 and 6.8 Hz), 3.02 (3H, s), 2.74 (2H, m), 2.22 (3H, s), 1.95 (3H, s).

δ7.53 (2H, m), 6.75 (1H, s), 6.68 (2H, m), 6.57 (1H, s), 5.98 (2H, m), 5.35 (1H, m), 4.11 (2H, broad s), 3.31 (1H, dd, J=13.6 and 6.0 Hz), 3.13 (3H, s), 2.74 (3H, m), 2.07 (3H, s), 1.97 (3H, s).

EXAMPLE 54

8-Acetoxymethyl-5-(4-aminophenyl)-9H-1,3-dioxolo/4,5-h//2,3/benzodiazepine

Solvent for crystallization: ethanol.

M.p.: 206–209° C.

Yield: 64%.

Analysis: for $C_{19}H_{17}N_3O_4$ (351.37)

calculated: C, 64.95%; H, 4.88%; N, 11.96%.

found: C, 64.59%; H, 4.98%; N, 11.70%.

$^1$H NMR/(CD$_3$)$_2$SO/: δ7.28 (2H, d, J=8.4 Hz), 7.01 (1H, s), 6.71 (1H, s), 6.59 (2H, d, J=8.4 Hz), 6.10 (1H, s), 6.08 (1H, s), 5.54 (2H, broad s), 4.76 (1H, d, J=14.0 Hz), 4.64 (1H, d, J=14.0 Hz), 3.44 (1H, d, J=12.8 Hz), 2.74 (1H, d, J=12.8 Hz), 2.07 (3H, s).

EXAMPLE 55

(±)-7-Acetyl-8-acetoxymethyl-5-(4-aminophenyl)-7,8-dihydro-9H-1,3-dioxolo/4,5-h//2,3/benzodiazepine Solvent for crystallization: ethanol.

M.p.: 199–205° C.

Yield: 66%.

Analysis: for $C_{21}H_{21}N_3O_5$ (395.42)

calculated: C, 63.79%; H, 5.35%; N, 10.63%.

found: C, 63.34%; H, 5.34%; N, 10.36%.

$^1$H NMR (CDCl$_3$): δ7.51 (2H, d, J=8.4 Hz), 6.78 (1H, s), 6.65 (2H, d, J=8.4 Hz), 6.59 (1H, s), 6.01 (1H, d, J=1.4 Hz), 5.97 (1H, d, J=1.4 Hz), 5.42 (1H, m), 4.35 (1H, dd, J=11.2 and 6.4 Hz), 4.12 (3H, m), 2.74 (2H, m), 2.04 (3H, 5), 2.01 (3H, s).

EXAMPLE 56

5-(4-Aminophenyl)-8-(1,5-diazabicyclo/4.3.0/non-5-enium-5-ylmethyl)-9H-1,3-dioxolo/4,5-h//2,3/benzodiazepine methanesulfonate Solvent for crystallization: acetonitrile.

M.p.: 178–182° C.

Yield: 66%

Analysis: for $C_{25}H_{29}N_5O_5S$ (511.60)

calculated: C, 58.69%; H, 5.71%; N, 13.69%. S, 6.27%.

found: C, 56.90%; H, 5.94%; N, 13.73%; S, 6.01%.

$^1$H NMR/(CD$_3$)$_2$SO/: δ7.28 (2H, d, J=8.5 Hz), 7.13 (1H, s), 6.75 (1H, s), 6.61 (2H, d, J=8.5 Hz), 6.13 (1H, s), 6.11 (1H, s), 5.65 (2H, broad s), 4.59 (1H, d, J=17.5 Hz), 4.36 (1H, d, J=17.5 Hz), 3.69 (2H, t, J=6.5 Hz), 3.42 (1H, d, J=12.7 Hz), 3.35 (2H, m), 3.28 (1H, m), 3.15 (1H, m), 2.90 (1H, m), 2.81 (1H, d, J=12.7 Hz), 2.60 (1H, m), 2.33 (3H, s), 1.98 (4H, m).

EXAMPLE 57

5-(4-Aminophenyl)-8-hydroxymethyl-9H-1,3-dioxolo/4,5-h//2,3/benzodiazepine 2.63 g (7.5 mmoles) of the acetoxy compound obtained in Example 54 are dissolved in 50 cm$^3$ of tetrahydrofuran. To the solution obtained, at first 50 cm$^3$ of water, then, under cooling with ice-water, 9 cm$^3$ (9.0 mmoles) of 1 n sodium hydroxide solution are added, drop by drop. The reaction mixture is stirred at room temperature for 1.5 hours, then extracted three times using 50 m$^3$ of ethyl acetate each time. The combined organic phases are washed with 30 cm$^3$ of saturated brine, dried over anhydrous magnesium sulfate, and evaporated under reduced pressure. The crude product obtained is recrystallized from 30 cm$^3$ of acetonitrile.

Thus, 1.79 g (77%) of the title compound are obtained.

M.p.: 250° C. (decomp.).

Analysis: for $C_{17}H_{15}N_3O_3$ (309.33)

calculated: C, 66.01%; H, 4.89%; N, 13.58%.

found: C, 65.52%; H, 4.95%; N, 13.18%.

$^1$H NMR/(CD$_3$)$_2$SO/: δ7.28 (2H, d, J=8.5 Hz), 6.96 (1H, s), 6.70 (1H, s), 6.60 (2H, d, J=8.5 Hz), 6.10 (1H, s), 6.05 (1H, s), 5.51 (2H, broad s), 5.20 (1H, t, J=6.0 Hz), 4.07 (2H, m), 3.56 (1H, d, J=12,4 Hz), 2.64 (1H, d, J=12.3 Hz).

EXAMPLE 58

(±)-8-Cyano-7,8-dihydro-8-methyl-5-(4-nitrophenyl)-9H-1,3-dioxolo/4,5-h//2,3/benzodiazepine 36.0 g (111.4 mmoles) of 8-methyl-5-(4-nitrophenyl)-9H-1,3-dioxolo/4,5-h//2,3/benzodiazepine and 180 cm$^3$ of glacial acetic acid are introduced into an acid-resistant steel bomb tube of 400 cm$^3$ capacity. To the suspension, 21.75 g (334.1 mmoles) of potassium cyanide are added at a temperature of 20 to 26° C. under cooling with ice-water in 20 minutes. The bomb tube is sealed and stirred at 70° C. for 22 hours. After cooling, the reaction mixture is stirred with 600 cm$^3$ of dichloromethane and 600 cm$^3$ of water, the phases are separated, the aqueous layer is further extracted twice using 300 cm$^3$ of dichloromethane each time, the combined organic phases are washed three times with 300 cm$^3$ of water each time, dried over anhydrous magnesium sulfate, and evaporated. The residue is crystallized from 250 cm$^3$ of ether, the crystals are filtered, and washed three times using 60 cm$^3$ of ether each time.

Thus, 33.6 g (86.0%) of the title compound are obtained.

M.p.: 162–164° C.

Analysis: for $C_{18}H_{14}N_4O_4$ (350.34)

calculated: N, 15.99%.

found: N, 15.62%.

$^1$H NMR (CDCl$_3$): δ8.23 (2H, d, J=8.9 Hz), 7.78 (2H, d, J=8.9 Hz), 6.84 (1H, s), 6.52 (1H, s), 6.05 (1H, d, J=1.3 Hz), 6.03 (1H, d, J=1.3 Hz), 5.58 (1H, s), 3.12 (1H, d, J=14.1 Hz), 2.83 (1H, d, J=14.1 Hz), 1.68 (3H, s).

EXAMPLE 59

(±)-7,8-Dihydro-8-methyl-5-(4-nitrophenyl)-9H-1,3-dioxolo/4,5-h//2,3/benzodiazepine-8-carboxamide 10.0 g (28.5 mmoles) of the compound prepared according to Example 58 are added to 90 cm$^3$ of concentrated hydrochloric acid at a temperature of −10 to −20° C. in 15 minutes, then the solution is allowed to warm to 25° C. The yellow solution is stirred at 25° C. for 18 hours. During this time, crystals precipitate. The mixture is evaporated under reduced pressure, to the residue, 50 cm$^3$ of ethanol are added, the mixture obtained is evaporated, and this process is repeated once more. The evaporation residue is dissolved in 55 cm$^3$ of ethanol, to the solution obtained, 80 cm$^3$ of ether are added. The yellow crystals precipitated are filtered, and washed three times using 10 cm$^3$ of ether each time.

Thus, 10.0 g (86.3%) of the hydrochloride of the title compound are obtained. M.p.: 182–184° C.

The hydrochloride is suspended in 80 cm$^3$ of water, and the pH is adjusted with 10% sodium hydroxide to a value of 10 at 5 to 10° C. After 10 minutes's stirring, the crystals are filtered, washed with ether and dried.

Thus, 6.6 g (62.7%) of the title compound are obtained. M.p.: 209–210° C.

Analysis: for $C_{18}H_{16}N_4O_5$ (368.35)

calculated: C, 58.69%; H, 4.38%; N, 15.21%.

found: C, 58.75%; H, 4.32%; N, 15.11%.

$^1$H NMR (CDCl$_3$): δ8.22 (2H, d, J=8.9 Hz), 7.69 (2H, d, J=8.9 Hz), 6.77 (1H, s), 6.67 (1H, bs), 6.45 (1H, s), 6.00 (1H, d, J=1.2 Hz), 5.98 (1H, d, J=1.2 Hz), 5.72 (1H, bs), 5.24 (1H, bs), 3.12 (1H, d, J=13.6 Hz), 2.83 (1H, d, J=13.6 Hz), 1.65 (3H, s).

EXAMPLE 60

(±)-7,8-Dihydro-8-methyl-5-(4-nitrophenyl)-9H-1,3-dioxolo/4,5-h//2,3/benzodiazepine-8-carboxylic acid 30.0 g (85.6 mmoles) of the compound prepared according to Example 58 are added to 450 cm$^3$ of concentrated hydrochloric acid at −10° C. in 10 minutes, and the solution is stirred at 25° C. for 18 days. The reaction mixture is evaporated under reduced pressure, to the evaporation residue, 200 cm$^3$ of ethanol are added, and the evaporation process is repeated. The evaporation residue is boiled in 180 cm$^3$ of ethanol for 5 minutes, then 200 cm$^3$ of ether are added under cooling with ice-water. The mixture is stirred at 10° C. for 60 minutes, the crystals precipitated are filtered, and washed three times using 30 cm$^3$ of ether each time. 17.6 g of the hydrochloride obtained are transferred to 70 cm$^3$ of water, and the suspension is made alkaline by the addition of 55 cm$^3$ of 10% sodium hydroxide solution. The solution obtained is extracted with 50 cm$^3$ of dichloromethane, the pH of the aqueous solution is adjusted with 10% hydrochloric acid to a value of 5, and the solution is extracted twice with 200 cm$^3$ of dichloromethane each time. The organic phase is dried, evaporated under reduced pressure, the evaporation residue is crystallized with 30 cm$^3$ of ether. The crystals are filtered, washed twice using 5 cm$^3$ of ether each time.

Thus, 6.7 g (21.1%) of the title compound are obtained. M.p.: 230–232° C.

Analysis: for $C_{18}H_{15}N_3O_6$ (369.32)

calculated: C, 58.53%; H, 4.09%; N, 11.38%.

found: C, 57.78%; H, 4.12%; N, 11.13%.

$^1$H NMR (DMSO-d$_6$): δ12.72 (1H, bs), 8.21 (2H, d, J=8.9 Hz), 7.68 (2H, d, J=8.9 Hz), 7.50 (1H, bs), 6.96 (1H, s), 6.50 (1H, s), 6.05 (2H, s), 3.02 (1H, d, J=13.8 Hz), 2.85 (1H, d, J=13.8 Hz), 1.39 (3H, s).

EXAMPLE 61

(±)-7-Acetyl-8-cyano-7,8-dihydro-8-methyl-5-(4-nitrophenyl)-9H-1,3-dioxolo/4,5-h//2,3/benzodiazepine 10.51 g (30 mmoles) of the compound prepared according to Example 58 are added to 44 cm$^3$ of acetyl chloride, and the reaction mixture is stirred at 10° C. for an hour. The reaction mixture is allowed to warm to room temperature, and stirred at 25° C. for further 3 days, then evaporated under reduced pressure. To the evaporation residue, 250 cm$^3$ of water are added, and the mixture is stirred for half an hour under cooling with ice-water. The crystals obtained are filtered, washed three times using 20 cm$^3$ of cold water each time, and dried under a lamp emitting infra red radiation. 11.2 g (95.1%) of the crude product obtained are suspended in 20 cm$^3$ of ethanol, stirred for half an hour, then filtered. The crystals are washed twice with 10 cm$^3$ of ethanol each time, and once with 25 cm$^3$ of ether. After drying, 9.5 g (80.7%) of the title compound are obtained, m.p.: 289–292° C.

Analysis: for $C_{20}H_{16}N_4O_5$ (392.37)

calculated: C, 61.22%; H, 4.11%; N, 14.28%.

found: C, 60.85%; H, 4.18%; N, 13.98%.

$^1$H NMR (CDCl$_3$): δ8.29 (2H, d, J=9.0 Hz), 7.83 (2H, d, J=9.0 Hz), 6.99 (1H, s), 6.51 (1H, s), 6.10 (1H, d, J=1.2 Hz), 6.07 (1H, d, J=1.2 Hz), 3.11 (2H, m), 2.30 (3H, s), 1.84 (3H, s).

EXAMPLE 62

(±)-7-Acetyl-7,8-dihydro-8-methyl-5-(4-nitrophenyl)-9H-1,3-dioxolo/4,5-h//2,3/benzodiazepine-8-carboxamide 9.8 g (24.98 mmoles) of the compound prepared according to Example 61 are added to 130 cm$^3$ of concentrated hydrochloric acid. The reaction mixture is stirred at 5 to 10° C. for 2 hours, then at 25° C. for an hour, and evaporated under reduced pressure. To the evaporation residue, 120 cm$^3$ of ethanol are added, and the solution is evaporated again. To the evaporation residue, 150 cm$^3$ of water are added. After 30 minutes's stirring, the crystals are filtered, washed three times with 10 cm$^3$ of water each time, twice with diisopropyl ether, and dried under a lamp emitting infra red radiation. 9.4 g (91.7%) of the crude product obtained are transferred to a silica gel column that is eluted with ethyl acetate. The adequate fraction is evaporated, the evaporation residue is rubbed with ether, the crystals obtained are filtered, and washed with ether.

Thus, 4.5 g (43.9%) of the title compound are obtained. M.p.: 183–184.5° C.

Analysis: for $C_{20}H_{18}N_4O_6$ (410.39)

calculated: C, 58.53%; H, 4.42%; N, 13.65%.

found: C, 58.70%; H, 4.52%; N, 13.21%.

$^1$H NMR (DMSO-d$_6$): δ8.30 (2H, d, J=8.8 Hz), 7.79 (2H, d, J=8.8 Hz), 7.03 (1H, s), 6.89 (2H, bs), 6.56 (1H, s), 6.11 (1H, s), 3.09 (1H, d, J=14.2 Hz), 2.83. (H, d, J=14.2 Hz), 2.27 (3H, s), 1.43 (3H, s).

EXAMPLE 63

(±)-8-Cyano-7,8-dihydro-8-methyl-5-(4-nitrophenyl)-7-trichloroacetyl-9H-1,3-dioxolo/4,5-h//2,3/benzodiazepine 3.5 g (10 mmoles) of the compound prepared according to Example 58 are transferred to 20 cm³ of chloroform. To the suspension cooled with ice-water, 2.46 cm³ (22 mmoles) of trichloroacetyl chloride are added, drop by drop, in 5 minutes, then, 1.53 cm³ (11 mmoles) of triethylamine are added, drop by drop, in 10 minutes. The reaction mixture is stirred at 5 to 10° C. for 2 hours, then at 25° C. for 19 hours, then poured into 150 cm³ of ice-water. After 60 minutes' stirring, the layers are separated, the product is extracted with chloroform, the organic phase is dried over anhydrous magnesium sulfate, and evaporated. The evaporation residue is crystallized from ether, the crystals are stirred for half an hour, and filtered. 3.0 g (60.6%) of the crude product obtained are recrystallized from 25 cm³ of ethanol, filtered, washed with ethanol and ether.

Thus, 2.6 g (52.5%) of the title compound are obtained. M.p.: 254–255.4° C.

Analysis: for $C_{20}H_{13}Cl_3N_4O_5$ (495.70)

calculated: C, 48.46%; H, 2.64%; N, 11.30%.

found: C, 48.57%; H, 2.65%; N, 11.10%.

$^1$H NMR (CDCl$_3$): δ8.32 (2H, d, J=8.6 Hz), 7.98 (2H, d, J=8.6 Hz), 7.06 (1H, s), 6.50 (1H, s), 6.13 (1H, s), 6.09 (1H, s), 3.13 (2H, m), 1.93 (3H, s).

EXAMPLE 64

(±)-8-Cyano-7,8-dihydro-8-methyl-5-(4-nitrophenyl)-7-trifluoroacetyl-9H-1,3-dioxolo/4,5-h//2,3/benzodiazepine 8.76 g (25 mmoles) of the compound prepared according to Example 58 are dissolved in 60 cm³ of chloroform. To the solution, 6.5 cm³ (46 mmoles) of trifluoroacetic anhydride are added, drop by drop, under cooling with icewater at 5 to 10° C. in 10 minutes. The mixture is stirred at 10° C. for 2 hours, at 25° C. for 25 hours, then poured into 300 cm³ of ice-water. The layers are separated, the aqueous phase is extracted twice using 100 cm³ of chloroform each time. The organic phase is dried, then evaporated. The evaporation residue is crystallized in 70 cm³ of ether. After 60 minutes' stirring, the crystals are filtered, and washed three times using 100 cm³ of ether each time.

Thus, 8.6 g (77.1%) of the title compound are obtained. M.p.: 231–234° C.

Analysis: for $C_{20}H_{13}F_3N_4O_5$ (446.33)

calculated: C, 53.82%; H, 2.94%; N, 12.55%.

found: C, 54.09%; H, 2.94%; N, 12.32%.

$^1$H NMR (DMSO-d$_6$): δ8.38 (2H, d, J=8.6 Hz), 7.86 (2H, d, J=8.6 Hz), 7.28 (1H, s), 6.76 (1H, s), 6.19 (2H), 3.44 (2H, m), 1.89 (3H, s).

EXAMPLE 65

(±)-7,8-Dihydro-8-methyl-5-(4-nitrophenyl)-7-trifluoroacetyl-9H-1,3-dioxolo/4,5-h//2,3/benzodiazepine-8-carboxylic acid 5.6 g (15.2 mmoles) of the compound prepared according to Example 60 are suspended in chloroform. To the suspension, 4.0 cm³ (28.3 mmoles) of trifluoroacetic anhydride are added, drop by drop, under cooling with ice-water at 10° C. in 10 minutes. The mixture is stirred at 10° C. for 2 hours, at 25° C. for 20 hours, then poured unto 130 g of crushed ice. After 60 minutes' stirring, the crystals are filtered, washed three times with 30 cm³ of chloroform each time, and once with 50 cm³ of ether.

Thus, 3.76 g (53.3%) of the title compound are obtained. M.p.: 160–162° C.

Analysis: for $C_{20}H_{14}F_3N_3O_7$ (465.33)

calculated: C, 51.62%; H, 3.03%; N, 9.03%.

found: C, 51.69%; H, 3.05%; N, 8.91%.

$^1$H NMR (DMSO-d$_6$): δ8.39 (2H, d, J=8.6 Hz), 7.67 (2H, bs), 7.25 (1H, s), 6.39 (1H, s), 6.17 (2H), 3.64 (1H, d, J=17.4 Hz), 3.50 (1H, d, J=17.4 Hz), 1.67 (3H, s).

EXAMPLE 66

(±)-8-Cyano-7,8-dihydro-7-formyl-5-(4-nitrophenyl)-9H-1,3-dioxolo/4,5-h//2,3/benzodiazepine 5.0 g (14.27 mmoles) of the compound prepared according to Example 58 are added to 40.0 cm³ (539.6 mmoles) of a mixed anhydride of formic acid and acetic acid at 5° C. in 5 minutes. The reaction mixture is stirred at 5 to 10° C. for an hour, at 25° C. for 17 hours, then poured onto 100 g of ice. After one hour's stirring, the crystals are filtered, washed three times with 20 cm³ of water each time, once with 20 cm³ of ether, and dried under a lamp emitting infra red radiation.

Thus, 4.0 g (74.1%) of the title compound are obtained. M.p.: 230.7–232.5° C.

Analysis: for $C_{19}H_{14}N_4O_5$ (378.35)

calculated: C, 60.32%; H, 3.73%; N, 14.81%.

found: C, 59.85%; H, 3.80%; N, 14.88%.

$^1$H NMR (CDCl$_3$): δ8.65 (1H, s), 8.28 (2H, d, J=8.8 Hz), 7.83 (2H, d, J=8.8 Hz), 6.96 (1H, s), 6.51 (1H, s), 6.10 (1H, d, J=1.3 Hz), 6.08 (1H, d, J=1.3 Hz), 3.26 (1H, d, J=14.4 Hz), 3.16 (1H, d, J=14.4 Hz), 1.87 (3H, s).

EXAMPLE 67

(±)-8-Cyano-7,8-dihydro-8-methyl-5-(4-nitrophenyl)-7-propionyl-9H-1,3-dioxolo/4,5-h//2,3/benzodiazepine 5.0 g (14.27 mmoles) of the compound prepared according to Example 58 are added to 15 cm³ of propionyl chloride at 5 to 10° C. in 10 minutes. The reaction mixture is stirred at 5 to 10° C. for half an hour, at 25° C. for 23 hours, then evaporated. To the evaporation residue, 30 cm³ of ether are added, and the suspension is stirred for 30 minutes. The crystals are filtered, washed three times using 10 cm³ of ether each time, and dried under a lamp emitting infra red radiation.

Thus, 5.1 g (88.0%) of the title compound are obtained. M.p.: 216–218° C.

$^1$H NMR (CDCl$_3$): δ8.30 (2H, d, J=9.0 Hz), 7.83 (2H, d, J=9.0 Hz), 6.99 (1H, s), 6.51 (1H, s), 6.10 (1H, d, J=1.3 Hz), 6.06 (1H, d, J=1.3 Hz), 3.12 (1H, d, J=14.4 Hz), 3.08 (1H, d, J=14.4 Hz), 2.75–2.43 (2H, m), 1.84 (3H, s), 1.17 (3H, t, J=7.4 Hz).

EXAMPLE 68

(±)-7-Butyryl-8-cyano-7,8-dihydro-8-methyl-5-(4-nitrophenyl)-9H-1,3-dioxolo/4,5-h//2,3/benzodiazepine 5.0 g (14.27 mmoles) of the compound prepared according to Example 58 are added to 15 cm³ of butyric chloride at 5 to 10° C. in 20 minutes. The reaction mixture is stirred at 5 to 10° C. for 2 hours, then at 25° C. for 2 weeks. The suspension is filtered, the crystals are washed three times using 20 cm³ of ether each time, and dried under a lamp emitting infra red radiation.

Thus, 4.6 g (76.8%) of the title compound are obtained. M.p.: 248–250° C.

¹H NMR: δ8.30 (2H, d, J=8.9 Hz), 7.83 (2H, d, J=8.9 Hz), 6.99 (1H, s), 6.51 (1H, s), 6.09 (1H, d, J=1.3 Hz), 6.06 (1H, d, J=1.3 Hz), 3.13 (1H, d, J=14.5 Hz), 3.07 (1H, d, J=14.5 Hz), 2.56–1.69 (4H, m), 1.84 (3H, s), 0.99 (3H, t, J=7.4 Hz).

EXAMPLE 69

(±)-8-Cyano-7,8-dihydro-8-methyl-5-(4-nitrophenyl)-7-(pyridine-3-carbonyl)-9H-1,3-dioxolo/4,5-h//2,3/benzodiazepine 5.0 g (14.27 mmoles) of the compound prepared according to Example 58 are dissolved in a mixture of 50 cm³ of pyridine and 25.2 cm³ (181.8 mmoles) of triethylamine. To the solution obtained, 12.7 g (71.3 mmoles) of nicotinic acid chloride hydrochloride are added at 0 to 2° C. in 20 minutes, and the mixture is stirred at 25° C. for 2 days. Then, 15 cm³ of pyridine are added to the solution that is cooled to 5° C., and further 10.2 g (57.3 mmoles) of nicotinic acid chloride are added, and the mixture is stirred at 25° C. for further 7 days. Then, 200 cm³ of water are added to the mixture, drop by drop, at 5 to 10° C., the crystals are filtered, washed three times with 50 cm³ of water each time, and dried under a lamp emitting infra red radiation. The 6.4 g (98.5%) of the crude product obtained is transferred to a silica gel column that is eluted with a mixture of cyclohexane and ethyl acetate in a ratio of 1:1. The adequate fraction is evaporated, the evaporation residue is crystallized from ether. The crystals are filtered, and washed with ether.

Thus, 1.7 g (26.2%) of the title compound are obtained. M.p.: 246–248° C.

Analysis: for $C_{24}H_{17}N_5O_5$ (455.43)
calculated: C, 63.30%; H, 3.76%; N, 15.38%.
found: C, 63.32%; H, 3.74%; N, 14.96%.

¹H NMR (CDCl₃+DMSO-d₆): δ8.68 (1H, dd, J=4.9 and 1.7 Hz), 8.54 (1H, d, J=2.0 Hz), 8.12 (2H, d, J=8.9 Hz), 7.75 (1H, dt, J=7.9 and 1.9 Hz), 7.46–7.38 (1H, m), 7.40 (2H, d, J=8.9 Hz), 7.15 (1H, s), 6.67 (1H, s), 6.12 (1H, s), 6.11 (1H, s), 3.27 (1H, d, J=14.4 Hz), 3.20 (1H, d, J=14.4 Hz), 1.91 (3H, s).

EXAMPLE 70

(±)-8-Cyano-7,8-dihydro-8-methyl-5-(4-nitrophenyl)-9H-1,3-dioxolo/4,5-h//2,3/benzodiazepine-7-carboxylic acid-(dimethylamide)

10.5 g (30 mmoles) of the compound prepared according to Example 58 are dissolved in 100 cm³ of absolute pyridine. To the solution obtained, 15.6 g (100 mmoles) of phenyl chloroformate are added, drop by drop, at 0° C. in 20 minutes. The reaction mixture is stirred at 0° C. for 120 minutes, at 10° C. for 90 minutes, at 25° C. for 20 hours, and evaporated under reduced pressure. To the evaporation residue, 100 cm³ of benzene are added, the crystals precipitated are filtered, and washed three times using 40 cm³ of benzene each time. The filtrate is evaporated under reduced pressure to obtain 13.0 g of residue.

7.8 g of the evaporation residue obtained as described above, 80 cm³ of ethanol, 8.11 g (99.5 mmoles) of dimethylamine hydrochloride and 10.06 g (99.5 mmoles) of triethylamine are transferred into a bomb tube that is sealed, and the contents are stirred at 90° C. for 18 hours. The mixture is cooled, and concentrated to the half of its volume under reduced pressure. The suspension is stirred at 5 to 10° C. for 30 minutes, the crystals are filtered, washed three times with 20 cm³ of ether each time, three times with 10 cm³ of water each time, and again three times with 20 cm³ of ether each time, and dried under a lamp emitting infra red radiation.

Thus, 3.3 g (39.0%) of the title product are obtained. M.p.: 214–217° C.

EXAMPLE 71

(±)-8-Cyano-7,8-dihydro-8-methyl-7-(morpholine-4-carbonyl)-5-(4-nitrophenyl)-9H-1,3-dioxolo/4,5-h//2, 3/benzodiazepine 10.5 g (30 mmoles) of the compound prepared according to Example 58 are dissolved in 100 cm³ of absolute pyridine, and, to the solution obtained, 15.6 g (100 mmoles) of phenyl chloroformate are added, drop by drop, at I° C. in 20 minutes. The reaction mixture is stirred at 0° C. for 120 minutes, at 10° C. for 90 minutes, at 25° C. for 20 hours, and evaporated under reduced pressure. To the evaporation residue, 100 cm³ of benzene are added, the crystals precipitated are filtered, and washed three times using 40 cm³ of benzene each time. The filtrate is evaporated under reduced pressure, the evaporation residue amounts to 13.0 g.

The evaporation residue obtained as described above is dissolved in 100 cm³ of ethanol, and 7.2 cm³ (83 mmoles) of morpholine are added to the solution. The mixture is boiled for 23 hours, then cooled with ice-water, and stirred at 5 to 10° C. for half an hour. The crystals obtained are filtered, and washed three times using 40 cm³ of ether each time.

Thus, 6.3 g (45.4%) of the title compound are obtained. M.p.: 234–236° C.

¹H NMR (CDCl₃): δ8.29 (2H, d, J=8.8 Hz), 7.91 (2H, d, J=8.8 Hz), 6.94 (1H, s), 6.54 (1H, s), 6.10 (2H, s), 3.60 (4H, m), 3.31 (2H, m), 3.22 (2H, m), 3.17 (1H, d, J=14.4 Hz), 2.85 (1H, d, J=14.4 Hz), 1.79 (3H, s).

EXAMPLE 72

(±)-8-Cyano-7,8-dihydro-8-methyl-5-(4-nitrophenyl)-7-(pyrrolidine-1-carbonyl)-9H-1,3-dioxolo/4,5-h//2,3/benzodiazepine 10.5 g (30 mmoles) of the compound prepared according to Example 58 are dissolved in 100 cm³ of absolute pyridine, and, to the solution obtained, 15.6 g (100 mmoles) of phenyl chloroformate are added, drop by drop, at I° C. in 20 minutes. The reaction mixture is stirred at 0° C. for 120 minutes, at 10° C. for 90 minutes, at 25° C. for 20 hours, and evaporated under reduced pressure. To the evaporation residue, 100 cm³ of benzene are added, the crystals precipitated are filtered, and washed three times using 40 cm³ of benzene each time. The filtrate is evaporated under reduced pressure, the evaporation residue amounts to 13.0 g.

13.0 g of the evaporation residue obtained as described above are transferred into the bomb tube, then 55 cm³ of ethanol and 13.8 cm³ (166.9 mmoles) of pyrrolidine are added. The bomb tube is sealed, and the contents is stirred at 110° C. for 8.5 hours, then at 25° C. for 16 hours. The crystals obtained are filtered, and washed three times using 100 cm³ of ether each time.

Thus, 8.4 g (62.6%) of the title compound are obtained. M.p.: 270–272° C.

Analysis: for C$_{23}$H$_{21}$N$_5$O$_5$ (447.45)
calculated: C, 61.74%; H, 4.73%; N, 15.65%.
found: C, 63.01%; H, 4.81%; N, 15.23%.

$^1$H NMR (CDCl$_3$): δ8.28 (2H, d, J=7.8 Hz), 7.95 (2H, d, J=7.8 Hz), 6.96 (1H, s), 6.57 (1H, s), 6.10 (2H, s), 3.20 (4H, m), 3.13 (1H, d, J=13.8 Hz), 2.82 (1H, d, J=13.8 Hz), 1.84 (7H, m).

EXAMPLE 73

(±)-8-Cyano-7,8-dihydro-7-chloroacetyl-8-methyl-5-(4-nitrophenyl)-9H-1,3-dioxolo/4,5-h//2,3/benzodiazepine 15.6 g (44.5 mmoles) of the compound prepared according to Example 58 are added to 60 cm$^3$ (752.8 mmoles) of chloroacetyl chloride under stirring at 5 to 10° C. in 10 minutes. The mixture is stirred at 5 to 10° C. for an hour, at 25° C. for 47 hours, then poured into 500 cm$^3$ of ice-water. The mixture obtained is extracted three times using 100 cm$^3$ of dichloromethane each time, the organic phase is dried over anhydrous magnesium sulfate, and evaporated. The evaporation residue is crystallized from ether, after half an hour's stirring, the crystals are filtered, then dissolved in 380 cm$^3$ of hot acetone, precipitated with hot petroleum ether, and filtered.

Thus, 6.1 g (32.1%) of the title compound are obtained. M.p.: 231–233° C.

Analysis: for C$_{20}$H$_{15}$ClN$_4$O$_5$ (426.82)
calculated: C, 56.28%; H, 3.54%; Cl, 8.31%. N, 13.13%.
found: C, 55.54%; H, 3.67%; Cl, 8.10%; N, 12.73%.

$^1$H NMR (CDCl$_3$): δ8.30 (2H, d, J=8.9 Hz), 7.81 (2H, d, J=8.9 Hz), 6.99 (1H, s), 6.50 (1H, s), 6.11 (1H, d, J=1.3 Hz), 6.08 (1H, d, J=1.3 Hz), 4.43 (1H, d, J=13.7 Hz), 4.36 (1H, d, J=13.7 Hz), 3.18 (1H, d, J=14.5 Hz), 3.11 (1H, d, J=14.5 Hz), 1.87 (3H, s).

EXAMPLE 74

(±)-8-Cyano-7,8-dihydro-8-methyl-7-morpholinoacetyl-5-(4-nitrophenyl)-9H-1,3-dioxolo/4,5-h//2,3/benzodiazepine To 5.0 g (11.7 mmoles) of the compound prepared according to Example 73, 70 cm$^3$ of acetonitrile and 2.18 g (25 mmoles) of morpholine are added. The reaction mixture is boiled for 4 hours, cooled, the crystals are filtered, washed with ether. The filtrate is evaporated under reduced pressure, to the evaporation residue, 50 cm$^3$ of water are added. After an hour's stirring, the crystals are filtered, and washed three times using 15 cm$^3$ of water each time.

Thus, 5.2 g (93.0%) of the title compound are obtained. M.p.: 121–123° C.

$^1$H NMR (CDCl$_3$): δ8.31 (2H, d, J=9.0 Hz), 7.82 (2H, d, J=9.0 Hz), 7.01 (1H, s), 6.53 (1H, s), 6.11 (1H, d, J=1.1 Hz), 6.08 (1H, d, J=1.1 Hz), 4.00–3.25 (2H, m), 3.73 (4H, t, J=4.6 Hz), 3.62 (1H, d, J=16.7 Hz), 3.35 (1H, d, J=16.7 Hz), 2.64 (4H, m), 1.87 (3H, m).

EXAMPLE 75

(±)-8-Cyano-7,8-dihydro-7-[2-/2-(3,4-dimethoxyphenyl)-N-methylethylamino/acetyl]-8-methyl-5-(4-nitrophenyl)-9H-1,3-dioxolo/4,5-h//2,3/benzodiazepine To 11.35 g (26.6 mmoles) of the compound prepared according to Example 73, 130 cm$^3$ of acetonitrile and 10.4 g (53.3 mmoles) of 2-(3,4-dimethoxyphenyl)-N-methylethylamine are added. The reaction mixture is boiled for 5.5 hours, then evaporated. The residue is stirred in 100 cm$^3$ of water at 25° C. for 3 hours, then the crystals are filtered, and washed with water.

Thus, 15.2 g (97.6%) of the title compound are obtained. M.p.: 138–140° C.

$^1$H NMR (CDCl$_3$): δ8.28 (2H, d, J=8.9 Hz), 7.79 (2H, d, J=8.9 Hz), 6.99 (1H, s), 6.74 (3H, m), 6.48 (1H, s), 6.09 (1H, d, J=1.1 Hz), 6.05 (1H, d, J=1.1 Hz), 3.86 (3H, s), 3.83 (3H, s), 3.77 (1H, d, J=17.1 Hz), 3.55 (1H, d, J=17.1 Hz), 3.09 (2H, s), 2.8 (4H, m), 2.54 (3H, s), 1.86 (3H, s).

EXAMPLE 76

(±)-8-Cyano-7,8-dihydro-8-methyl-5-(4-nitrophenyl)-7-(3-chloropropionyl)-9H-1,3-dioxolo/4,5-h//2,3/benzodiazepine 15.6 g (44.5 mmoles) of the compound prepared according to Example 58 are added to 60 cm$^3$ (616 mmoles) of 3-chloropropionyl chloride under stirring at 5 to 10° C. in 15 minutes. The mixture is stirred at 5 to 10° C. for an hour, at 25° C. for 6 days, then poured onto 300 cm$^3$ of crushed ice. The mixture is stirred for 100 minutes, then extracted three times using 300 cm$^3$ of dichloromethane each time. The organic phase is washed with 100 cm$^3$ of 5% aqueous sodium hydroxide solution and 100 cm$^3$ of water, dried over anhydrous magnesium sulfate, and evaporated. The evaporation residue is boiled with 150 cm$^3$ of ethanol, cooled, and the crystals formed are filtered.

Thus, 10.7 g (54.6%) of the title compound are obtained. M.p.: 216–218° C.

Analysis: for C$_{21}$H$_{17}$ClN$_4$O$_5$ (440.85)
calculated: C, 57.22%; H, 3.89%; Cl, 8.04%. N, 12.71%.
found: C, 57.10%; H, 4.10%; Cl, 8.02%; N, 12.41%.

$^1$H NMR (DMSO-d$_6$): δ8.34 (2H, d, J=8.8 Hz), 7.87 (2H, d, J=8.8 Hz), 7.21 (1H, s), 6.69 (1H, s), 6.16 (1H, s), 6.15 (1H, s), 3.83 (2H, m), 3.50–2.90 (4H, m), 1.75 (3H, s).

EXAMPLE 77

(±)-8-Cyano-7,8-dihydro-8-methyl-7-[3-/4-(2-methoxyphenyl)piperazinyl/propionyl]-5-(4-nitrophenyl)-9H-1,3-dioxolo/4,5-h//2,3/benzodiazepine To 5.95 g (13.5 mmoles) of the compound prepared according to Example 76, 100 cm$^3$ of acetonitrile and 5.1 g (26.5 mmoles) of (2-methoxyphenyl)piperazine are added. The reaction mixture is boiled for 3 hours, cooled, filtered, the solids are washed with water and ether. The crude product is boiled in 80 cm$^3$ of ethanol, cooled, and filtered.

Thus, 4.8 g (59.6%) of the title compound are obtained. M.p.: 222–223.5° C.

Analysis: for C$_{32}$H$_{32}$N$_6$O$_6$ (596.65)
calculated: C, 64.42%; H, 5.41%; N, 14.09%.
found: C, 64.78%; H, 5.45%; N, 14.08%.

$^1$H NMR (CDCl$_3$): δ8.29 (2H, d, J=9.0 Hz), 7.86 (2H, d, J=9.0 Hz), 7.10–6.80 (5H, m), 6.51 (1H, s), 6.09 (1H, d, J=1.2 Hz), 6.05 (1H, d, J=1.2 Hz), 3.86 (3H, s), 3.30–2.60 (14H, m), 1.85 (3H, s).

EXAMPLE 78

(±)-8-Cyano-7,8-dihydro-7-[3-/2-(3,4-dimethoxyphenyl)-N-methylethylamino/propionyl]-8-methyl-5-(4-nitrophenyl)-9H-1,3-dioxolo/4,5-h//2,3/benzodiazepine To 6.17 g (14 mmoles) of the compound prepared according to Example 76, 70 cm$^3$ of acetonitrile and 5.48 g (28 mmoles) of 2-(3,4-dimethoxyphenyl)-N-methylethylamine are added. The reaction mixture is boiled for 5.5 hours, then evaporated. The residue is stirred in 50 cm³ of water at 25° C. for 60 minutes, the crystals are filtered. The crude product filtered is heated in 100 cm³ of water to boiling, then cooled, the crystals are filtered, washed with water and petroleum ether.

Thus, 7.1 g (81.6%) of the title compound are obtained. M.p.: 96–98° C.

Analysis: for $C_{32}H_{33}N_5O_7$ (599.65)

calculated: N, 11.68%.

found: N, 11.22%.

$^1$H NMR (CDCl$_3$): δ8.27 (2H, d, J=8.8 Hz), 7.85 (2H, d, J=8.8 Hz), 6.99 (1H, s), 7.85–7.65 (3H, m), 6.50 (1H, s), 6.08 (1H, s), 6.05 (1H, s), 3.86 (3H, s), 3.85 (3H, s), 3.20–2.60 (10H, m), 2.41 (3H, s), 1.83 (3H, s).

EXAMPLE 79

(±)-7-/3-(N-Benzyl-2-morpholinoethylamino) propionyl/-8-cyano-7,8-dihydro-8-methyl-5-(4-nitrophenyl)-9H-1,3-dioxolo/4,5-h//2,3/ benzodiazepine To 20 g (45.3 mmoles) of the compound prepared according to Example 76, 500 cm³ of acetonitrile and 25.66 g (113 mmoles) of N-benzyl-2-morpholinoethylamine are added.

The reaction mixture is boiled for 6 hours, then allowed to stand at 25° C. for 12 hours. The N-benzyl-2-morpholinoethylamine hydrochloride precipitated is filtered, and the filtrate is evaporated. The evaporation residue is stirred in 300 cm³ of water at 25° C. for 18 hours, the crystals are filtered, and washed with water. The crude product is transferred to a silica gel column that is eluted with a mixture of hexane, acetone and methanol in a ratio of 1:3:0.1. The adequate fraction is evaporated, the residue is suspended in water, and filtered.

Thus, 15.5 g (54.8%) of the title compound are obtained. M.p.: 78–79° C.

Analysis: for $C_{34}H_{36}N_6O_6$ (624.70):

calculated: N, 13.45%.

found: N, 12.93%.

$^1$H NMR (CDCl$_3$): δ8.26 (2H, d, J=8.9 Hz), 7.75 (2H, d, J=8.9 Hz), 7.35–7.15 (5H, m), 6.99 (1H, s), 6.40 (1H, s), 6.10 (1H, d, J=1.2 Hz), 6.06 (1H, d, J=1.2 Hz), 3.70–3.59 (6H, m), 3.08 (2H, m), 2.95–2.60 (6H, m), 2.55–2.30 (6H, m), 1.83 (3H, s).

EXAMPLE 80

(±)-8-Cyano-7,8-dihydro-7-[3-/4-(2-fluorophenyl) piperazinyl/propionyl]-8-methyl-5-(4-nitrophenyl)-9H-1,3-dioxolo/4,5-h//2,3/benzodiazepine To 5.5 g (12.48 mmoles) of the compound prepared according to Example 76, 75 cm³ of acetonitrile and 4.0 g (22.19 mmoles) of 2-fluorophenyl-piperazine are added. The reaction mixture is boiled for 7.5 hours, then allowed to stand for 12 hours. The crystals precipitated are filtered, washed with water and ether. The crude product is dissolved in 250 cm³ of toluene, and precipitated with 150 cm³ of petroleum ether, the crystals are filtered.

Thus, 3.96 g (54.3%) of the title compound are obtained. M.p.: 191–192° C.

Analysis: for $C_{31}H_{29}FN_6O_5$ (584.61)

calculated: N, 14.38%.

found: N, 14.11%.

$^1$H NMR (CDCl$_3$): δ8.$_{29}$ (2H, d, J=8.8 Hz), 7.86 (2H, d, J=8.8 Hz), 7.20–6.80 (5H, m), 6.51 (1H, s), 6.09 (1H, d, J=1.2 Hz), 6.05 (1H, d, J=1.2 Hz), 3.30–3.05 (6H, m), 3.05–2.60 (8H, m), 1.85 (3H, s).

EXAMPLE 81

(±)-7-Acetyl-5-(4-aminophenyl)-8-cyano-7,8-dihydro-8-methyl--9H-1,3-dioxolo/4,5-h//2,3/ benzodiazepine 18.3 g (46.6 mmoles) of the compound prepared according to Example 61 are suspended in a mixture of 370 cm³ of ethanol and 90 cm³ of water. To the suspension, 3.7 g 10% palladium/carbon catalyst are added, then 46.7 cm³ (941.7 mmoles) of 98% hydrazine hydrate are added in 20 minutes while the temperature of the reaction mixture reaches 40° C. and the starting compound dissolves. The mixture is stirred for 2.5 hours at room temperature. During this time, the reaction mixture cools to 25° C., and the product precipitates. The catalyst is filtered, washed twice with 200 cm³ of ethanol each time, then three times using 500 cm³ of chloroform each time. The filtrate is under reduced pressure, and 300 cm³ of water are added to the crystalline residue. After 1 hour's stirring, the crystals are filtered, washed three times using 70 cm³ of water each time, and twice using 50 cm³ of ether each time. The 14.0 g (82.8%) of the crude product are recrystallized from 420 cm³ of ethyl acetate, the crystals are filtered, washed three times with 30 cm³ of ether each time, and dried under a lamp emitting infra red radiation.

Thus, 10.5 g (62.1%) of the title compound are obtained. M.p.: 162–164° C.

Analysis: for $C_{20}H_{18}N_4O_3$ (362.39).

calculated: C, 66.28%; H, 5.01%; N, 15.46%.

found: C, 66.88%; H, 5.12%; N, 14.78%.

$^1$H NMR (CDCl$_3$): δ7.46 (2H, d, J=8.7 Hz), 6.96 (1H, s), 6.67 (2H, d, J=8.7 Hz), 6.65 (1H, s), 6.05 (1H, d, J=1.2 Hz), 6.01 (1H, d, J=1.2 Hz), 4.15 (2H, bs), 3.05 (1H, d, J=13.9 Hz), 2.92 (1H, d, J=13.9 Hz), 2.16 (3H, s), 1.81 (3H, s).

EXAMPLE 82

(±)-7-Acetyl-5-(4-aminophenyl)-8-cyano-7,8-dihydro-8-methyl-9H-1,3-dioxolo/4,5-h//2,3/-benzodiazepine hydrochloride hydrate To 0.95 g (2.6 mmoles) of the compound prepared according to Example 81, 15 cm³ of diethyl ether and 3.0 cm³ of 17.3% hydrogen chloride in ether are added. The suspension is stirred at 25° C. for 90 minutes, the yellow crystals are filtered, and washed with diethyl ether.

Thus, 0.75 g of the title compound are obtained. M.p.: 241–243° C.

$^1$H NMR (DMSO-d$_6$): δ8.10 (3H, bs), 7.67 (2H, d, J=8.7 Hz), 7.33 (2H, d, J=8.7 Hz), 7.19 (1H, s), 6.70 (1H, s), 6.17 (1H, s), 6.16 (1H, s), 3.20 (1H, d, J=14.3 Hz), 3.11 (1H, d, J=14.3 Hz), 2.17 (3H, s), 1.72 (3H, s).

EXAMPLE 83

(±)-5-(4-Aminophenyl)-8-cyano-7,8-dihydro-8-methyl-7-(pyrrolidine-1-carbonyl)-9H-1,3-dioxolo/4, 5-h//2,3/benzodiazepine 5.5 g (12.3 mmoles) of the compound prepared according to Example 72 are transferred to a mixture of 330 cm³ of methanol and 55 cm³ of water. To the mixture, 3.3 g of 10% palladium/carbon catalyst are added, then 11.0 cm³ (226 mmoles) of 98% hydrazine hydrate are added in 15 minutes. The reaction mixture is stirred at room temperature for 5 hours. The catalyst is filtered, and washed three times using 100 cm³ of methanol each time. The filtrate is evaporated under reduced pressure, and, to the residue, 100 cm³ of water are added. After 1 hour's stirring, the crystals are filtered, and washed three times with 15 cm³ of water each time. The 4.0 g (78.0%) of the crude product obtained are transferred to a silica gel column that is eluted with chloroform. The adequate fraction is evaporated under reduced pressure, the residue is stirred in diisopropyl ether, the crystals are filtered, washed three times using 10 cm³ of diisopropyl ether each time, and dried under a lamp emitting infra red radiation.

Thus, 2.8 g (54.6%) of the title compound are obtained. M.p.: 188–190° C.

Analysis: for $C_{23}H_{23}N_5O_3$ (417.47).

calculated: C, 66.17%; H, 5.55%; N, 16.78%.

found: C, 65.96%; H, 5.58%; N, 16.54%.

$^1$H NMR (CDCl$_3$): δ7.54 (2H, d, J=8.6 Hz), 6.91 (1H, s), 6.66 (2H, d, J=8.6 Hz), 6.66 (1H, s), 6.05 (1H, d, J=1.3 Hz), 6.04 (1H, d, J=1.3 Hz), 4.21 (2H, bs), 3.2 (4H, b), 3.04 (1H, d, J=13.8 Hz), 2.79 (1H, d, J=13.8 Hz), 1.81 (3H, s), 1.74 (4H, b).

EXAMPLE 84

(±)-5-(4-Aminophenyl)-8-cyano-7,8-dihydro-8-methyl-7-(morpholine-4-carbonyl)-9H-1,3-dioxolo/4,5-h//2,3/benzodiazepine 2.5 g (5.4 mmoles) of the compound prepared according to Example 71 are transferred to a mixture of 80 cm³ of ethanol and 20 cm³ of water. To the mixture, 0.5 g of 10% palladium/carbon catalyst are added, then 5.0 cm³ (100.8 mmoles) of hydrazine hydrate are added in 15 minutes. The reaction mixture is stirred at room temperature for 24 hours, the catalyst is filtered, and washed three times using 50 cm³ of methanol each time. The filtrate is evaporated under reduced pressure, and 100 cm³ of water are added to the residue. After 1 hour's stirring, the crystals are filtered, and washed three times with 20 cm³ of water each time. The 1.1 g (47.0%) of crude product obtained are transferred to a silica gel column that is eluted with a mixture of chloroform and methanol in a ratio of 9 to 1. The adequate fraction is evaporated under reduced pressure, the is stirred in 20 cm³ of diisopropyl ether, the crystals obtained are filtered, washed three times using 10 cm³ of diisopropyl ether each time, and dried under a lamp emitting infra red radiation.

Thus, 0.4 g (17.1%) of the title compound are obtained. M.p.: 236–238° C.

Analysis: for $C_{23}H_{23}N_5O_4$ (433.47).

calculated: C, 63.73%; H, 5.35%; N, 16.16%.

found: C, 63.03%; H, 5.48%; N, 15.84%.

$^1$H NMR (CDCl$_3$): δ7.53 (2H, d, J=8.7 Hz), 6.89 (1H, s), 6.67 (2H, d, J=8.7 Hz), 6.63 (1H, s), 6.07 (2H, s), 4.16 (2H, bs), 3.60 (4H, t, J=4.7 Hz), 3.24 (4H, m), 3.13 (1H, d, J=13.9 Hz), 2.79 (1H, d, J=13.9 Hz), 1.77 (3H, s).

EXAMPLE 85

(±)-5-(4-Aminophenyl)-8-cyano-7,8-dihydro-8-methyl-7-(pyridine-3-carbonyl)-9H-1,3-dioxolo-/4,5-h//2,3/benzodiazepine dihydrate 7.5 g (16.46 mmoles) of the compound prepared according to Example 69 are reduced using the method of Example 84. 2.0 g (26.3%) of the title compound are obtained. M.p.: 244–245° C.

Analysis: for $C_{24}H_{19}N_5O_3$ (461.46).

calculated: C, 62.47%; H, 5.02%; N, 15.18%.

found: C, 63.36%; H, 4.73%; N, 14.80%.

$^1$H NMR (CDCl$_3$) δ8.65 (1H, dd, J=4.9 and 1.7 Hz), 8.57 (1H, d, J=1.4 Hz), 7.75 (1H, dt, J=7.9 and 1.9 Hz), 7.36 7.28 (1H, m), 7.09 (2H, d, J=8.7 Hz), 7.03 (1H, s), 6.75 (1H, s), 6.53 (2H, d, J=8.7 Hz), 6.10 (1H, d, J=1.3 Hz), 6.06 (1H, d, J=1.3 Hz), 4.15 (2H, bs), 3.08 (2H, bs), 1.95 (3H, s).

EXAMPLE 86

(±)-5-(4-Aminophenyl)-8-cyano-7,8-dihydro-8-methyl-7-propionyl-9H-1,3-dioxolo/4,5-h//2,3/-benzodiazepine 4.5 g (11.1 mmoles) of the compound prepared according to Example 67 are transferred into a mixture of 360 cm³ of ethanol and 90 cm³ of water. To the mixture, 2.7 g 10% palladium/carbon catalyst are added, then, in 25 minutes, 18.0 cm³ (363 mmoles) of 98% hydrazine hydrate are added at 15 to 20° C. The mixture is stirred at room temperature for 5 days. The, the catalyst is filtered, washed three times using 100 cm³ of ethanol each time, the three times with 300 cm³ of chloroform each time. The filtrate is evaporated under reduced pressure, and, to the crystalline residue, 150 cm³ of water are added. After 1 hour's stirring, the crystals are filtered, and washed three times using 30 cm³ of water each time. The 3.2 g (76.8%) of the crude product are transferred to a silica gel column that is eluted with a mixture of chloroform and methanol in a ratio of 9:1. The adequate fraction is evaporated, and the residue is crystallized from 30 cm³ of ether. The crystals obtained are filtered, and washed with a large quantity of ether.

Thus, 1.28 g (30.7%) of the title compound are obtained. M.p.: 212–214° C.

Analysis: for $C_{21}H_{20}N_4O_3$ (376.42).

calculated: N, 14.88%.

found: N, 14.69%.

$^1$H NMR (DMSO-d$_6$): δ7.35 (2H, d, J=8.8 Hz), 7.11 (1H, s), 6.87 (1H, s), 6.61 (2H, d, J=8.8 Hz), 6.13 (1H, s), 6.12 (1H, s), 6.12 (1H, s), 5.8 (2H, bs), 3.08 (1H, d, J=14.4 Hz), 2.95 (1H, d, J=14.4 Hz), 2.6–2.2 (2H, m), 1.68 (3H, s), 0.96 (3H, t, J=7.2 Hz).

EXAMPLE 87

(±)-5-(4-Aminophenyl)-7-butyryl-8-cyano-7,8-dihydro-8-methyl-9H-1,3-dioxolo/4,5-h//2,3/-benzodiazepine 4.1 g (9.75 mmoles) of the compound prepared according to Example 68 are transferred into a mixture of 330 cm³ of ethanol and 80 cm³ of water. To the mixture, 2.5 g of 10% palladium/carbon catalyst are added, then, in 15 minutes, 16.4 cm³ (330 mmoles) of 98% hydrazine hydrate are added at 20 to 30° C. The mixture is stirred at room temperature for 4 hours. Then, the catalyst is filtered, and washed three times using 80 cm³ of methanol each time. The filtrate is evaporated under reduced pressure, and, to the crystalline residue, 200 cm³ of water are added. After 1 hour's stirring, the crystals are filtered, and washed three times with 30 cm³ of water each time. The crude product is transferred to a silica gel column that is eluted with a mixture of chloroform and methanol in a ratio of 15:1. The adequate fraction is evaporated, and the residue is crystallized from 25 cm³ of diisopropyl ether. The crystals obtained are filtered, and washed with diisopropyl ether.

Thus, 2.3 g (60.5%) of the title compound are obtained.
M.p.: 152–154° C.

$^1$H NMR (DMSO-d$_6$): δ7.49 (2H, d, J=8.8 Hz), 6.96 (1H, s), 6.68 (2H, d, J=8.( Hz), 6.64 (1H, s), 6.06 (1H, d, J=1.2 Hz), 6.01 (1H, d, J=1.2 Hz), 4.18 (2H, bs), 3.04 (1H, d, J=14.1 Hz), 2.90 (1H, d, J=14.1 Hz), 2.43 (2H, m), 1.81 (3H, s), 1.61 (2H, m), 0.93 (3H, t, J=7.4 Hz).

EXAMPLE 88

(±)-5-(4-Aminophenyl)-8-cyano-7,8-dihydro-7-[2-/2-(3,4-dimethoxyphenyl)-N-methyl-ethylamino/acetyl]-8-methyl-9H-1,3-dioxolo-/4,5-h//2,3/benzodiazepine 2.14 g (3.65 mmoles) of the compound prepared according to Example 75 are transferred into 60 cm$^3$ of ethanol, 3.31 g (14.7 mmoles) of crystalline tin(II) chloride (SnCl$_2$.2H$_2$O) are added, and the mixture is boiled for 1.5 hours. After cooling, the reaction mixture is evaporated. To the residue, 50 cm$^3$ of water and 100 cm$^3$ of dichloromethane are added, the phases are separated, the aqueous phase is made alkaline by adding 10% sodium hydroxide solution (pH 11 is adjusted), and the mixture is extracted three times using 100 cm$^3$ of dichloromethane each time. The combined dichloromethane phases are dried, and evaporated under reduced pressure. To the evaporation residue, 30 cm$^3$ of diisopropyl ether are added, and, after 30 minutes' stirring, the crystals are filtered, and washed with diisopropyl ether. The crude product is transferred to a silica gel column that is eluted with a mixture of chloroform and methanol in a ratio of 9:1. The adequate fraction is evaporated, and the residue is stirred in 30 cm$^3$ of diisopropyl ether for half an hour. The crystals obtained are filtered.

Thus, 0.35 g (17.3%) of the title compound are obtained.
M.p.: 112–114° C.

Analysis: for C$_{31}$H$_{33}$N$_5$O$_5$ (555.64).

calculated: N, 12.60%.

found: N, 12.41%.

$^1$H NMR (CDCl$_3$): δ7.45 (2H, d, J=8.7 Hz), 6.95 (1H, s), 6.80–6.68 (3H, m), 6.66 (2H, d, J=8.7 Hz), 6.59 (1H, s), 6.05 (1H, d, J=1.3 Hz), 5.99 (1H, d, J=1.3 Hz), 4.08 (2H, bs), 3.85 (3H, s), 3.83 (3H, s), 3.75–3.60 (1H, m), 3.25–3.45 (1H, m), 3.02 (1H, d, J=13.8 Hz), 2.95–2.60 (5H, m), 2.45 (3H, s), 1.82 (3H, s).

EXAMPLE 89

(±)-5-(4-Aminophenyl)-8-cyano-7,8-dihydro-8-methyl-7-/3-(2-morpholinoethylamino)-propionyl/-9H-1,3-dioxolo/4,5-h//2,3/-benzodiazepine 8.5 g (13.6 mmoles) of the compound prepared according to Example 79 are transferred into a mixture of 300 cm$^3$ of ethanol and 60 cm$^3$ of water. To the mixture, 3.0 g of 10% palladium/carbon catalyst are added, then, in 15 minutes, 10.0 cm$^3$ (190 mmoles) of 98% hydrazine hydrate are added. The reaction mixture is stirred at room temperature for 24 hours. The catalyst is filtered, and washed three times using 50 cm$^3$ of ethanol each time. The filtrate is evaporated under reduced pressure, and, to the residue, 200 cm$^3$ of water are added. After 2 hours' stirring, the crystals are filtered. The crude product obtained is transferred to a silica gel column that is eluted with methanol. The adequate fraction is evaporated under reduced pressure, the residue is dissolved in dichloromethane, filtered through a filter paper, and the filtrate is evaporated. The crystals obtained are suspended in 25 cm$^3$ of ether, stirred for a short time, and washed three times using 10 cm$^3$ of ether each time.

Thus, 1.45 g (21.1%) of the title compound are obtained.
M.p.: 141–143° C.

Analysis: for C$_{27}$H$_{32}$N$_6$O$_4$ (504.59).

calculated: N, 16.66%.

found: N, 16.44%.

$^1$H NMR (CDCl$_3$): δ7.47 (2H, d, J=8.8 Hz), 6.96 (1H, s), 6.66 (2H, d, J=8.8 Hz), 6.63 (1H, s), 6.06 (1H, d, J=1.2 Hz), 6.02 (1H, d, J=1.2 Hz), 4.25 (2H, bs), 3.71–3.65 (2H, m), 3.10–2.00 (17H, m), 1.81 (3H, s).

EXAMPLE 90

(±)-5-(4-Aminophenyl)-8-cyano-7,8-dihydro-7-[3-/2-(3,4-dimethoxyphenyl)-N-methyl-ethylamino/propionyl]-8-methyl-9H-1,3-dioxolo/4,5-h//2,3/benzodiazepine 10.0 g (16.6 mmoles) of the compound prepared according to Example 78 are transferred into a mixture of 350 cm$^3$ of methanol and 60 cm$^3$ of water. To the mixture, 5.0 g of 10% palladium/carbon catalyst are added, then, in 20 minutes, 30.0 cm$^3$ (605 mmoles) of 98% hydrazine hydrate are added at 15 to 20° C. The mixture is stirred at room temperature for 6.5 hours, the catalyst is filtered, and washed three times using 100 cm$^3$ of methanol each time. The filtrate is evaporated under reduced pressure, and, to the residue, 100 cm$^3$ of water are added. After 1 hour's stirring, the crystals are filtered, and washed three times with 30 cm$^3$ of water each time. The crude product is transferred to a silica gel column that is eluted with a mixture of chloroform and methanol in a ratio of 4:1. The adequate fraction is evaporated, and the residue is stirred in 30 cm$^3$ of ether for half an hour. The crystals obtained are filtered, and washed with ether.

Thus, 3.5 g (33.7%) of the title compound are obtained.
M.p.: 148–150° C.

Analysis: for C$_{32}$H$_{35}$N$_5$O$_5$ (569.64).

calculated: N, 12.29%.

found: N, 11.89%.

$^1$H NMR (CDCl$_3$): δ7.48 (2H, d, J=8.6 Hz), 6.96 (1H, s), 6.92–6.64 (3H, m), 6.62 (2H, d, J=8.6 Hz), 6.62 (1H, s), 6.05 (1H, d, J=1.3 Hz), 5.98 (1H, d, J=1.3 Hz), 4.15 (2H, bs), 3.85 (6H, s), 3.04 (1H, d, J=14.1 Hz), 2.92 (1H, d, J=14.1 Hz), 2.88–2.54 (8H, m), 2.32 (3H, s), 1.80 (3H, s).

EXAMPLE 91

(±)-5-(4-Aminophenyl)-8-cyano-7,8-dihydro-7-[3-/4-(2-fluorophenyl)piperazinyl/-propionyl]-8-methyl-9H-1,3-dioxolo-/4,5-h//2,3/benzodiazepine 16.4 g (27.5 mmoles) of the compound prepared according to Example 80 are transferred into 180 cm$^3$ of ethanol. To the mixture, 7.26 g (32.2 mmoles) of crystalline tin(II) chloride (SnCl$_2$.2H$_2$O) are added, and the reaction mixture is boiled for 3.5 hours. After cooling, the reaction mixture is evaporated under reduced pressure. To the residue, 180 cm$^3$ of water are added. The mixture is made alkaline by the addition of 135 cm$^3$ of 40% aqueous sodium hydroxide solution, and extracted three times using 400 cm$^3$ of dichloromethane each time. The dichloromethane phase is dried, and evaporated under reduced pressure. To the evaporation residue, 50 cm$^3$ of ether are added, the mixture is stirred for 30 minutes, the crystals are filtered, and washed with ether. The crude product obtained is transferred to a silica gel column that is eluted with a mixture of chloroform and methanol in a ratio of 9:1. The adequate fraction is evaporated, and the residue is crystallized from 10 cm$^3$ of ether. The crystals are filtered, and washed with ether.

Thus, 1.85 g (34.9%) of the title compound are obtained. M.p.: 159–161° C.

Analysis: for $C_{31}H_{31}FN_6O_3$ (554.63).

calculated: C, 67.13%; H, 5.63%; N, 15.15%.

found: C, 66.50%; H, 5.50%; N, 15.11%.

$^1$H NMR (CDCl$_3$): δ7.50 (2H, d, J=8.8 Hz), 7.15–6.8 (4H, m), 6.96 (1H, s), 6.67 (2H, d, J=8.8 Hz), 6.65 (1H, s), 6.05 (1H, d, J=1.3 Hz), 5.98 (1H, d, J=1.3 Hz), 4.19 (2H, bs), 3.09 (4H, t, J=4.8 Hz), 3.05–2.68 (6H, m), 2.65 (4H, t, J=4.8 Hz), 1.81 (3H, s).

EXAMPLE 92

(±)-5-(4-Aminophenyl)-8-cyano-7,8-dihydro-8-methyl-7-morpholinoacetyl-9H-1,3-dioxolo-/4,5-h// 2,3/benzodiazepine 2.0 g (4.19 mmoles) of the compound prepared according to Example 74 are transferred into 70 cm$^3$ of ethanol. To the mixture, 3.8 g (16.8 mmoles) of crystalline tin(II) chloride (SnCl$_2$.2H$_2$O) are added, and the reaction mixture is boiled for 3 hours. After cooling, the reaction mixture is evaporated under reduced pressure. To the residue, 50 cm$^3$ of water and 100 cm$^3$ of dichloromethane are added. After 1 hour's stirring, the phases are separated, the pH of the aqueous phase is adjusted to 11 by the addition of 10% aqueous sodium hydroxide solution, and the mixture is extracted three times using 150 cm$^3$ of dichloromethane each time. The combined dichloromethane phases are dried, and evaporated under reduced pressure. To the evaporation residue, 30 cm$^3$ of ether are added, and, after 30 minutes' stirring, the crystals are filtered, and washed with ether. The 0.6 g (32%) of crude product obtained are transferred to a silica gel column that is eluted with a mixture of chloroform and methanol in a ratio of 15:1. The adequate fraction is evaporated, and the residue is crystallized from 20 cm$^3$ of ether, the crystals are filtered, and washed with ether.

Thus, 0.53 g (28.6%) of the title compound are obtained. M.p.: 171–172° C.

$^1$H NMR (CDCl$_3$): δ7.45 (2H, d, J=8.6 Hz), 7.00 (1H, s), 6.68 (2H, d, J=8.6 Hz), 6.65 (1H, s), 6.07 (1H, d, J=1.3 Hz), 6.03 (1H, d, J=1.3 Hz), 4.10 (2H, bs), 3.71 (4H, t, J=4.7 Hz), 3.54 (1H, d, J=14.0 Hz), 3.19 (1H, d, J=14.3 Hz), 3.04 (1H, d, J=14.0 Hz), 2.92 (1H, d, J=14.3 Hz), 2.65–2.50 (4H, m), 1.83 (3H, s).

EXAMPLE 93

(±)-5-(4-Aminophenyl)-7,8-dihydro-8-methyl-7-trifluoroacetyl-9H-1,3-dioxolo/4,5-h//2,3/-benzodiazepine-8-carboxylic acid 2.0 g (4.3 mmoles) of the compound prepared according to Example 65 are dissolved in 40 cm$^3$ of methanol. To the solution, 1.0 g of 10% palladium/carbon catalyst suspended in 10 cm$^3$ of methanol are added, and the mixture is stirred vigorously at room temperature under a hydrogen atmosphere. The reduction is finished in 7 hours. Then the catalyst is filtered, washed three times using 50 cm$^3$ of methanol each time, and the filtrate is evaporated under reduced pressure. To the residue, 20 cm$^3$ of ether are added, and the mixture is stirred for an hour. The crystals obtained are filtered, washed three times with 10 cm$^3$ of ether each time, and dried under a lamp emitting infra red radiation.

Thus, 1.25 g (53.8%) of the title compound are obtained. M.p.: 151–153° C.

Analysis: for $C_{20}H_{16}F_3N_3O_5$ (435.36).

calculated: C, 55.18%; H, 3.70%; N, 9.65%.

found: C, 54.85%; H, 3.89%; N, 9.35%.

$^1$H NMR (CDCl$_3$): δ7.18 (2H, bs), 6.88 (1H, s), 6.67 (2H, d, J=7.8 Hz), 6.55 (1H, s), 6.08 (1H, sl, 6.04 (1H, s), 4.15 (2H, bs), 3.70 (1H, d, J=16.7 Hz), 3.35 (1H, d, J=16.7 Hz), 1.78 (3H, s).

EXAMPLE 94

(±)-5-(4-Aminophenyl)-8-cyano-7,8-dihydro-8-methyl-9H-1,3-dioxolo/4,5-h//2,3/benzodiazepine-7-carboxylic acid-(dimethylamide)

2.5 g (5.93 mmoles) of the compound prepared according to Example 70 are dissolved in 90 cm$^3$ of methanol. To the solution, 0.5 g of 10% palladium/carbon catalyst suspended in 10 cm$^3$ of methanol are added, and the mixture is stirred vigorously at room temperature under hydrogen atmosphere. The reduction is finished in 25 hours. The catalyst is filtered, washed three times using 40 cm$^3$ of methanol, and the filtrate is evaporated under reduced pressure. To the residue, 30 cm$^3$ of ether are added, and the mixture is stirred for an hour. The crystals obtained are filtered, washed three times with 10 cm$^3$ of ether each time, and dried under a lamp emitting infra red radiation. The 1.6 g (68.9%) of the crude product are transferred to a silica gel column that is eluted with a mixture of chloroform and methanol in a ratio of 9:1. The adequate fraction is evaporated under reduced pressure, the residue is crystallized from 20 cm$^3$ of ether, the crystals are filtered, washed with ether, and dried in a drying pistol at 120° C.

Thus, 1.17 g (50.4%) of the title compound are obtained. M.p.: 248–250° C.

$^1$H NMR (CDCl$_3$) δ7.36 (2H, d, J=8.6 Hz), 7.13 (1H, s), 6.70 (1H, s), 6.65 (2H, d, J=8.6 Hz), 6.12 (2H, s), 5.84 (2H, s), 2.94 (2H, bs), 2.65 (6H, bs), 1.59 (3H, s).

EXAMPLE 95

(±)-5-(4-Aminophenyl)-7,8-dihydro-8-methyl-9H-1, 3-dioxolo/4,5-h//2,3/benzodiazepine-8-carboxamide 3.2 g (8.69 mmoles) of the compound prepared according to Example 59 are transferred into 80 cm$^3$ of ethanol, 7.84 g (34.75 mmoles) of crystalline tin(II) chloride (SnCl$_2$.2H$_2$O) are added, and the mixture is boiled for 90 minutes. After cooling, the reaction mixture is evaporated under reduced pressure. To the residue, 150 cm$^3$ of water are added, and the mixture is extracted three times using 100 cm$^3$ of dichloromethane each time. The organic phase contains only by-products. The aqueous phase is made alkaline by the addition of 120 cm$^3$ of 10% sodium hydroxide solution (pH=11), and extracted three times using 200 cm$^3$ of dichloromethane each time. The dichloromethane phase is dried, and evaporated under reduced pressure. To the evaporation residue, 40 cm$^3$ of diisopropyl ether are added, the mixture is stirred for 30 minutes, the crystals are filtered, and washed three times with 10 cm$^3$ of diisopropyl ether each time. The 1.1 g (37.4%) of crude product obtained are boiled in 25 cm$^3$ of ethanol, cooled, filtered, and washed with a large quantity of ether.

Thus, 0.6 g (20.4%) of the title compound are obtained. M.p.: 248–249° C.

$^1$H NMR (CDCl$_3$): δ7.21 (2H, d, J=8.6 Hz), 7.08 (2H, m), 6.78 (1H, s), 6.54 (2H, d, J=8.6 Hz), 6.49 (1H, s), 6.06 (1H, s), 6.03 (1H, d, J=1.1 Hz), 6.01 (1H, d, J=1.1 Hz), 5.28. (2H, bs), 2.77 (1H, d, J=13.6 Hz), 2.56 (1H, d, J=13.6 Hz), 1.29 (3H, s).

EXAMPLE 96

(±)-5-(4-Aminophenyl)-8-cyano-7,8-dihydro-8-methyl-7-trifluoroacetyl-9H-1,3-dioxolo-/4,5-h//2,3/ benzodiazepine 4.0 g (8.96 mmoles) of the compound prepared according to Example 64 are transferred into 160 cm³ of ethanol, 9.0 g (40.0 mmoles) of crystalline tin(II) chloride ($SnCl_2 \cdot 2H_2O$) are added, and the mixture is boiled for 90 minutes. After cooling, the reaction mixture is evaporated under reduced pressure. To the residue, 120 cm³ of water are added, and the mixture is extracted twice using 150 cm³ of dichloromethane each time. The organic phase is washed twice with 30 cm³ of 5% aqueous sodium hydroxide solution each time, then once with 100 cm³ of water. The pH of the aqueous phase is adjusted with 10% aqueous sodium hydroxide solution to a value of 10, and it is extracted three times using 70 cm³ of dichloromethane each time. The dichloromethane layers obtained before and after the alkalization are combined, dried, and evaporated under reduced pressure. To the evaporation residue, 50 cm³ of diisopropyl ether are added, after 60 minutes' stirring, the crystals are filtered, and washed three times using 10 cm³ of diisopropyl ether each time. The 1.7 g (45.6%) of crude product obtained are transferred to a silica gel column that is eluted with pure chloroform. The $R_f$ value of the product amounts to 0.53 in a mixture of toluene and methanol in a ratio of 7:3. The fraction containing the product is evaporated under reduced pressure, the residue is crystallized from 10 cm³ of n-hexane. The crystals are filtered, and washed with 10 cm³ of n-hexane. Thus, 0.7 g (18.7%) of the title compound are obtained. M.p.: 129–130° C.

Analysis: for $C_{20}H_{15}F_3N_4O_3$ (416.36).

calculated: N, 13.46%.

found: N, 13.12%.

$^1$H NMR ($CDCl_3$): δ7.49 (2H, d, J=8.7 Hz), 6.98 (1H, s), 6.67 (2H, d, J=8.7 Hz), 6.66 (1H, s), 6.09 (1H, d, J=1.3 Hz), 6.05 (1H, d, J=1.3 Hz), 4.14 (2H, bs), 3.15 (1H, d, J=14.4 Hz), 2.98 (1H, bs), 1.89 (3H, s).

EXAMPLE 97

(±)-7-Acetyl-5-(4-aminophenyl)-7,8-dihydro-8-methyl-9H-1,3-dioxolo/4,5-h//2,3/benzodiazepine-8-carboxamide 1.5 g (3.66 mmoles) of the compound prepared according to Example 62 are transferred into 50 cm³ of ethanol, 3.31 g (14.67 mmoles) of crystalline tin(II) chloride ($SnCl_2 \cdot 2H_2O$) are added, and the mixture is boiled for 5 hours. After cooling, the reaction mixture is evaporated under reduced pressure. To the residue, 50 cm³ of water are added, and the mixture is extracted three times using 70 cm³ of dichloromethane each time. The pH of the aqueous phase is adjusted with 30% aqueous sodium hydroxide solution to a value of 11, and the solution is extracted three times with 100 cm³ of dichloromethane each time. The aqueous phase is saturated with sodium chloride, and extracted again three times using 70 cm³ of dichloromethane each time. The dichloromethane phases are combined, dried, and evaporated under reduced pressure. The 1.25 g of evaporation residue are transferred to a silica gel column that is eluted with a mixture of chloroform and methanol in a ratio of 9:1. The fraction containing the product is evaporated under reduced pressure, and the residue is crystallized from 10 cm³ of ether. The crystals are filtered, and washed three times using 10 cm³ of ether each time. The 0.6 g (43.1%) of crude product obtained are boiled in 4 cm³ of isopropanol for 5 minutes, then cooled, filtered, and washed three times with 3 cm³ of ether each time.

Thus, 0.4 g (28.8%) of the title compound are obtained. M.p.: 182–184° C.

$^1$H NMR (DMSO-$d_6$, 140° C.): δ7.31 (2H, d, J=8.8 Hz), 6.86 (1H, s), 6.63 (2H, d, J=8.8 Hz), 6.57 (1H, s), 6.11 (2H, bs), 6.03 (2H, s), 5.23 (2H, bs), 2.84 (1H, d, J=13.6 Hz), 2.71 (1H, d, J=13.6 Hz), 2.08 (3H, s), 1.52 (3H, s).

EXAMPLE 98

(±)-7-Acetyl-5-(4-aminophenyl)-7,8-dihydro-8-methyl-9H-1,3-dioxolo/4,5-h//2,3/benzodiazepine-8-carboxamide monohydrochloride 15 cm³ of concentrated hydrochlorid acid are cooled to −20° C., and 1.0 g (2.76 mmoles) of the compound prepared according to Example 81 are added in 10 minutes. The mixture is allowed to warm to 5 to 10° C., then stirred at 10° C. for 2 hours. The suspension is cooled again to −20° C., and, after 15 minutes' stirring, the crystals are filtered. The crude product is stirred in 30 cm³ of diethyl ether for 30 minutes, then filtered, and washed with diethyl ether.

Thus, 0.8 g (69.5%) of the title compound are obtained. M.p.: 240–244° C.

Analysis: for $C_{20}H_{21}ClN_4O_4$ (416.87).

calculated: Cl, 8.50%; N, 13.44%.

found: Cl, 8.11%; N, 13.80%.

$^1$H NMR (DMSO-$d_6$): δ7.59 (2H, d, J=8.4 Hz), 7.25 (2H, d, J=8.4 Hz), 7.00 (1H, s), 6.95–6.70 (2H, br), 6.61 (1H, s), 6.11 (1H, s), 6.10 (1H, s), 3.1–2.88 (1H, m), 2.83 (1H, d, J=14.0 Hz), 2.20 (3H, s), 1.47 (3H, s).

EXAMPLE 99

(±)-5-(4-Aminophenyl)-8-cyano-7,8-dihydro-8-methyl-7-chloroacetyl-9H-1,3-dioxolo-/4,5-h//2,3/ benzodiazepine 4.28 g (10.0 mmoles) of the compound prepared according to Example 73 are transferred into 120 cm³ of ethanol, 11.26 g (50 mmoles) of crystalline tin(II) chloride ($SnCl_2 \cdot 2H_2O$) are added, and the mixture is boiled for 120 minutes. After cooling, the reaction mixture is evaporated under reduced pressure. To the residue, 120 cm³ of water are added, the pH is adjusted by the addition of a 10% aqueous sodium hydroxide solution to a value of 11, and the mixture is extracted five times using 200 cm³ of dichloromethane each time. The dichloromethane phase is washed twice with 100 cm³ of water each time, dried over anhydrous magnesium sulfate, and evaporated under reduced pressure. To to evaporation residue, 70 cm³ of diisopropyl ether are added, the mixture is stirred for 30 minutes, the crystals are filtered, and washed three times using 10 cm³ of diisopropyl ether each time. The crude product is boiled in 20 cm³ of methanol, cooled, and filtered.

Thus, 0.6 g (15.2%) of the title compound are obtained. M.p.: 238–242° C.

Analysis: for $C_{20}H_{17}ClN_4O_3$ (396.84).

calculated: Cl, 8.93%; N, 14.12%.

found: Cl, 8.72%; N, 13.54%.

¹H NMR (CDCl₃+DMSO-d₆): δ7.41 (2H, d, J=6.8 Hz), 6.97 (1H, s), 6.68 (2H, d, J=6.8 Hz), 6.66 (1H, s), 6.09 (1H, s), 6.07 (1H, s), 4.97 (2H, bs), 4.40 (1H, d, J=14.4 Hz), 4.35–4.15 (1H, bs), 3.15–2.85 (2H, m), 1.82 (3H, s).

EXAMPLE 100

(±)-7-Acetyl-5-(4-aminophenyl)-8-cyano-7,8-dihydro-8-methyl-9H-1,3-dioxolo/4,5-h//2,3/-benzodiazepine 2.5 g (6.9 mmoles) of the compound prepared according to Example 81 are transferred to 25 cm³ of acetic anhydride. After 20 minutes' stirring, a solution is obtained. The solution is stirred for 18 hours, then poured into 250 cm³ of water. The mixture is stirred at 5 to 10° C. for 30 minutes, the crystals precipitated are filtered, washed three times with 60 cm³ of water each time, and twice with 40 cm³ of ether each time. The 2.69 cm³ (96.4%) of the crude product are stirred in 30 cm³ of ethyl acetate for an hour, the crystals are filtered, washed with ethyl acetate and ether.

Thus, 1.88 g (67.3%) of the title compound are obtained. M.p.: 162–163° C.

Analysis: for $C_{22}H_{20}N_4O_4$ (404.43).

calculated: N, 13.85%.

found: N, 13.32%.

¹H NMR (DMSO-d₆): δ10.23 (1H, s), 7.71 (2H, d, J=8.7 Hz), 7.58 (2H, d, J=8.7 Hz), 7.16 (1H, s), 6.67 (1H, s), 6.15 (1H, s), 6.14 (1H, s), 3.17 (1H, d, J=14.2 Hz), 3.05 (1H, d, J=14.2 Hz), 2.14 (3H, s), 2.09 (3H, s), 1.71 (3H, s).

EXAMPLE 101

(±)-8-Cyano-7,8-dihydro-7-[2-/4-(2-fluoro-phenyl)piperazinyl/acetyl]-8-methyl-5-(4-nitrophenyl)-9H-1,3-dioxolo/4,5-h//2,3/-benzodiazepine To 5.33 g (12.5 mmoles) of the compound prepared according to Example 73, 75 cm³ of acetonitrile and 4.05 g (22.5 mmoles) of 2-fluorophenyl-piperazine are added. The reaction mixture is boiled for 7 hours, then evaporated under reduced pressure. The evaporation residue is stirred in 20 cm³ of water for 1.5 hours, the crystals precipitated are filtered, and washed with water. The crude product is transferred to a silica gel column that is eluted with a mixture of cyclohexane and ethyl acetate. The adequate fraction is evaporated under reduced pressure, the residue is crystallized from 25 cm³ of ethanol, the crystals are filtered, and washed with ethanol.

Thus, 2.70 g (37.9%) of the title compound are obtained. M.p.: 148–150° C.

¹H NMR (CDCl₃): δ8.31 (2H, d, J=8.8 Hz), 7.81 (2H, d, J=8.8 Hz), 7.10–6.90 (4H, m), 7.00 (1H, s), 6.53 (1H, s), 6.10 (1H, s), 6.07 (1H, s), 3.67 (1H, d, J=16.7 Hz), 3.41 (1H, d, J=16.7 Hz), 3.20–3.05 (6H, m), 2.95–2.80 (2H, m), 2.80–2.6 (2H, m), 1.88 (3H, s).

EXAMPLE 102

(±)-5-(4-Aminophenyl)-8-cyano-7,8-dihydro-7-[2-/4-(2-fluorophenyl)piperazinyl/-acetyl]-8-methyl-9H-1,3-dioxolo/4,5-h//2,3/-benzodiazepine 5 g (8.8 mmoles) of the compound prepared according to Example 101 are dissolved in a mixture of 230 cm³ of methanol and 50 cm³ of water, and a suspension of 3 g of 10% palladium/carbon catalyst in 20 cm³ of methanol is added. To the mixture, 10 cm³ (200 mmoles) of hydrazine hydrate are added, drop by drop, in 15 minutes, and the reaction mixture is stirred vigorously at room temperature for 3.5 hours. The catalyst is filtered, washed three times using 40 cm³ of methanol each time, and the filtrate is evaporated under reduced pressure. To the residue, 200 cm³ of water are added, and the mixture is stirred for an hour. The crystals obtained are filtered. The crude product is transferred to a silica gel column that is eluted with a mixture of chloroform and methanol in a ratio of 9:1. The adequate fraction is evaporated under reduced pressure, the residue is crystallized from 20 cm³ of diisopropyl ether, filtered, and washed with diisopropyl ether.

Thus, 1.9 g (40.2%) of the title compound are obtained. M.p.: 124–126° C.

¹H NMR (CDCl₃) δ7.46 (2H, d, J=8.5 Hz), 7.1–6.8 (4H, m), 6.96 (1H, s), 6.68 (2H, d, J=8.5 Hz), 6.67 (1H, s), 6.06 (1H, 5), 6.02 (1H, s), 4.19 (2H, bs), 3.64 (1H, d, J=16.6 Hz), 3.0 (1H, m), 3.3–2.6 (10H, m), 1.84 (3H, s).

What is claimed is:

1. A 8-substituted-9H-1,3-dioxolo-(4,5-h)(2,3) benzodiazepine compound of the formula I

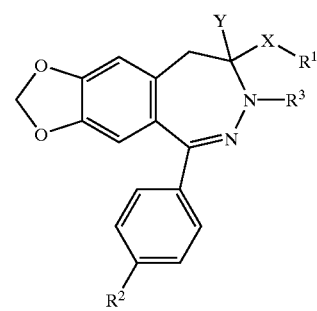

wherein

X represents a carbonyl group or a methylene group, and $R^1$ stands for a hydrogen atom, a hydroxy group, a $C_{1-4}$ alkoxy group, a $C_{1-4}$ alkanoyloxy group, a ($C_{1-4}$ alkyl) sulfonyloxy group or a group of the formula —$NR^4R^5$, wherein $R^4$ and $R^5$ mean, independently, a hydrogen atom, a $C_{1-4}$ alkoxy group, a $C_{1-4}$ alkanoyl group or a $C_{1-6}$ alkyl group which latter is optionally substituted by a saturated or unsaturated heterocyclic group having 5 or 6 members and comprising one or two nitrogen atom(s) or a nitrogen atom and an oxygen atom as the heteroatom, or by an N-(phenyl-($C_{1-4}$alkyl))-N-($C_{1-4}$ alkyl)amino group, wherein the phenyl group is optionally substituted by 1 to 3 substituent(s), wherein the substituent consists of a $C_{1-4}$ alkoxy group, or $R^4$ and $R^5$ form with the adjacent nitrogen atom and optionally with a further nitrogen atom or an oxygen atom, a saturated or unsaturated heterocyclic group having 5 to 10 members, or X forms together with $R^1$ a cyano group, a tetrazolyl group, a group of the formula —CHNOH, or a group of the formula —$COR^6$, wherein $R^6$ means a hydroxy group, a $C_{1-4}$ alkoxy group, a phenoxy group, a naphthyloxy group, or an amino group which latter is optionally substituted by a $C_{1-4}$ alkyl group, $R^2$ stands for a nitro group, an amino group or a ($C_{1-4}$ alkanoyl)amino group, $R^3$ represents a hydrogen atom, a $C_{1-4}$ alkyl group, or a group of the formula —$COR^7$, wherein $R^7$ represents a hydrogen atom, a $C_{1-6}$ alkyl group, a $C_{1-6}$ alkyl group substituted by 1 to 3 halo atom(s), a $C_{1-4}$ alkoxy group, a phenoxy group, a pyridyl group, a phenyl group or a naphthyl group which two latter groups are optionally substituted by 1 to 3 substituent(s), or a group of the formula —$(CH_2)_n$—$NR^8R^9$, wherein $R^8$ and $R^9$ represent, independently, a hydrogen atom, a $C_{1-4}$ alkyl group optionally substituted by a phenyl group or a saturated heterocyclic group having 5 or 6 members and containing a nitrogen group or a nitrogen and an oxygen group, and said phenyl group is optionally substituted by 1 to 3 substituent(s), wherein the substituent consists of a $C_{1-4}$ alkoxy group, or $R^8$ and $R^9$ form, together with the adjacent nitrogen atom and optionally a further nitrogen or oxygen atom, a saturated or unsaturated heterocyclic group having 5 or 6 members and being optionally substituted by a phenyl group that is optionally substituted by 1 to 3 substituents, wherein the substituent consists of a halo atom or a $C_{1-4}$ alkoxy group, n has a value of 0, 1 or 2, Y is a hydrogen atom, or a methyl group, or Y forms together with $R^3$ a valence bond between the carbon atom in position 8 and the nitrogen atom in position 7, with the proviso that 1) if Y stands for a hydrogen atom or forms together with $R^3$ a valence bond and
  a) X represents a methylene group, then $R^1$ is other than a hydrogen atom, hydroxy, amino or $C_{1-4}$ alkylamino group; or
  b) X represents a carbonyl group, then $R^1$ is other than a hydrogen atom, hydroxy or $C_{1-4}$ alkoxy group; and 2) if Y stands for a hydrogen atom or a methyl group and $R^3$ represents a $C_{1-4}$ alkyl group or a group of the formula —$COR^7$, then X is other than a methylene group, 3) if X represents a methylene group, $R^2$ stands for a nitro group and Y forms with $R^3$ a valence bond, then $R^1$ is other than —NHAC, and pharmaceutically suitable acid addition salts and quaternary ammonium salts thereof.

2. A 8-substituted-9H-1,3-dioxolo-(4,5-h)(2,3) benzodiazepine compound as claimed in claim 1, wherein X represents a carbonyl group or a methylene group, and $R^1$ stands for a hydrogen atom, a hydroxy group, a methoxy group, an acetoxy group, a methylsulfonyloxy group or a group of the formula —$NR^4R^5$, wherein $R^4$ and $R^5$ mean, independently, a hydrogen atom, a methoxy group, an acetyl group or a $C_{1-4}$ alkyl group which latter is optionally substituted by a morpholino or an N-(dimethoxyphenylethyl)-N-(methyl) amino group, or $R^4$ and $R^5$ form with the adjacent nitrogen atom and optionally with a further nitrogen atom or an oxygen atom a saturated or unsaturated heterocyclic group having 5 to 9 members, or X forms together with $R^1$ a cyano group, a tetrazolyl group or a group of the formula —CHNOH, $R^2$ stands for a nitro group or an amino group, $R^3$ represents a hydrogen atom or an acetyl group, Y is a hydrogen atom, or Y forms together with $R^3$ a valence bond between the carbon atom in position 8 and the nitrogen atom in position 7, with the proviso that 1) if Y stands for a hydrogen atom or forms together with $R^3$ a valence bond and
  a) X represents a methylene group, then $R^1$ is other than a hydrogen atom, hydroxy, amino or $C_{1-4}$ alkylamino group; or
  b) X represents a carbonyl group, then $R^1$ is other than a hydrogen atom, hydroxy or methoxy group; and 2) if X represents a methylene group, $R^2$ stands for a nitro group and Y forms with $R^3$ a valence bond, then $R^1$ is other than —NHAc, and pharmaceutically suitable acid addition salts and quaternary ammonium salts thereof.

3. The compound of claim 1 wherein the compound is selected from the group consisting of 5-(4-aminophenyl)-9H-1,3-dioxolo-(4,5-h)(2,3)benzodiazepine-8-carboxylic amide, 5-(4-aminophenyl)-8-cyano-9H-1,3-dioxolo-(4,5-h)(2,3)benzodiazepine, 5-(4-aminophenyl)-8-(5-tetrazolyl)-9H-1,3-dioxolo(4,5-h)(2,3)benzodiazepine, and pharmaceutically suitable acid addition salts and quaternary ammonium salts thereof.

4. A 8-substituted-9H-1,3-dioxolo-(4,5-h)(2,3) benzodiazepine compound as claimed in claim 1, wherein $R^3$ represents a hydrogen atom or a group of the formula —$COR^7$, wherein $R^7$ stands for a hydrogen atom, a $C_{1-4}$ alkyl group, a $C_{1-4}$ alkyl group substituted by 1 to 3 halo atom(s), or a group of the formula —$(CH_2)_n$—$NR^8R^9$, wherein $R^8$ and $R^9$ mean, independently, a hydrogen atom, a $C_{1-4}$ alkyl group optionally substituted by a phenyl group or a morpholino group, and the phenyl group is optionally substituted by one or two methoxy group(s), or $R^8$ and $R^9$ form, together with the adjacent nitrogen atom and optionally a further nitrogen or oxygen atom, a saturated or unsaturated heterocyclic group having 5 or 6 members and being optionally substituted by a phenyl group that is optionally substituted by a halo atom or a methoxy group, n has a value of 0, 1 or 2, X forms together with $R^1$ a cyano group or a group of the formula —$COR^6$, wherein $R^6$ represents a hydroxy group or an amino group, Y stands for a methyl group, $R^2$ is a nitro group, an amino group, or a ($C_{1-4}$ alkanoyl) amino group, and pharmaceutically suitable acid addition salts thereof.

5. A 8-substituted-9H-1,3-dioxolo(4,5-h)(2,3) benzodiazepine compound as claimed in claim 4, wherein $R^3$ represents a: hydrogen atom or a group of the formula —$COR^7$, wherein $R^7$ stands for a hydrogen atom, a $C_{1-4}$ alkyl group, a $C_{1-2}$ alkyl group substituted by a chloro atom, a trifluoromethyl group, a trichloromethyl group or a group of the formula —$(CH_2)_n$—$NR^8R^9$, wherein $R^8$ and $R^9$ represent, independently, a hydrogen atom, a $C_{1-2}$ alkyl group optionally substituted by a phenyl group or a morpholino group, and the phenyl group is optionally substituted by two methoxy groups, or $R^8$ and $R^9$ form, together with the adjacent nitrogen atom and optionally a further nitrogen or oxygen atom, a pyridinyl, pyrrolidinyl, morpholino or piperazinyl group, wherein the piperazinyl group is substituted by a fluorophenyl or a methoxyphenyl group, n has a value of 0, 1 or 2, X forms together with $R^1$ a cyano group, $R^2$ means an amino group or a ($C_{1-4}$ alkanoyl)-amino group, Y stands for a methyl group, and pharmaceutically suitable acid addition salts thereof.

6. A 8-substituted-9H-1,3-dioxolo(4,5-h)(2,3) benzodiazepine compound as claimed in claim 5, wherein $R^2$ represents an acetylamino or a propionylamino group, $R^1$, $R^3$, X and Y are as defined in claim 5, and pharmaceutically suitable acid addition salts thereof.

7. A process for the preparation of 8-substituted-9H-1,3-dioxolo(4,5-h)(2,3)-benzodiazepine compounds of the formula I of claim 1, wherein X, $R^1$, $R^2$, $R^3$ and Y are as defined in claim 1, and pharmaceutically suitable acid addition salts and quaternary ammonium salts thereof, characterized in that a) for the preparation of compounds of the formula I of claim 1, wherein $R^1$ is an imidazolyl group, $R^2$ represents a nitro group, X is a carbonyl group, and Y forms together with $R^3$ a valence bond, 5-(4-nitrophenyl)-9H-1,3-dioxolo(4,5-h)(2,3)benzodiazepine-8-carboxylic acid of the formula III is reacted with 1,1'-carbonyldiimidazole; or b) for the preparation of compounds of the formula I of claim 1, wherein $R^1$ is a group of the formula —$NR^4R^5$, $R^2$ represents a nitro group, X is a carbonyl group, Y forms together with $R^3$ a valence bond, $R^4$ and $R^5$ are as defined in claim 1, acid 5-(4-nitrophenyl)-9H-1,3-dioxolo(4,5-h)(2,3)benzodiazepine-8-carboxylic acid of the formula III or a reactive compound thereof of the formula IV

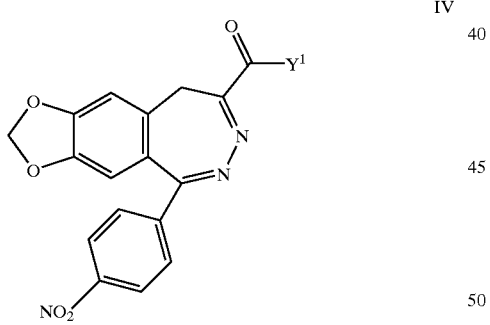

IV wherein $Y^1$ is a leaving group, is reacted with an amine of the formula V

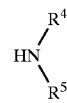

V wherein $R^4$ and $R^5$ are as defined in claim 1; or c) for the preparation of compounds of the formula I of claim 1, wherein $R^1$ is a ($C_{1-4}$ alkyl)sulfonyloxy group, $R^2$ represents a nitro group, X is a methylene group, Y forms together with $R^3$ a valence bond, 8-formyl-5-(4-nitrophenyl)-9H-1,3-dioxolo (4,5-h)(2,3) benzodiazepine of the formula II is reacted with a reducing agent, and the 8-(hydroxymethyl)-5-(4-nitrophenyl)-9H-1,3-dioxolo(4,5-h)(2,3)-benzodiazepine obtained is reacted with a ($C_{1-4}$ alkyl) sulfonyl halide; or d) for the preparation of a compound of the formula I of claim 1, wherein X forms together with $R^1$ a group of the formula —CHNOH, $R^2$ represents a nitro group, Y forms together with $R^3$ a valence bond, 8-formyl-5-(4-nitrophenyl)-9H-1,3-dioxolo(4,5-h)(2,3)-benzodiazepine of the formula II is reacted with hydroxylamine; or e) for the preparation of a compound of the formula I of claim 1, wherein X forms together with $R^1$ a cyano group, $R^2$ represents a nitro group, Y forms together with $R^3$ a valence bond, 8-(hydroxyiminomethyl)-5-(4-nitrophenyl)-9H-1,3-dioxolo(4,5-h)(2-3) benzodiazepine is reacted with a dehydrating agent; or f) for the preparation of a compound of the formula I of claim 1, wherein X forms together with $R^1$ a tetrazolyl group, $R^2$ represents a nitro group, Y forms together with $R^3$ a valence bond, 8-cyano-5-(4-nitrophenyl)-9H-1,3-dioxolo(4,5-h)(2,3)benzodiazepine is reacted with an alkaline metal azide; or g) for the preparation of 7,8-dihydro compounds of the formula VI

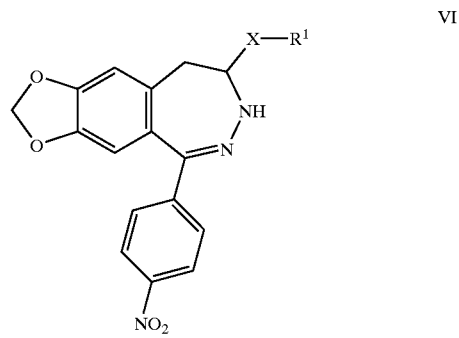

VI being a narrower group of the compounds of the formula I of claim 1, wherein X represents a carbonyl group or a methylene group, and $R^1$ is as defined in claim 1, a compound of the formula VII

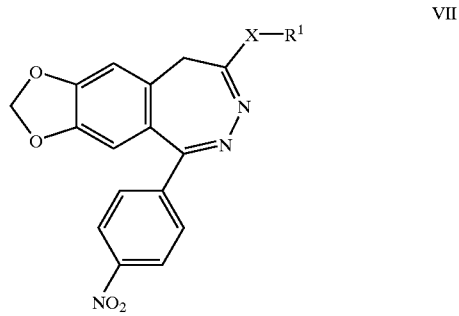

VII wherein X and $R^1$ are as defined in claim 1, is reacted with a reducing agent; or h) for the preparation of 7,8-dihydro-7-acyl compounds of the formula VIII

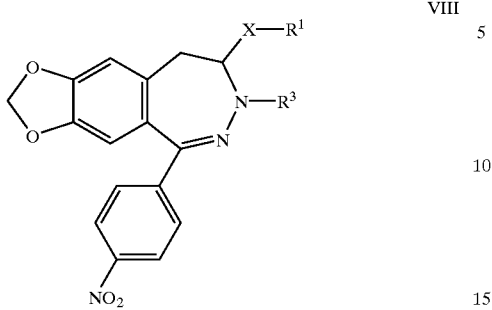

VIII being a narrower group of the compounds of the formula I of claim 1, wherein X represents a carbonyl group or a methylene group, $R^1$ is as defined in claim 1, $R^3$ represents a $C_{1-4}$ alkanoyl group, a 7,8-dihydro compound of the formula VI, wherein X and $R^1$ are as defined in claim 1, is reacted with a $C_{1-4}$ alkanecarboxylic acid or a reactive acylating salt thereof; or i) for the preparation of compounds of the formula I of claim 1, wherein $R^1$ is a group of the formula $-NR^4R^5$, $R^2$ represents a nitro group, X stands for a carbonyl group or a methylene group, one of $R^4$ and $R^5$ represents a $C_{1-4}$ alkanoyl group, while the other is as defined in claim 1, Y means a hydrogen atom and in this case $R^3$ stands for a $C_{1-4}$ alkanoyl group, or Y forms together with $R^3$ a valence bond, a compound of the formula I of claim 1, wherein $R^1$ is a group of the formula $-NR^4R^5$, wherein one of $R^4$ and $R^5$ means a hydrogen atom, while the other is as defined in claim 1, X represents a carbonyl group or a methylene group, $R^2$ represents a nitro group, Y represents a hydrogen atom and $R^3$ represents a $C_{1-4}$ alkanoyl group, is reacted with $C_{1-4}$ alkanecarboxylic acid or a reactive acylating salt thereof;

j) for the preparation of compounds of the formula I of claim 1, wherein Y represents a methyl group, $-X-R^1$ represents a cyano group, $R^3$ is a hydrogen atom, and $R^2$ is a nitro group, the compound of the formula IX

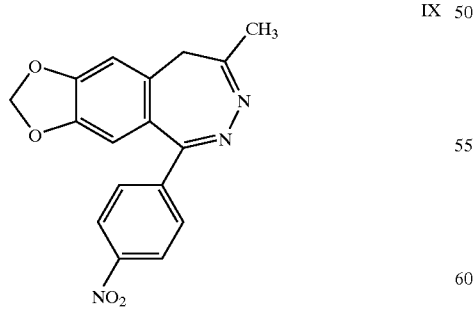

IX is reacted with hydrogen cyanide; or k) for the preparation of compounds of the formula I of claim 1, wherein Y represents a methyl group, $R^3$ is a hydrogen atom, $R^2$ is a nitro group and $-X-R^1$ represents a group of the formula $-COR^6$, wherein $R^6$ is as defined in claim 1, the compound of the formula X

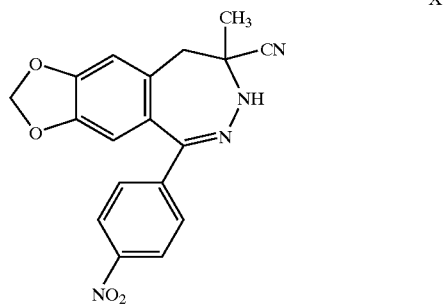

X is hydrolyzed with a mineral acid, and the carboxylic acid obtained is optionally converted to an ester or a carboxylic amide; or l) for the preparation of compounds of the formula I of claim 1, wherein Y represents a methyl group, $-X-R^1$ represents a cyano group or a group of the formula $-COR^6$, $R^2$ is a nitro group, $R^3$ is a $C_{1-4}$ alkyl group, and $R^6$ is as defined in claim 1, a compound of the formula I, wherein Y represents a methyl group, $-X-R^1$ represents for a cyano group or a group of the formula $-COR^6$, where $R^6$ is as defined in claim 1, $R^2$ is a nitro group and $R^3$ represents a hydrogen atom, is reacted with a ($C_{1-4}$ alkyl) halide; or m) for the preparation of compounds of the formula I of claim 1, wherein Y represents a methyl group, $-X-R^1$ represents a cyano group or a group of the formula $-COR^6$, $R^2$ is a nitro group, $R^3$ is a group of the formula $-COR^7$, $R^7$ represents a group of the formula $-(CH_2)_n-NR^8R^9$, $R^6$, $R^8$, $R^9$ and n are as defined in claim 1, a compound of the formula XI

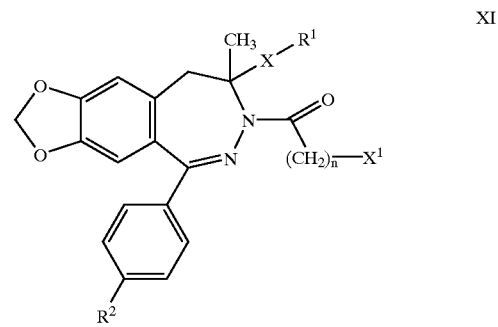

XI wherein $-X-R^1$ represents a cyano group or a group of the formula $-COR^6$, wherein $R^6$ is as defined in claim 1, $R^2$ is a nitro group and n is as defined in claim 1, $X^1$ is a leaving group, is reacted with an amine of the formula $HNR^8R^9$;

and, optionally, the compound of the formula I of claim 1, wherein $R^2$ represents a nitro group, $R^1$, $R^3$, X and Y are as defined in claim 1, is transformed into a compound of the formula I of claim 1, wherein $R^2$ represents an amino group, by reduction;

and, optionally, the compound of the formula I of claim 1, wherein $R^2$ represents an amino group, $R^1$, $R^3$, X and Y are as defined in claim 1, is reacted with a $C_{1-4}$ alkanecarboxylic acid or a reactive acylating salt thereof;

and, optionally, a base of the formula I of claim 1 is converted to a pharmaceutically suitable acid addition salt or liberated from the acid addition salt;

and, optionally, the compound of the formula I of claim 1 or pharmaceutically suitable acid addition salt thereof is converted to quarternary ammonium salt.

8. A pharmaceutical composition comprising a 8-substituted-9H-1,3-dioxolo(4,5-h)(2,3)-benzodiazepine compound of the formula I

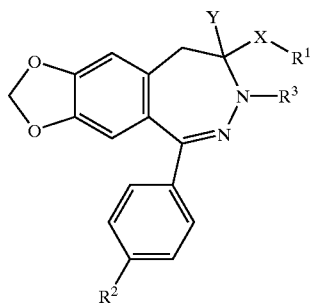

wherein,

X, Y, $R^1$, $R^2$ and $R^3$ are as defined in claim 1, or a pharmaceutically. suitable acid addition salt or a quaternary ammonium salt thereof as the active ingredient and one or more conventional carrier(s).

9. A pharmaceutical composition as claimed in claim 8, comprising a 8-substituted-9H-1,3-dioxolo(4,5-h) (2,3) benzodiazepine compound of the formula I, wherein X represents a carbonyl group or a methylene group, and $R^1$ stands for a hydrogen atom, a hydroxy group, a methoxy group, an acetoxy group, a methylsulfonyloxy group or a group of the formula —$NR^4R^5$, wherein $R^4$ and $R^5$ mean, independently, a hydrogen atom, a methoxy group, an acetyl group or a $C_{1-4}$ alkyl group which latter is optionally substituted by a morpholino or an N-(dimethoxyphenylethyl)-N-(methyl) amino group, or $R^4$ and $R^5$ form with the adjacent nitrogen atom and optionally with a further nitrogen atom or an oxygen atom a saturated or unsaturated heterocyclic group having 5 to 9 members, or X forms together with $R^1$ a cyano group, a tetrazolyl group or a group of the formula —CHNOH, $R^2$ stands for a nitro group or an amino group, $R^3$ represents a hydrogen atom or an acetyl group, Y is a hydrogen atom, or Y forms together with $R^3$ a valence bond between the carbon atom in position 8 and the nitrogen atom in position 7, with the proviso that 1) if Y stands for a hydrogen atom or forms together with $R^3$ a valence bond and
  a) X represents a methylene group, then $R^1$ is other than a hydrogen atom, hydroxy, amino or $C_{1-4}$ alkylamino group; or
  b) X represents a carbonyl group, then $R^1$ is other than a hydrogen atom, hydroxy or methoxy group; and 2) if X represents a methylene group, $R^2$ stands for a nitro group and Y forms with $R^3$ a valence bond, then $R^1$ is other than —NHAc, or a pharmaceutically suitable acid addition salt or a quaternary ammonium salt thereof as the active ingredient and a carrier.

10. A pharmaceutical composition as claimed in claim 8, wherein the active compound is selected from the group consisting of 5-(4-aminophenyl)-9H-1,3-dioxolo(4,5-h)(2,3)benzodiazepine-8-carboxylic amide, 5-(4-aminophenyl)-8-cyano-9H-1,3-dioxolo(4,5-h)(2,3)benzodiazepine, and 5-(4-aminophenyl)-8-(5-tetrazolyl)-9H-1,3-dioxolo(4,5-h) (2,3)-benzodiazepine, or a pharmaceutically suitable acid addition salt or a quaternary ammonium salt thereof as the active ingredient and a carrier.

11. A pharmaceutical composition as claimed in claim 8, comprising a 8-substituted-9H-1,3-dioxolo(4,5-h)(2,3) benzodiazepine compound of the formula I, wherein X represents a carbonyl group or a methylene group, and $R^1$ represents a hydrogen atom, a hydroxy group, a $C_{1-4}$ alkoxy group, a $C_{1-4}$ alkanoyloxy group, a ($C_{1-4}$ alkyl) sulfonyloxy group or a group of the formula —$NR^4R^5$, wherein $R^4$ and $R^5$ represent, independently, a hydrogen atom, a $C_{1-4}$ alkoxy group, a $C_{1-4}$ alkanoyl group or a $C_{1-6}$ alkyl group which latter is optionally substituted by a saturated or unsaturated heterocyclic group having 5 or 6 members and comprising one or two nitrogen atom(s) or a nitrogen atom and an oxygen atom as the heteroatom, or by an N-(phenyl-($C_{1-4}$alkyl))-N-($C_{1-4}$ alkyl)amino group, wherein the phenyl group is optionally substituted by 1 to 3 substituent(s), wherein the substituent consists of a $C_{1-4}$ alkoxy group, or $R^4$ and $R^5$ form with the adjacent nitrogen atom and optionally with a further nitrogen atom or an oxygen atom, a saturated or unsaturated heterocyclic group having 5 to 10 members, or X forms together with $R^1$ a cyano group, or a group of the formula —$COR^6$, wherein $R^6$ represents a hydroxy group or an amino group, $R^2$ is a nitro group, an amino group or a ($C_{1-4}$ alkanoyl) amino group, $R^3$ represents a hydrogen atom or a group of the formula —$COR^7$, wherein $R^7$ is a hydrogen atom, a $C_{1-4}$ alkyl group, a $C_{1-4}$ alkyl group substituted by 1 to 3 halo atom(s), or a group of the formula —$(CH_2)_n$—$NR^8R^9$, wherein $R^8$ and $R^9$ represent, independently, a hydrogen atom, a $C_{1-4}$ alkyl group optionally substituted by a phenyl group or a morpholino group, and the phenyl group is optionally substituted by one or two methoxy group(s), or $R^8$ and $R^9$ form, together with the adjacent nitrogen atom and optionally a further nitrogen or oxygen atom, a saturated or unsaturated heterocyclic group having 5 or 6 members and being optionally substituted by a phenyl group that is optionally substituted by a halo atom or a methoxy group, n has a value of 0, 1 or 2, Y is a methyl group, or with the proviso that if Y is a methyl group and $R^3$ represents a group of the formula —$COR^7$, then X is other than a methylene group, or a pharmaceutically suitable acid addition salt thereof as the active ingredient.

12. A pharmaceutical composition as claimed in claim 11, comprising a 8-substituted-9H-1,3-dioxolo(4,5-h) (2,3)-benzodiazepine compound of the formula I, X represents a carbonyl group or a methylene group, and $R^1$ represents a hydrogen atom, a hydroxy group, a $C_{1-4}$ alkoxy group, a $C_{1-4}$ alkanoyloxy group, a ($C_{1-4}$ alkyl) sulfonyloxy group or a group of the formula —$NR^4R^5$, wherein R⁴ and R⁵ represent, independently, a hydrogen atom, a $C_{1-4}$ alkoxy group, a $C_{1-4}$ alkanoyl group or a $C_{1-6}$ alkyl group which latter is optionally substituted by a saturated or unsaturated heterocyclic group having 5 or 6 members and comprising one or two nitrogen atom(s) or a nitrogen atom and an oxygen atom as the heteroatom, or by an N-(phenyl-($C_{1-4}$alkyl))-N-($C_{1-4}$ alkyl)amino group, wherein the phenyl group is optionally substituted by 1 to 3 substituent(s), wherein the substituent consists of a $C_{1-4}$ alkoxy group, or R⁴ and R⁵ form with the adjacent nitrogen atom and optionally with a further nitrogen atom or an oxygen atom, a saturated or unsaturated heterocyclic group having 5 to 10 members, or X forms together with R¹ a cyano group, R² represents an amino group or a ($C_{1-4}$ alkanoyl)amino group, R³ represents a hydrogen atom or a group of the formula —COR⁷, wherein R⁷ represents a hydrogen atom, a $C_{1-4}$ alkyl group, a $C_{1-2}$ alkyl group substituted by a chloro atom, a trifluoromethyl group, a trichloromethyl group or a group of the formula —(CH₂)ₙ—NR⁸R⁹, wherein R⁸ and R⁹ represent, independently, a hydrogen atom, a $C_{1-2}$ alkyl group optionally substituted by a phenyl group or a morpholino group, and the phenyl group is optionally substituted by two methoxy groups, or R⁸ and R⁹ form, together with the adjacent nitrogen atom and optionally a further nitrogen or oxygen atom, a pyridinyl, pyrrolidinyl, morpholino or piperazinyl group, wherein the piperazinyl group is substituted by a fluorophenyl or a methoxyphenyl group, n has a value of 0, 1 or 2, Y is a methyl group, with the proviso that if Y stands for a methyl group and R³ represents a group of the formula —COR⁷, then X is other than a methylene group, or a pharmaceutically suitable acid addition salt thereof as the active ingredient.

13. A method of treatment in which a patient suffering from epilepsy or being in a state after stroke is treated with a non-toxic dose of a 8-substituted-9H-1,3-dioxolo(4,5-h)(2,3)benzodiazepine compound of the formula I

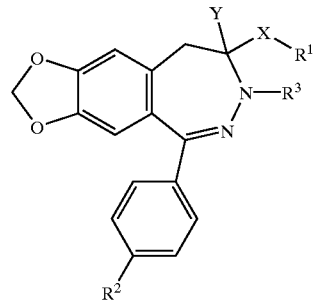

wherein X, Y, R¹, R² and R³ are as defined in claim 1, or a pharmaceutically suitable acid addition salt or a quaternary ammonium salt thereof.

14. A process for, the preparation of a pharmaceutical composition suitable for the treatment of epilepsy or a state after stroke, characterized in that a 8-substituted-9H-1,3-dioxolo(4,5-h)(2,3)benzodiazepine compound of the formula I

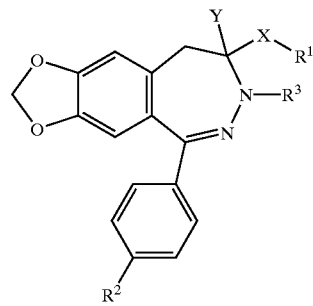

wherein X, Y, R¹, R² and R³ are as defined in claim 1, or a pharmaceutically suitable acid addition salt or a quaternary ammonium salt thereof, is converted to a pharmaceutical composition using one or more carrier(s) commonly employed in the manufacture of drugs.

* * * * *